United States Patent
Kimura et al.

[11] Patent Number: 5,773,203
[45] Date of Patent: Jun. 30, 1998

[54] 4-(N,N-DIALKYLAMINO)ANILINE COMPOUNDS, PHOTOGRAPHIC PROCESSING COMPOSITION CONTAINING THE SAME AND COLOR IMAGE-FORMING METHOD

[75] Inventors: Keizo Kimura; Shigeo Hirano; Hiroshi Kawamoto, all of Minami-ashigara, Japan

[73] Assignee: Fuji Photo Film Co., Ltd., Minami-ashigara, Japan

[21] Appl. No.: 856,015

[22] Filed: May 14, 1997

[30] Foreign Application Priority Data

May 16, 1996 [JP] Japan .................. 8-121472

[51] Int. Cl.$^6$ .................. G03C 7/407
[52] U.S. Cl. .................. 430/442; 430/435; 430/440; 430/441; 430/446; 430/480; 430/483; 430/484
[58] Field of Search .................. 430/435, 440, 430/441, 442, 446

[56] References Cited

U.S. PATENT DOCUMENTS

| | | | |
|---|---|---|---|
| 2,196,739 | 4/1940 | Peterson | 430/380 |
| 2,566,259 | 8/1951 | Thirtie et al. | 430/476 |
| 4,113,491 | 9/1978 | Deguchi et al. | 430/467 |

FOREIGN PATENT DOCUMENTS

| | | |
|---|---|---|
| 151305 | 8/1985 | European Pat. Off. . |
| 670312 | 9/1995 | European Pat. Off. . |
| 860363 | 9/1940 | France . |
| 2164220 | 7/1973 | France . |
| 45440 | 2/1992 | Japan . |
| 5-257248 | 10/1993 | Japan . |
| 6-161061 | 6/1994 | Japan . |
| 7-36162 | 2/1995 | Japan . |

*Primary Examiner*—Hoa Van Le
*Attorney, Agent, or Firm*—Burns, Doane,Swecker & Mathis, LLP

[57] ABSTRACT

Disclosed are 4-(N,N-dialkylamino)aniline compounds having a 4-N substituent which is a polyethyleneoxy group and which forms a condensed ring with benzene ring, such as aniline compounds having the following structure, a processing composition containing such a compound and a method for forming a color image with the processing solution. The aniline compound is useful as a color developing agent capable of having a low fog density and sufficient yellow and cyan image densities and suitable for the rapid process.

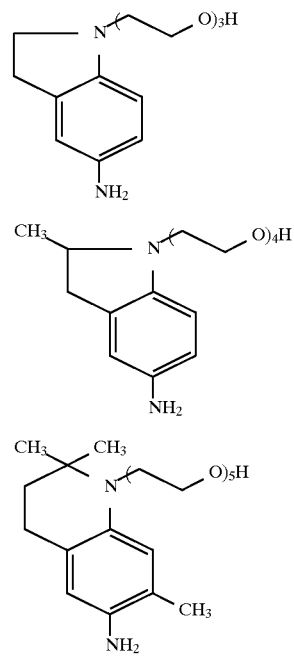

9 Claims, No Drawings

4-(N,N-DIALKYLAMINO)ANILINE COMPOUNDS, PHOTOGRAPHIC PROCESSING COMPOSITION CONTAINING THE SAME AND COLOR IMAGE-FORMING METHOD

BACKGROUND OF THE INVENTION

The present invention relates to 4-(N,N-dialkylamino) aniline compounds having a 4-N substituent which is a polyethyleneoxy group and which forms a condensed ring with benzene ring, a processing composition containing such a compound and a method for forming a color image with the processing solution.

4-(N,N-dialkylamino)aniline compounds are useful as a developing agent for a silver halide color photographic material and they are described in, for example, Japanese Patent Unexamined Published Application (hereinafter referred to as "J. P. KOKAI") No. Hei 5-257248, 6-161061 and 7-36162.

As mini-labs for processing photosensitive materials within the shops and the amount of color negative films used in the field of news photos are increasing recently, the demand for completion of the development process in a shorter time to immediately provide the prints to the customers or to immediately place the photo in newspapers or the like is rapidly increasing. The demand for reduction of the processing time is becoming more and more eager in processing color negative films, since the time necessitated therefor is longer than that necessitated for processing color papers.

For the reduction of the time necessitated for the color development step in the processing steps, J. P. KOKAI No. Hei 4-45440 discloses a method wherein tetrahydroquinoline or a dihydroindole derivative is used as the color developing agent. The use of such a compound as the color developing agent is also described in U.S. Pat. Nos. 2,196,739 and 2,566,259. In particular, it is described in J. P. KOKAI No. Hei 4-45440 that the time necessitating for the color developing step can be reduced by using such a compound as the color developing agent even in color photographic photosensitive materials mainly comprising a silver bromoiodide emulsion such as color negative films. Further, it is described in European Patent No. 670,312A1 that when at lease one of three carbon atoms forming the propylene chain of tetrahydroquinoline skeleton is free from hydrogen atom, the fog density is lowered.

However, it was found that the development of a photosensitive material for color photography with one of the compounds described in these specifications has some defects. Namely, since the image density in the unexposed part is high to cause a fog, the yellow and cyan image densities are insufficient as compared with the magenta image density in the exposed part, and the three-colors are not well balanced.

Polyethyleneoxy groups having two or more repeating units are not described in the description or in the examples of the compounds as a 4-N substituent of a tetrahydroquinoline compound or dihydroindole compound in the above-described J. P. KOKAI No. Hei 4-45440, U.S. Pat. Nos. 2,196,739 and 2,566,259 and European Patent No. 670,312A1. Not only in the compounds usable as the developing agent for silver halide color photographic materials but also in known 4-(N,N-dialkylamino)aniline compounds in which a 4-N substituent is capable of forming a condensed ring with a benzene ring such as the trahydroquinoline compounds and dihydroindole compounds, there are no compounds having a polyethyleneoxy group having two or more repeating units as N-substituent.

SUMMARY OF THE INVENTION

An object of the present invention is to provide 4-(N,N-dialkylamino)aniline compounds wherein the 4-N substituent forms a condensed ring with the benzene ring.

Another object of the present invention is to provide a color developing agent usable for silver halide color photographic materials.

Another object of the present invention is to provide a processing solution for silver halide color photographic photosensitive materials, which contains the developing agent.

Another object of the present invention is to provide a color image-forming method with the developing agent.

Another object of the present invention is to provide a color developing agent capable of having a low fog density and sufficient yellow and cyan image densities and suitable for the rapid process.

Another object of the present invention is to provide a processing composition containing the developing agent and useful for processing a silver halide color photographic photosensitive material.

Another object of the present invention is to provide a color image-forming method.

Another object of the invention is to provide a new compound expected for use as a starting material for dyes, medicines and agricultural chemicals.

These and other objects of the present invention will be apparent from the following description and examples.

The above-described problems have been solved by:
(1) aniline compounds represented by the following general formula (I):

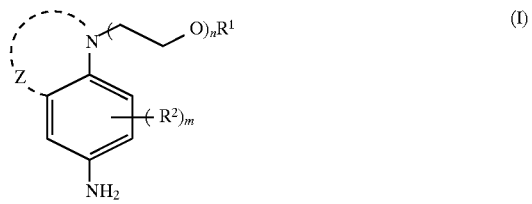

wherein $R^1$ represents a hydrogen atom or substituent, $R^2$ represents a substituent, Z represents a substituted or unsubstituted ethylene group or substituted or unsubstituted trimethylene group, n represents an integer of 2 to 8, and m represents 0 or an integer of 1 to 3, and when m is 2 or larger, $R^2$'s may be the same or different from each other, (2) a color photographic processing composition comprising at least one of the compounds described in item (1), and (3) a color image-forming method which comprises developing an image-exposed silver halide color photographic photosensitive material in the presence of at least one of the compounds described in item (1).

Although the compounds of the present invention are included in the claims of the above-described J. P. KOKAI No. Hei 4-45440 and European Patent No. 670,312A1, the specifications of them are completely silent on the specific compounds corresponding to the color developing agent of the present invention. Therefore, it is impossible to know the structure and properties of the compounds of the present invention from the specifications of them.

The 4-(N,N-dialkylamino)aniline compound in which the polyethyleneoxy group as the 4-N substituent forms a condensed ring with the benzene ring is expected to be usable as an intermediate for dyes for dyeing keratin fibers such as human hair and also as a starting material for medicines and agricultural chemicals.

DETAILED DESCRIPTION OF THE PREFERRED EMBODIMENTS

The detailed description will be made on the general formula (I).

$R^1$ represents a hydrogen atom or substituent having 1 to 20 carbon atoms, preferably 1 to 8 carbon atoms and more preferably 1 carbon atom. Examples of the substituents include alkyl group (preferably those having 1 to 15 carbon atoms such as methyl, ethyl, n-propyl, n-butyl, n-pentyl, n-hexyl, n-heptyl, n-octyl, n-dodecyl, n-pentadecyl, isopropyl, sec-butyl, isobutyl, t-butyl, 3-pentyl, 2-methylbutyl, isopentyl, 2-ethylhexyl, cyclopropyl, cyclobutyl, cyclopentyl, cyclohexylmethyl, t-pentyl and di-t-octyl groups), aryl groups (preferably those having 6 or 7 carbon atoms such as phenyl and m-hydroxyphenyl groups), heterocyclic groups (preferably 5-membered or 6-membered saturated or unsaturated heterocyclic groups having 1 to 5 carbon atoms and at least one oxygen, nitrogen or sulfur atom, such as 2-furyl, 2-thienyl, 2-pyrimidinyl, imidazolyl and pyrazolyl groups), alkoxycarbonyl groups (preferably those having 1 to 7 carbon atoms such as methoxycarbonyl and t-butoxycarbonyl groups), silyl groups (preferably those having 3 to 7 carbon atoms such as trimethylsilyl, isopropyldiethylsilyl and t-butyldimethylsilyl groups), aryloxycarbonyl groups (preferably those having 1 to 7 carbon atoms such as phenoxycarbonyl and 3-hydroxyphenoxycarbonyl groups) and acyl groups (preferably those having 1 to 7 carbon atoms such as acetyl, benzoyl and 4-hydroxybenzoyl groups).

$R^1$ is preferably that selected from among hydrogen atom, alkyl groups, aryl groups and heterocyclic groups. Among them, hydrogen atom or alkyl group is more preferred.

Preferred examples of $R^1$ include hydrogen atom, and methyl, ethyl, n-propyl, n-butyl, n-pentyl, phenyl, imidazolyl and pyrazolyl groups. Among them, hydrogen atom and alkyl group having 1 to 3 carbon atoms (in particular, methyl, ethyl and n-propyl groups) are more preferred. Hydrogen atom and methyl groups are particularly preferred.

$R^2$ represents a substituent having 0 to 20 carbon atoms, preferably 0 to 8 carbon atoms, more preferably 1 to 8 carbon atoms, most preferably 1 to 3 carbon atoms. Examples of the substituents include hydroxyl group, halogen atoms (such as fluorine and chlorine atoms), alkyl groups (preferably those having 1 to 8 carbon atoms such as methyl, ethyl, n-propyl, i-propyl, n-butyl, t-butyl, t-pentyl, di-t-octyl, hydroxymethyl and 1,3-dihydroxy-2-propyl groups), aryl groups (preferably those having 6 or 7 carbon atoms such as phenyl and m-hydroxyphenyl groups), heterocyclic groups (preferably 5-membered or 6-membered saturated or unsaturated heterocyclic groups having 1 to 5 carbon atoms and at least one oxygen, nitrogen or sulfur atom, such as 2-furyl, 2-thienyl, 2-pyrimidinyl, imidazolyl and pyrazolyl groups), alkoxy groups (preferably those having 1 to 8 carbon atoms such as methoxy, ethoxy, i-propoxy, 2-hydroxyethoxy, 2-methanesulfonylethoxy, 2-(2-hydroxyethoxy)ethoxy and 2-[2-(2-hydroxyethoxy) ethoxy]ethoxy groups}, aryloxy groups (preferably those having 6 or 7 carbon atoms such as phenoxy and p-hydroxyphenoxy groups), carboxyl group, acylamino groups (preferably those having 1 to 7 carbon atoms such as acetamido, 2-methoxypropionamido and p-hydroxybenzoylamido groups), alkylamino groups (preferably those having 1 to 7 carbon atoms such as dimethylamino, diethylamino and 2-hydroxyethylamino groups), anilino groups (preferably those having 6 or 7 carbon atoms such as anilino, m-nitroanilino and m-hydroxyanilino groups), ureido groups (preferably those having 1 to 7 carbon atoms such as ureido, methylureido, N,N-dimethylureido and 2-methanesulfonamidoethylureido groups), sulfamoylamino groups (preferably those having 0 to 7 carbon atoms such as dimethylsulfamoylamino, methylsulfamoylamino and 2-methoxyethylsulfamoylamino groups), alkylthio groups (preferably those having 1 to 7 carbon atoms such as methylthio, ethylthio and benzylthio groups), arylthio groups (preferably those having 6 or 7 carbon atoms such as phenylthio, 2-carboxyphenylthio and 4-hydroxyphenylthio groups), alkoxycarbonylamino groups (preferably those having 2 to 7 carbon atoms such as methoxycarbonylamino, ethoxycarbonylamino and 3-methanesulfonylpropoxycarbonylamino groups), sulfonylamino groups (preferably those having 1 to 7 carbon atoms such as methanesulfonamido, p-toluenesulfonamido and 2-methoxyethanesulfonamido groups), carbamoyl groups (preferably those having 1 to 7 carbon atoms such as carbamoyl, N,N-dimethylcarbamoyl and N-ethylcarbamoyl groups), sulfamoyl groups (preferably those having 0 to 7 carbon atoms such as sulfamoyl, dimethylsulfamoyl and ethylsulfamoyl groups), sulfonyl groups (preferably aliphatic sulfonyl groups having 1 to 5 carbon atoms and aromatic sulfonyl groups having 6 or 7 carbon atoms such as methanesulfonyl, ethanesulfonyl and 2-chloroethanesulfonyl groups), alkoxycarbonyl groups (preferably those having 1 to 7 carbon atoms such as methoxycarbonyl and t-butoxycarbonyl groups), heterocyclic oxy groups (preferably five-membered or six-membered, saturated or unsaturated heterocyclic oxy groups having 1 to 5 carbon atoms and at least one oxygen, nitrogen or sulfur atom, wherein the number of the hetero atom and the variety of the element constituting the ring may be one or more, such as 1-phenyltetrazole-5-yl-oxy, 2-tetrahydropyranyloxy and 2-pyridyloxy groups), azo groups (preferably those having 1 to 7 carbon atoms such as phenylazo, 2-hydroxyphenylazo and 4-sulfophenylazo groups), acyloxy groups (preferably those having 1 to 7 carbon atoms such as acetoxy, benzoyloxy and 4-hydroxybutanoyloxy groups), carbamoyloxy groups (preferably those having 1 to 7 carbon atoms such as N,N-dimethylcarbamoyloxy, N-methylcarbamoyloxy and N-phenylcarbamoyloxy groups), silyl groups (preferably those having 3 to 7 carbon atoms such as trimethylsilyl, isopropyldiethylsilyl and t-butyldimethylsilyl groups), silyloxy groups (preferably those having 3 to 7 carbon atoms such as trimethylsilyloxy and triethylsilyloxy groups), aryloxycarbonylamino groups (preferably those having 7 carbon atoms such as phenoxycarbonylamino and 4-hydroxyphenoxycarbonylamino groups), imido groups (preferably those having 4 to 7 carbon atoms such as N-succinimido group), heterocyclic thio groups (five-membered or six-membered, saturated or unsaturated heterocyclic thio groups having 1 to 5 carbon atoms and at least one of oxygen, nitrogen and sulfur atoms, wherein the number of the hetero atom and variety of the element constituting the ring may be one or more, such as 2-benzothiazolylthio and 2-pyridylthio groups), sulfinyl groups (preferably those having 1 to 7 carbon atoms such as methanesulfinyl, benzenesulfinyl and ethanesulfinyl groups), phosphonyl groups (preferably those having 2 to 7 carbon atoms such as methoxyphosphonyl, ethoxyphosphonyl and phenoxyphosphonyl groups), aryloxycarbonyl groups (preferably those having 1 to 7 carbon atoms such as phenoxycarbonyl and 3-hydroxyphenoxycarbonyl groups), and acyl groups (preferably those having 1 to 7 carbon atoms such as acetyl, benzoyl and 4-hydroxybenzoyl groups).

$R^2$ is preferably a group selected from among alkyl, aryl, alkoxy, acylamino, ureido, sulfamoylamino, sulfonylamino, carbamoyl and sulfamoyl groups. Among them, alkyl, alkoxy, carbamoyl, sulfamoyl and ureido groups are preferred, and alkyl and alkoxy groups are particularly preferred.

Preferred examples of $R^2$ include methyl, ethyl, n-propyl, i-propyl, n-butyl, t-butyl, t-pentyl, di-t-octyl, hydroxymethyl, 1,3-dihydroxy-2-propyl, phenyl, m-hydroxyphenyl, methoxy, ethoxy, i-propoxy, 2-hydroxyethoxy, 2-methanesulfonylethoxy, 2-(2-hydroxyethoxy)ethoxy, 2-[2-(2-hydroxyethoxy)ethoxy] ethoxy), acetamido, 2-methoxypropionamido, p-hydroxybenzoylamido, ureido, methylureido, N,N-dimethylureido, 2-methanesulfonamidoethylureido, dimethylsulfamoylamino, methylsulfamoylamino, 2-methoxyethylsulfamoylamino, methanesulfonamido, p-toluenesulfonamido, 2-methoxyethanesulfonamido, carbamoyl, N,N-dimethylcarbamoyl, N-ethylcarbamoyl, sulfamoyl, dimethylsulfamoyl and ethylsulfamoyl groups. Among them, particularly preferred examples of $R^2$ are methyl, ethyl, n-propyl, i-propyl, t-butyl, methoxy, i-propoxy, acetamido, ureido, methylureido, N,N-dimethylureido, dimethylsulfamoylamino, methylsulfamoylamino, methanesulfonamido, carbamoyl, N,N-dimethylcarbamoyl, N-ethylcarbamoyl, sulfamoyl and dimethylsulfamoyl groups. Among them, an alkyl and alkoxy groups having 1 to 3 carbon atoms (in particular, methyl, ethyl, i-propyl, methoxy and i-propoxy groups) are the best.

Z represents a substituted or unsubstituted ethylene chain or trimethylene chain having 2 to 20 carbon atoms, preferably 2 to 10 carbon atoms and more preferably 2 to 6 carbon atoms. The substituents are those in the range described above with reference to $R^2$. Preferred substituents include hydroxyl group, halogen atoms, and alkyl, alkoxy, carboxy, acylamino, alkylamino, ureido, sulfamoylamino, alkoxycarbonylamino, sulfonylamino, carbamoyl, sulfamoyl, sulfonyl, alkoxycarbonyl, acyloxy, carbamoyloxy and acyl groups. Among them, particularly preferred substituents are hydroxyl, alkyl, carboxyl, acylamino, ureido, alkoxycarbonylamino, sulfonylamino, carbamoyl, acyloxy and carbamoyloxy groups. Among them, hydroxy, alkyl and carboxyl groups are more preferable. Examples of Z include groups, in which the carbon atom bonded to the nitrogen atom is in 1-position, such as ethylene, 1-methylethylene, 2-methylethylene, 1,2-dimethylethylene, 1,1,2-trimethylethylene, 1,2,2-trimethylethylene, 1,1,2,2-tetramethylethylene, 2-hydroxymethylethylene, 2-hydroxyethylene, 1-methyl-2-hydroxyethylene, 1,1,2-trimethyl-2-carboxyethylene, 1,1,2,2-tetraethylethylene, trimethylene, 1,1-dimethyltrimethylene, 2,2-dimethyltrimethylene, 3,3-dimethyltrimethylene, 1,1,3-trimethyltrimethylene, 1,1,3-trimethyl-2-decyltrimethylene, 1,1,3-triethyl-2-methyltrimethylene, 1,1-diethyltrimethylene, 2,2-diethyltrimethylene, 3,3-diethyltrimethylene, 1,1,2,2,3,3-hexaethyltrimethylene, 1,1,3-trimethyl-3-carboxytrimethylene, 1,1,3-trimethyl-2-hydroxytrimethylene, 1,1-dimethyl-2-hydroxy-3-methylidenetrimethylene, 1,1,3-trimethyl-2,3-dihydroxytrimethylene, 1,1,3-trimethyl-2-aminotrimethylene, 1,1,3-trimethyl-2-dimethylaminotrimethylene, 1,1,3-trimethyl-2-bromotrimethylene, 1,1,3-trimethyl-2-(N-pyrazolyl) trimethylene, 1,1-dihydroxymethyl-3-methyltrimethylene, 1,1-dimethyl-3-hydroxymethyltrimethylene, 1,1-dimethyl-3-formyltrimethylene, 1,1-dimethyl-3-carboxytrimethylene, 1,1-dimethyl-3-carbamoyltrimethylene, 1,1-dimethyl-3-dimethylcarbamoyltrimethylene, 1,1-dimethyl-3-hydroxymethyl-2,3-dihydroxytrimethylene and 1,1-dimethyl-3-hydroxymethyl-2-hydroxytrimethylene. Among them, preferred examples include ethylene, 1-methylethylene, 2-methylethylene, 1,2-dimethylethylene, 1,2,2-trimethylethylene, 1,1,2,2-tetramethylethylene, 2-hydroxyethylene, 1-methyl-2-hydroxyethylene, 1,1-dimethyltrimethylene, 2,2-dimethyltrimethylene, 3,3-dimethyltrimethylene, 1,1,3-trimethyltrimethylene, 1,1,3-triethyl-2-methyltrimethylene, 1,1,3-trimethyl-2-hydroxytrimethylene, 1,1,3-trimethyl-2,3-dihydroxytrimethylene, 1,1-dimethyl-3-hydroxymethyltrimethylene and 1,1-dimethyl-3-hydroxymethyl-2-hydroxytrimethylene. Among them, particularly preferred examples include ethylene, 1-methylethylene, 2-methylethylene, 1,2-dimethylethylene, 1,1-dimethyltrimethylene, 2,2-dimethyltrimethylene, 3,3-dimethyltrimethylene, 1,1,3-trimethyltrimethylene, 1,1,3-trimethyl-2-hydroxytrimethylene and 1,1-dimethyl-3-hydroxymethyltrimethylene.

It is preferable that n represents 2 to 5.

In a preferred combination of $R^1$, $R^2$, Z, n and m, $R^1$ represents a hydrogen atom or alkyl group, $R^2$ represents an alkyl or alkoxyl group, Z represents an ethylene chain or trimethylene chain, which may be unsubstituted or substituted with a hydroxyl, alkyl or carboxyl group, and which has 2 to 6 carbon atoms, n is an integer of 2 to 5 and m is 0 or 1.

The most preferred compounds are represented by the following general formula (I-a):

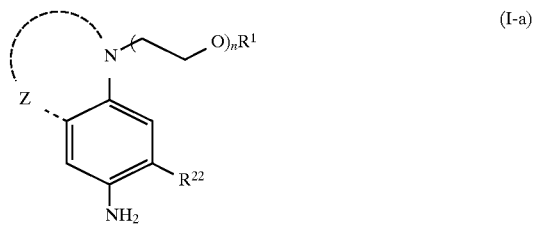

wherein $R^1$ represents a hydrogen atom or alkyl group having 1 to 3 carbon atoms, $R^{22}$ represents a hydrogen atom, alkyl or alkoxy group having 1 to 3 carbon atoms, Z represents a substituted or unsubstituted ethylene group or substituted or unsubstituted trimethylene group, each group of which has 2 to 6 carbon atoms wherein a substituent in the substituted ethylene group or substituted trimethylene group is selected from the group consisting of hydroxyl, alkyl and carboxyl groups, and n represents an integer of 2 to 5.

Examples of the compounds represented by the general formula (I) of the present invention are given below, which by no means limit the invention.

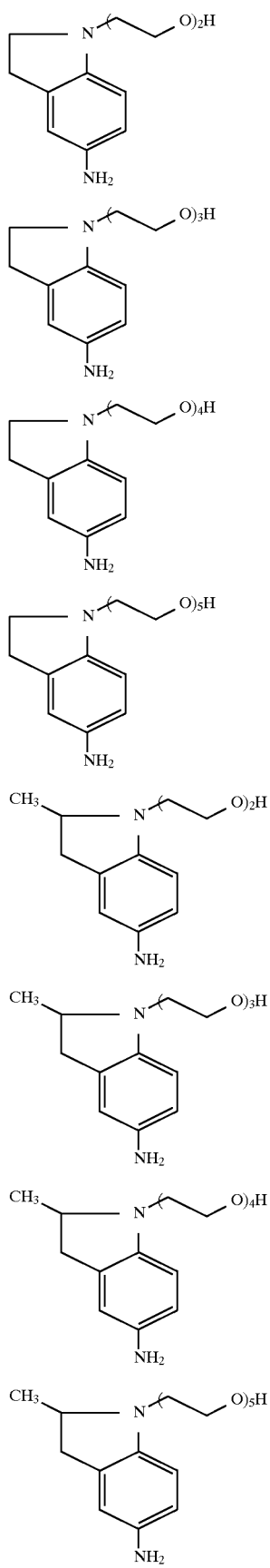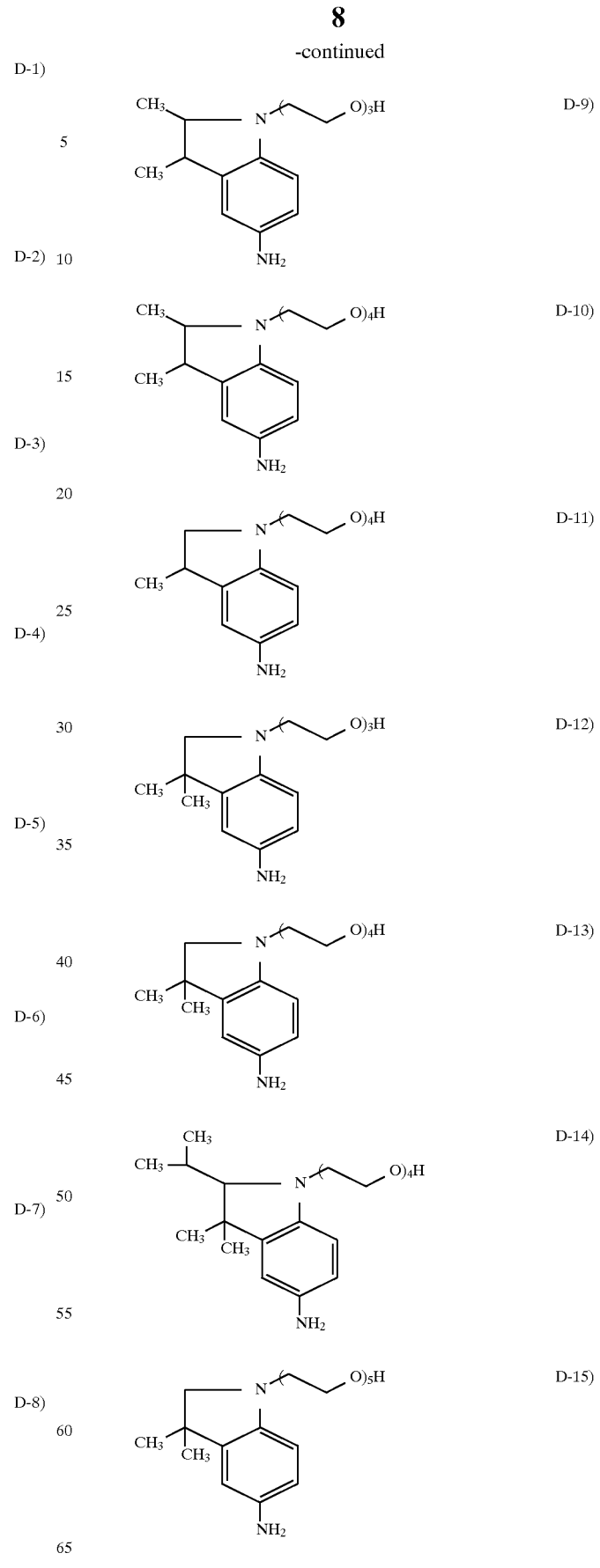

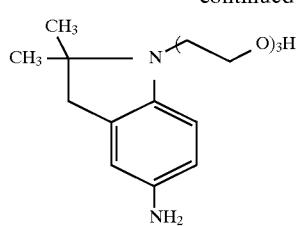 D-16)
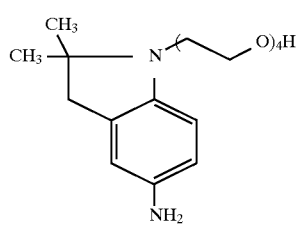 D-17)
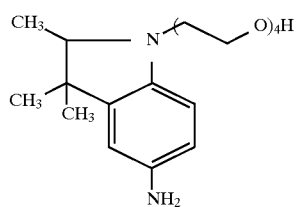 D-18)
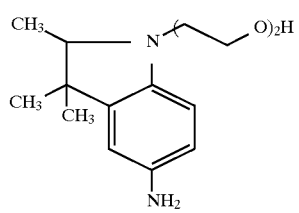 D-19)
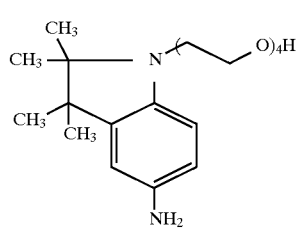 D-20)
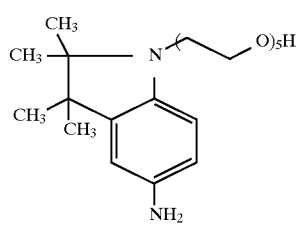 D-21)
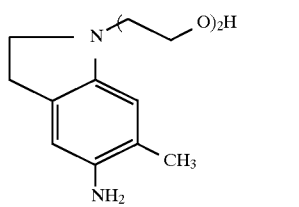 D-22)
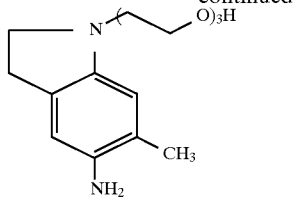 D-23)
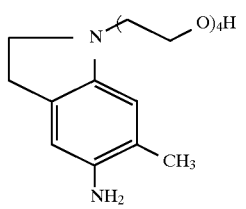 D-24)
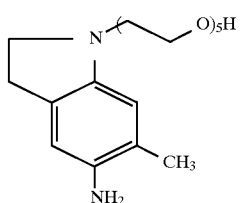 D-25)
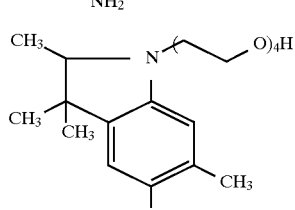 D-26)
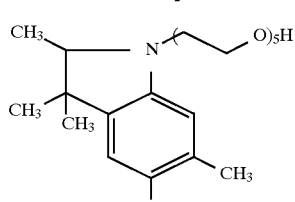 D-27)
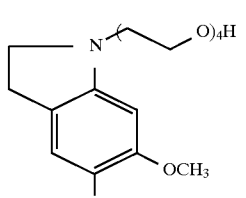 D-28)
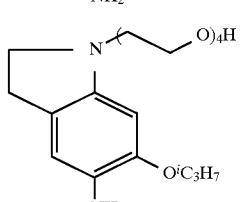 D-29)
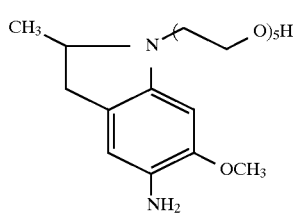 D-30)

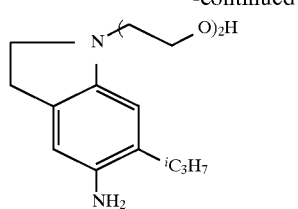 D-31)
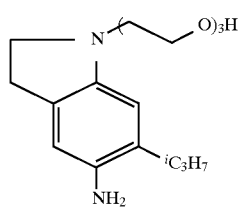 D-32)
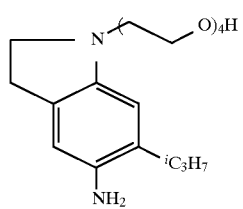 D-33)
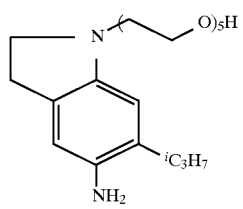 D-34)
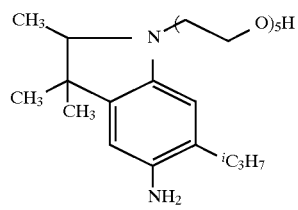 D-35)
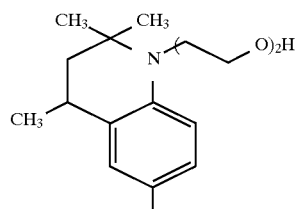 D-36)
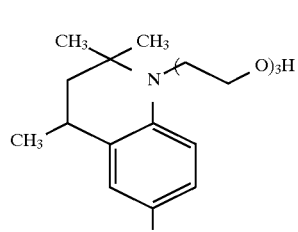 D-37)
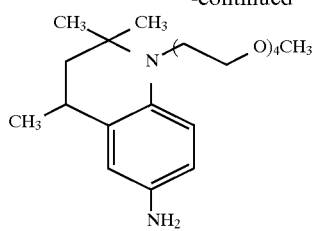 D-38)
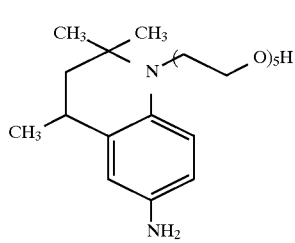 D-39)
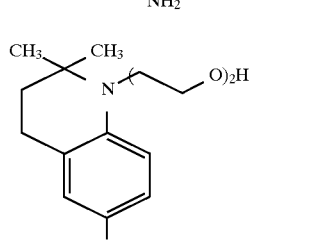 D-40)
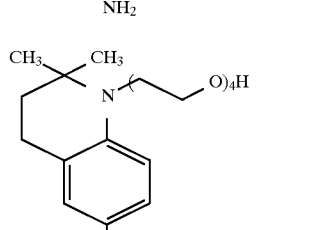 D-41)
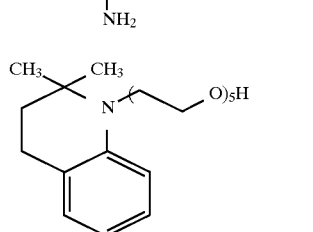 D-42)
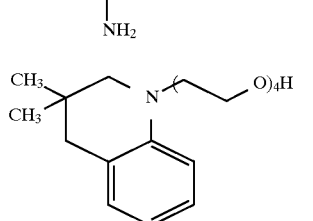 D-43)
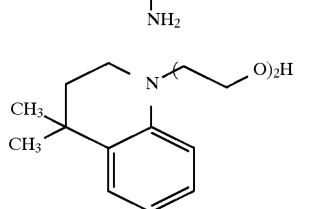 D-44)

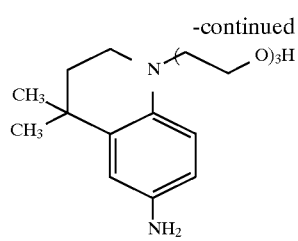
D-45)
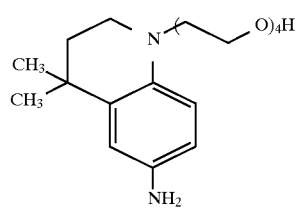
D-46)
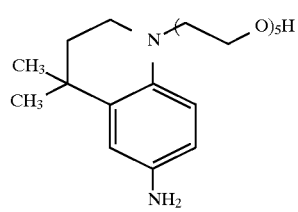
D-47)
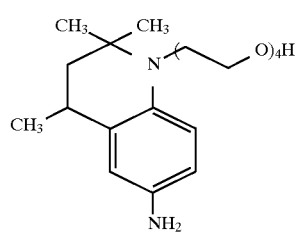
D-48)
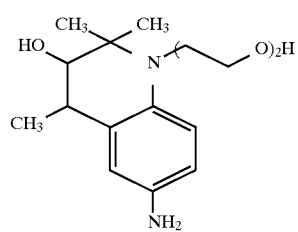
D-49)
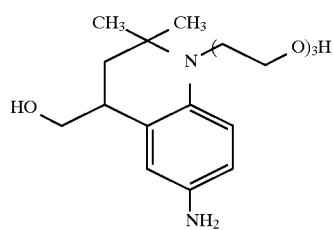
D-50)
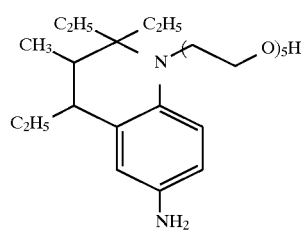
D-51)
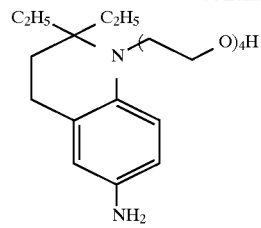
D-52)
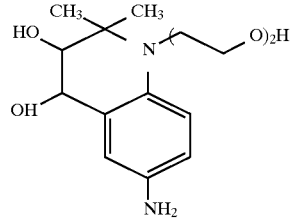
D-53)
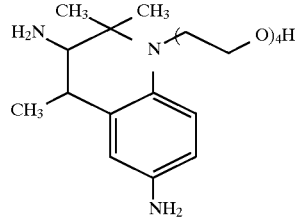
D-54)
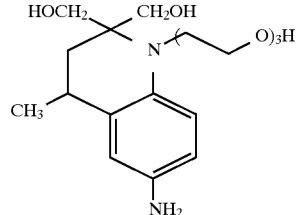
D-55)
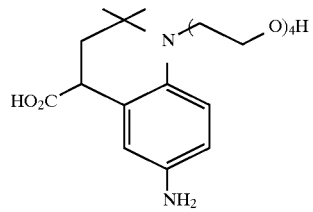
D-56)
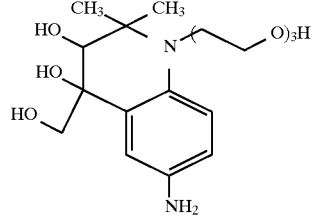
D-57)
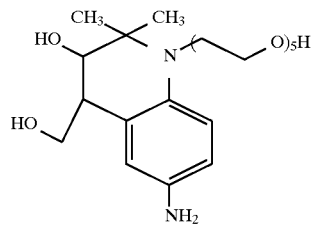
D-58)

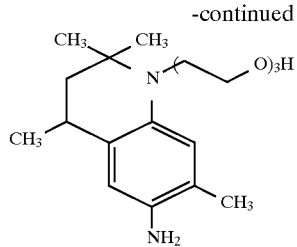 D-59)
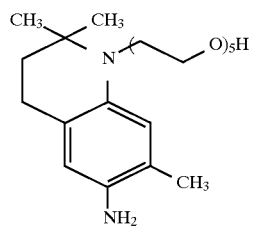 D-60)
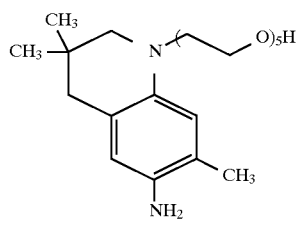 D-61)
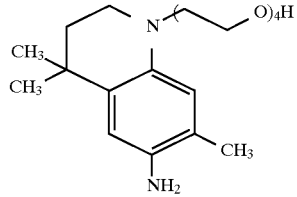 D-62)
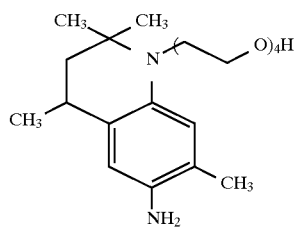 D-63)
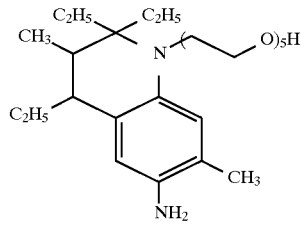 D-64)
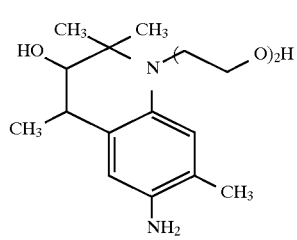 D-65)
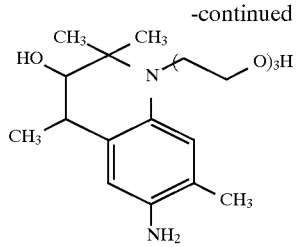 D-66)
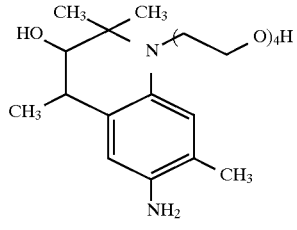 D-67)
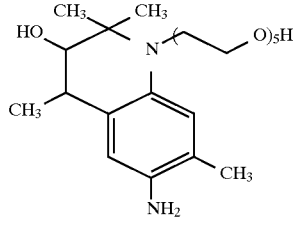 D-68)
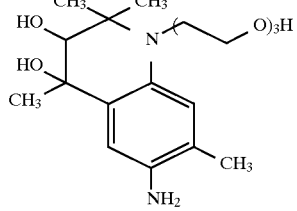 D-69)
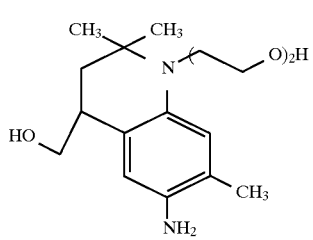 D-70)
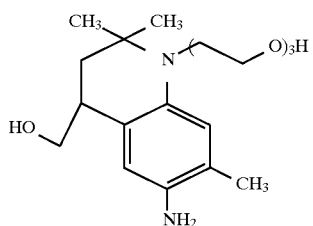 D-71)
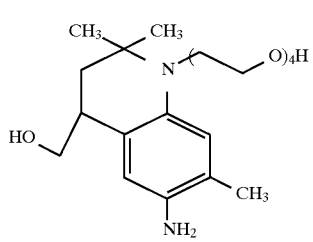 D-72)

-continued
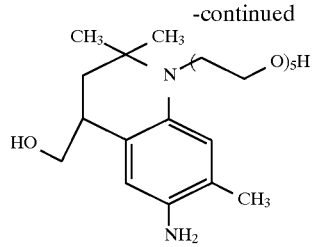 D-73)
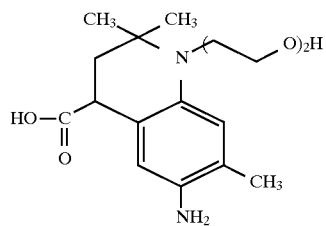 D-74)
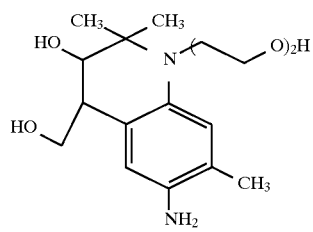 D-75)
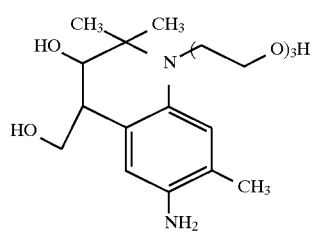 D-76)
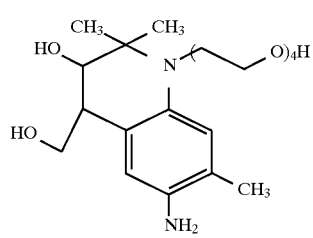 D-77)
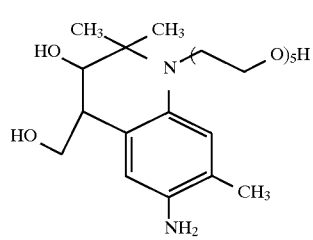 D-78)
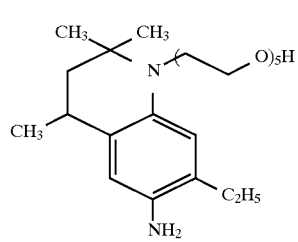 D-79)
-continued
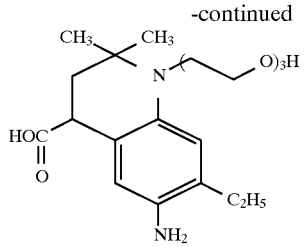 D-80)
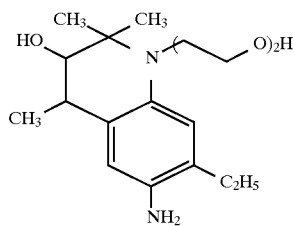 D-81)
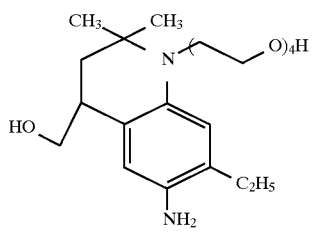 D-82)
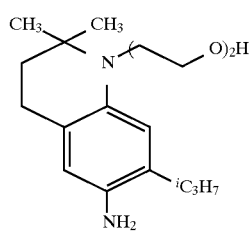 D-83)
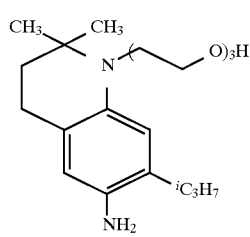 D-84)
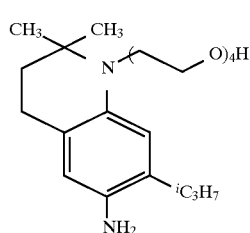 D-85)
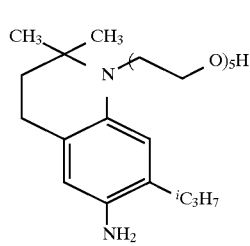 D-86)

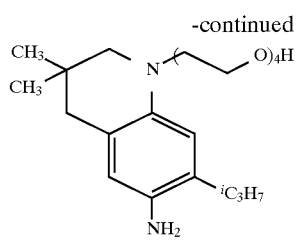 D-87)
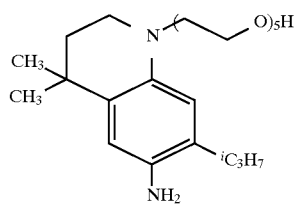 D-88)
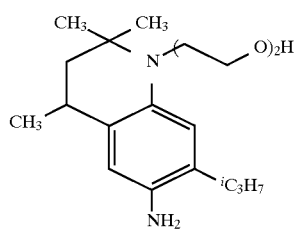 D-89)
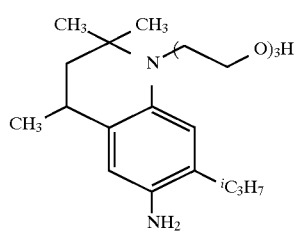 D-90)
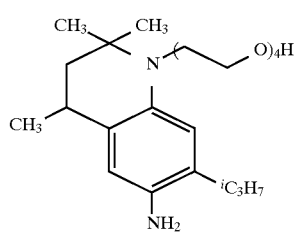 D-91)
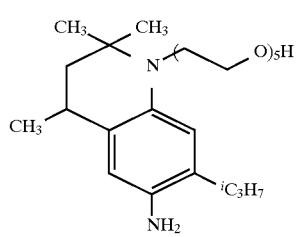 D-92)
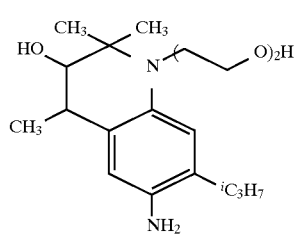 D-93)
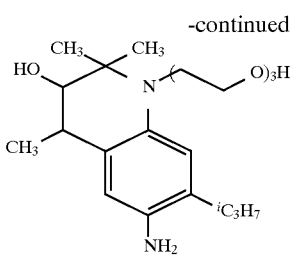 D-94)
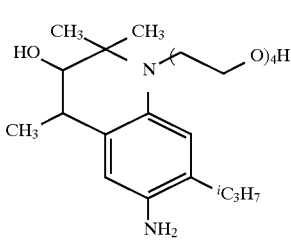 D-95)
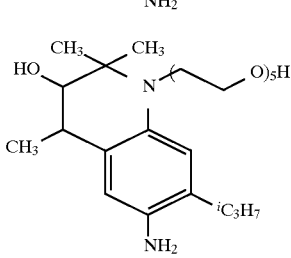 D-96)
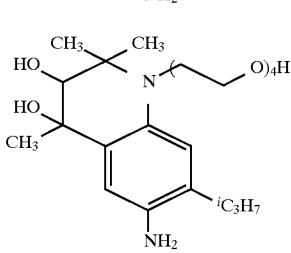 D-97)
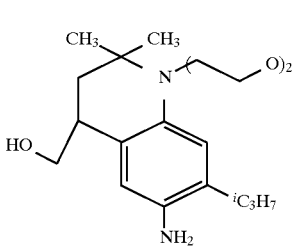 D-98)
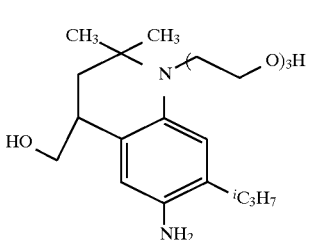 D-99)
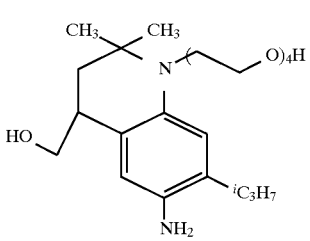 D-100)

-continued
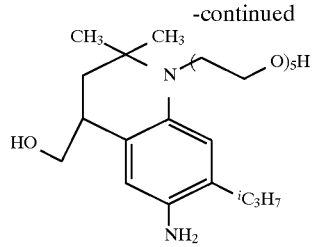 D-101)
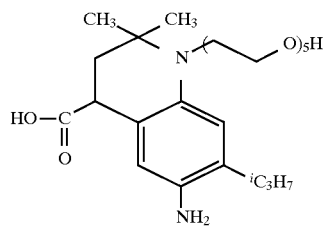 D-102)
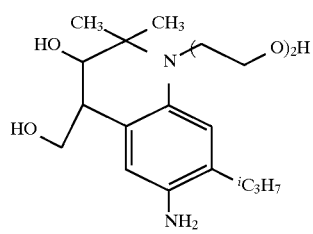 D-103)
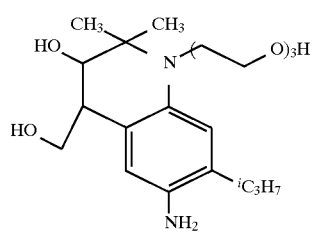 D-104)
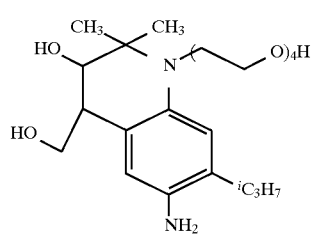 D-105)
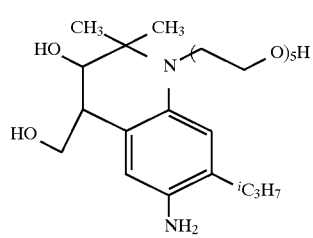 D-106)
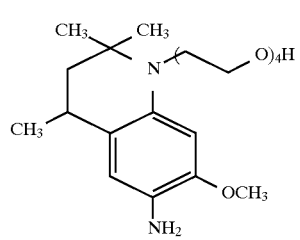 D-107)
-continued
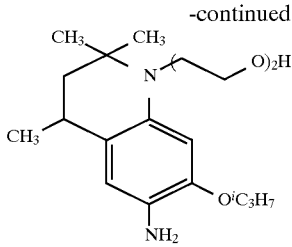 D-108)
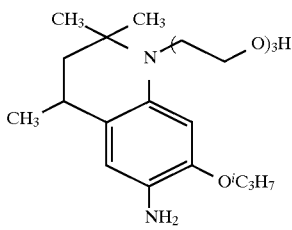 D-109)
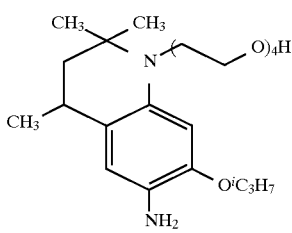 D-110)
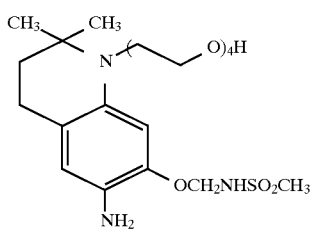 D-111)
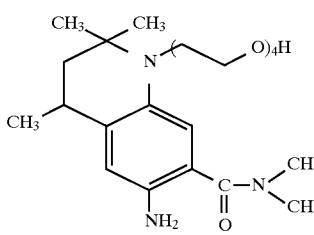 D-112)
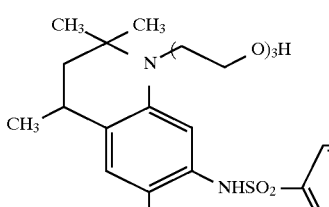 D-113)
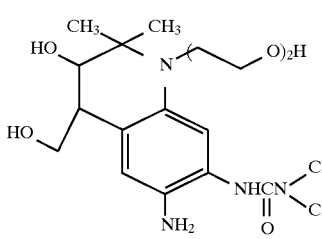 D-114)

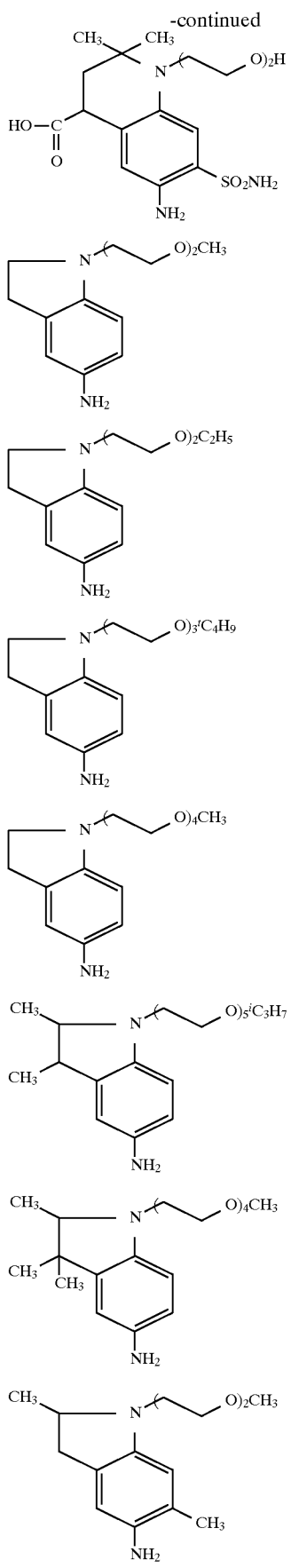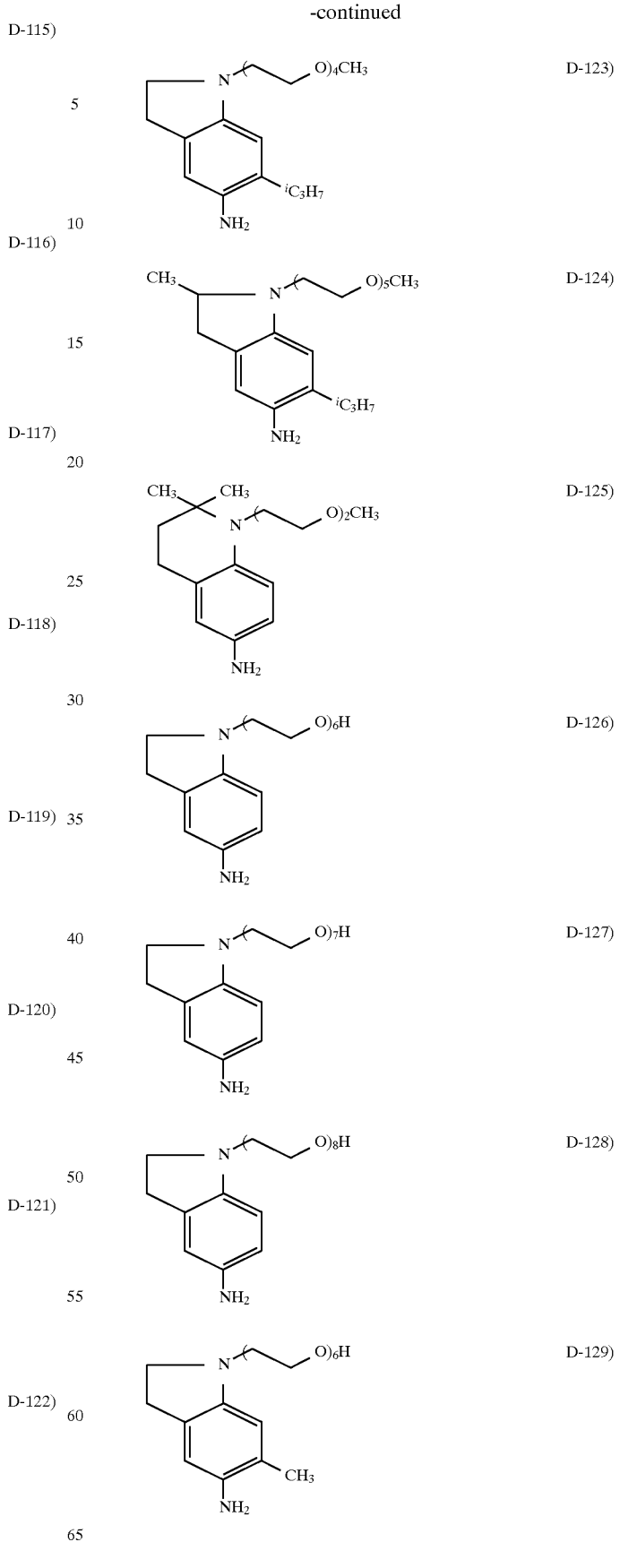

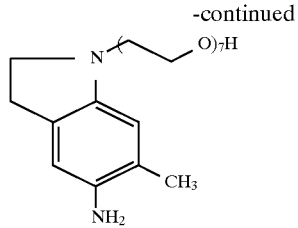 D-130)
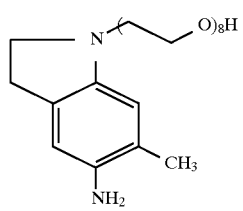 D-131)
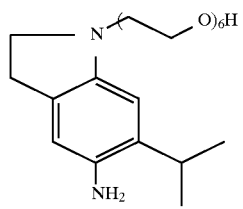 D-132)
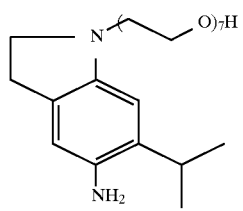 D-133)
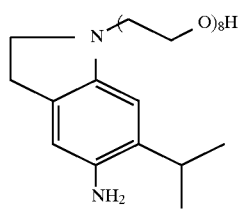 D-134)
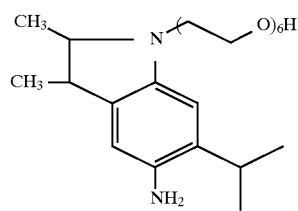 D-135)
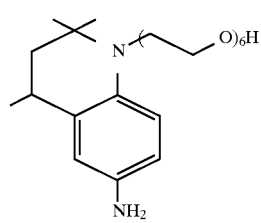 D-136)
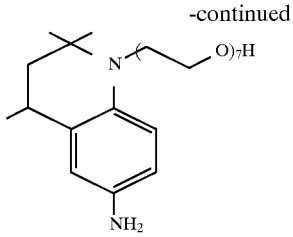 D-137)
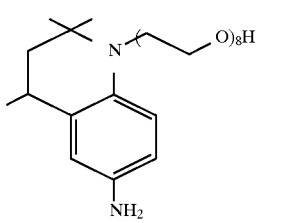 D-138)
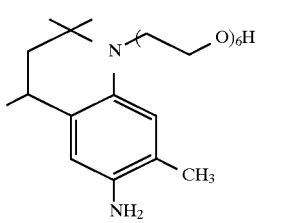 D-139)
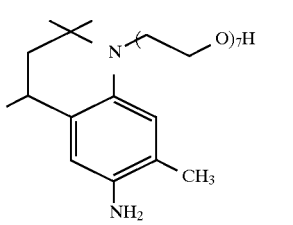 D-140)
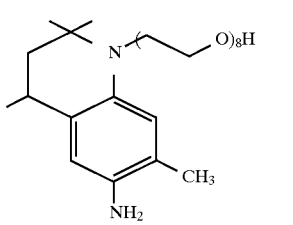 D-141)
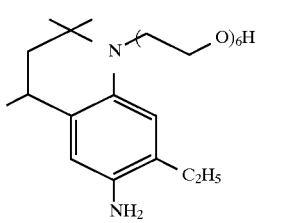 D-142)
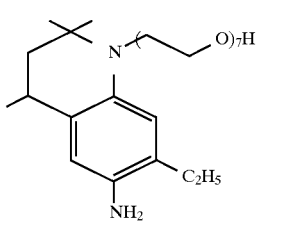 D-143)

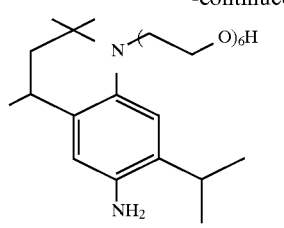 D-144)
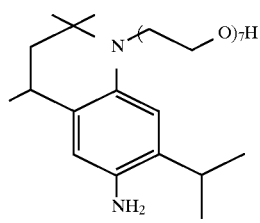 D-145)
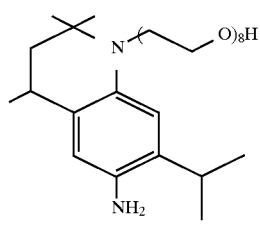 D-146)
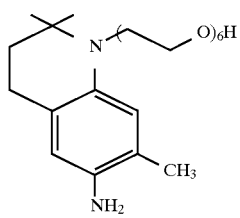 D-147)
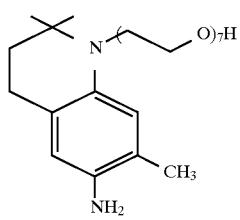 D-148)
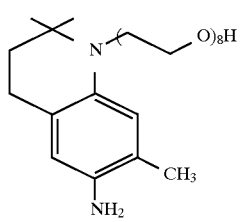 D-149)
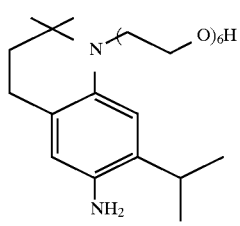 D-150)
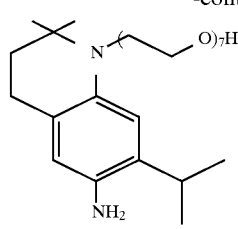 D-151)
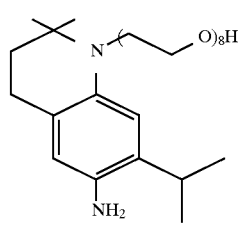 D-152)
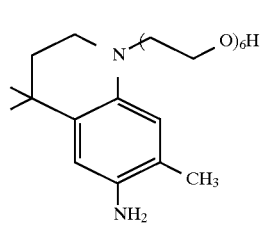 D-153)
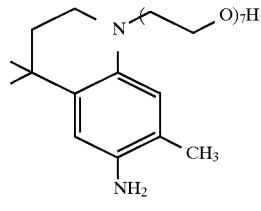 D-154)
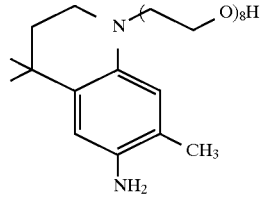 D-155)
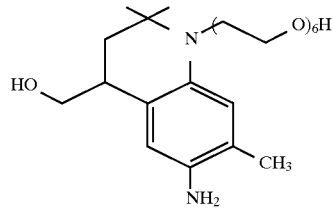 D-156)
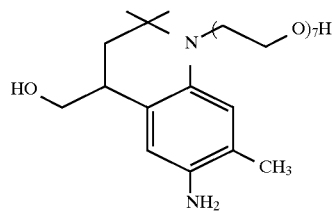 D-157)

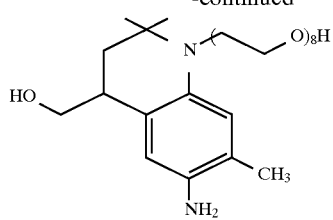
D-158)

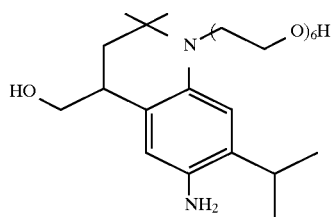
D-159)

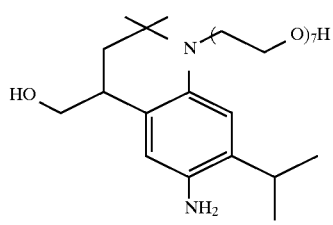
D-160)

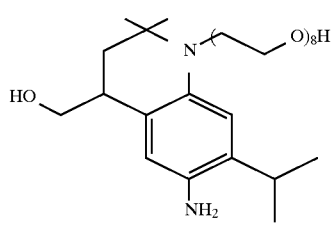
D-161)

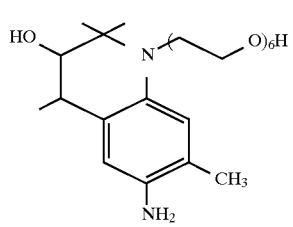
D-162)

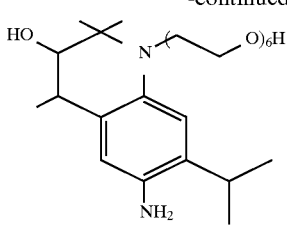
D-163)

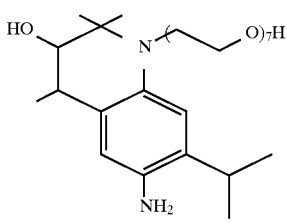
D-164)

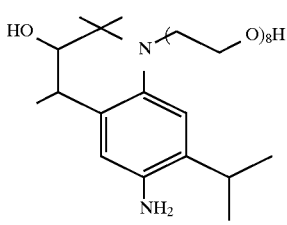
D-165)

Since the compounds of the general formula (I) are very unstable when they are stored in the form of the free amines, they are usually produced and stored in the form of salts thereof with an inorganic or organic acid, and they are converted into the free amines when they are to be used or, in particular, when they are to be added to the processing solution. The inorganic and organic acids used for forming the salts with the compounds of the general formula (I) include, for example, hydrochloric acid, sulfuric acid, phoshoric acid, p-toluenesulfonic acid, methanesulfonic acid and naphthalene-1,5-disulfonic acid. Among these salts, salts with sulfuric acid, p-toluenesulfonic acid or naphthalene-1,5-disulfonic acid are preferred. The salts with sulfuric acid is the most desirable.

The 4-(N,N-dialkylamino)aniline compounds can be synthesized according to a method described in, for example, Journal of the American Chemical Society, Vol. 73, p. 3100 (1951). They can be synthesized also by synthesizing methods which will be described below and so on.

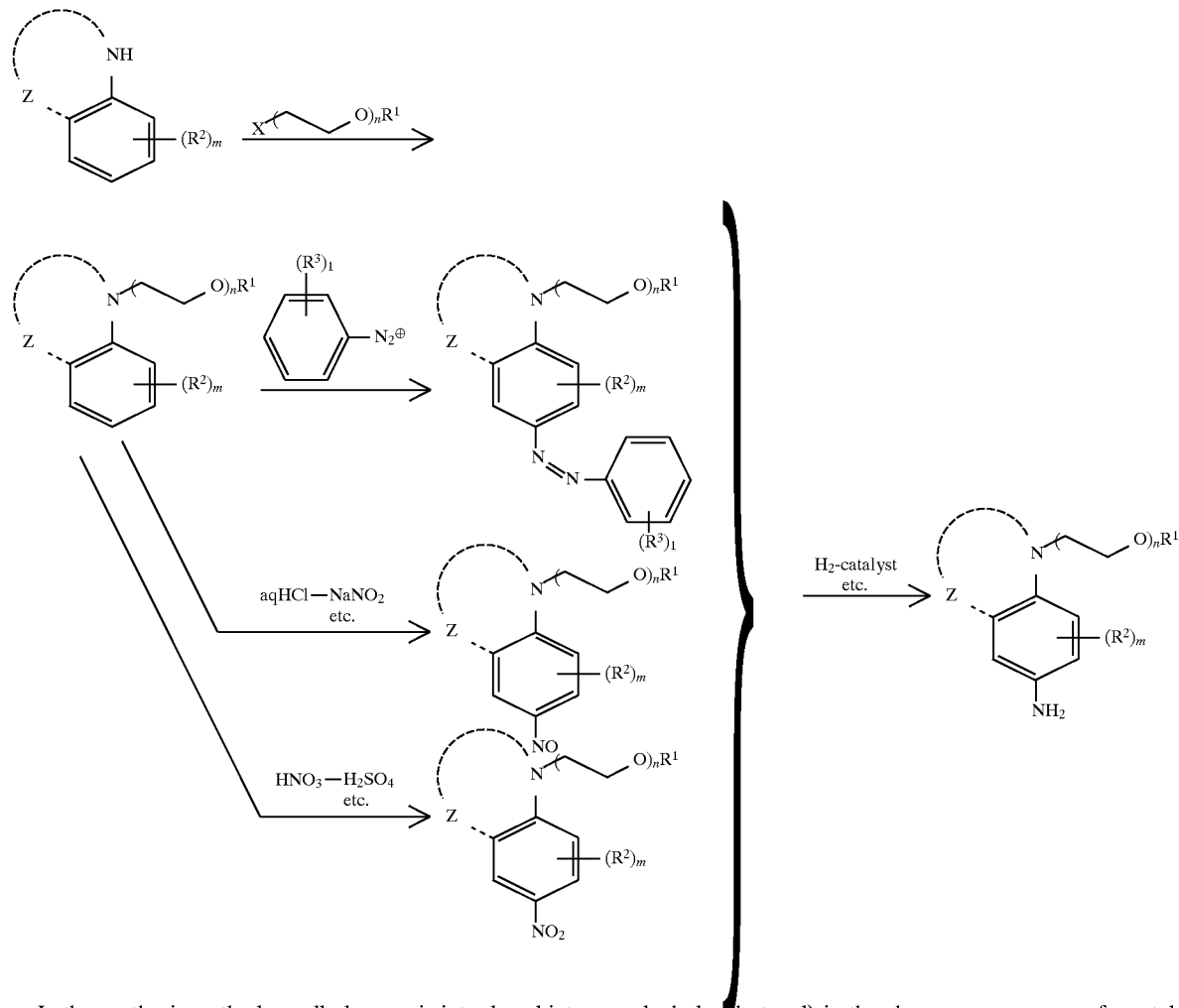

In the synthesis method, an alkyl group is introduced into the amino group of aniline forming the condensed ring with benzene. In particular, a polyethyleneoxy group is introduced thereinto at first by the reaction with a polyethyleneoxy group-containing halide, or a polyethyleneoxy group-containing alkyl or aryl-sulfonate. Then, the azo coupling reaction in the p-position of the amino group is conducted or a nitroso or nitro group is introduced thereinto, and the obtained product is reduced by catalytic hydrogenation, reduction with zinc under acidic conditions or reduction with reducing iron to obtain the intended product.

In the alkylation reaction, for example, 1 to 5 equivalents, preferably 1 to 3 equivalents, of an alkyl halide (chloride, bromide or iodide), alkyl sulfonate (mesylate, tosylate or the like) or alkyl ester (acetate, benzoate or the like) is used as the alkylating agent for alkylating one equivalent of the compound; 1 to 5 equivalents, preferably 1 to 3 equivalents, of an organic base (such as triethylamine or diazabicycloundecene) or inorganic base (such as sodium hydrogencarbonate, sodium carbonate, potassium carbonate, sodium hydroxide or potassium hydroxide) is used for alkylating one equivalent of the compound; and the reaction is carried out without using any solvent or in a solvent such as an amide solvent (e. g. N,N-dimethylacetamide, N,N-dimethylformamide or 1-methyl-2-pyrrolidone), sulfone solvent (e. g. sulfolane), sulfoxide solvent (e. g. dimethyl sulfoxide), ureide solvent (e. g. tetramethylurea), ether solvent (e. g. dioxane) or alcohol solvent (e. g. isopropyl alcohol or butanol) in the absence or presence of a catalyst (e. g. sodium iodide) at a reaction temperature in the range of 0° to 200° C., preferably 80° to 170° C. for a reaction time in the range of 10 minutes to 72 hours, preferably 30 minutes to 12 hours.

Then, azo coupling is conducted in the p-position of the amino group, or a nitroso group or nitro group is introduced thereinto. The azo coupling is conducted by, for example, converting unsubstituted or substituted aniline into a diazonium salt thereof in the presence of an acid (an inorganic or organic acid such as hydrochloric acid, sulfuric acid, methanesulfonic acid or acetic acid) without using any solvent or in water or an organic solvent (such as an alcohol solvent, e. g. methanol, ethanol or isopropyl alcohol; an amide solvent, e. g. N,N-dimethylacetamide, N,N-dimethylformamide or 1-methyl-2-pyrrolidone; a sulfone solvent, e. g. sulfolane; a sulfoxide solvent, e. g. dimethyl sulfoxide; or ureido solvent, e. g. tetramethylurea) at a reaction temperature in the range of −78° to 40° C., preferably −20° to 30° C. for a reaction time in the range of 5 minutes to 5 hours, preferably 5 minutes to 1 hour; and then coupling 1 to 5 equivalents, preferably 1 to 2 equivalents, of the obtained diazonium salt with an N,N-dialkylaniline in water or an organic solvent (such as an alcohol solvent, e. g. methanol, ethanol or isopropyl alcohol; amide solvent, e. g. N,N-dimethylacetamide, N,N-dimethylformamide or 1-methyl-2-pyrrolidone; sulfone solvent, e. g. sulfolane; sulfoxide solvent, e. g. dimethyl sulfoxide; or ureide solvent, e. g. tetramethylurea) at a reaction temperature in the range of −78° to 40° C., preferably −20° to 30° C. for a reaction time in the range of 5 minutes to 5 hours, preferably 5 minutes to 1 hour. The coupling reaction is conducted preferably under weakly acidic to weakly basic conditions. The nitrosation reaction is carried out by, for example, using 1 to 5 equivalents, preferably 1 to 2 equivalents, of an organic nitrosating agent (such as isoamyl nitrite) or inorganic nitrosating agent (such as sodium nitrite) in the presence of an acid (an inorganic or organic acid such as hydrochloric acid, sulfuric acid, methanesulfonic acid or acetic acid) without using any solvent or in water or an organic solvent (such as an alcohol solvent, e. g. methanol, ethanol or isopropyl alcohol; an amide solvent, e. g. N,N-dimethylacetamide, N,N-dimethylformamide or 1-methyl-2-pyrrolidone; a sulfone solvent, e. g. sulfolane; a sulfoxide solvent, e. g. dimethyl sulfoxide; or ureido solvent such as tetramethylurea) at a reaction temperature in the range of −78° to 40° C., preferably −20° to 30° C. for a reaction time in the range of 5 minutes to 5 hours, preferably 5 minutes to 1 hour. The nitration reaction is carried out by, for example, using 1 to 5 equivalents, preferably 1 to 1. 5 equivalents, of nitric acid in having a concentration in the range of 60 to 98% in the absence or presence of an activating agent selected from among sulfuric acid, sulfuric anhydride, acetic anhydride or trifluoroacetic anhydride without using any solvent or in water or an organic solvent (such as an alcohol solvent, e. g. methanol, ethanol or isopropyl alcohol; an organic acid, e. g. acetic acid; an organic acid anhyride, e. g. acetic anhydride or trifluoroacetic anhydride; amide solvent, e. g. N,N-dimethylacetamide, N,N-dimethylformamide or 1-methyl-2-pyrrolidone; a sulfone solvent, e. g. sulfolane; a sulfoxide solvent, e. g. dimethyl sulfoxide; or ureido solvent, e. g. tetramethylurea) at a reaction temperature in the range of −78° to 100° C., preferably −20° to 30° C. for a reaction time in the range of 5 minutes to 5 hours, preferably 5 minutes to 1 hour.

Finally, the reaction product is reduced by, for example, catalytic reduction with hydrogen, reduction with zinc under an acidic condition or reduction with reduced iron to obtain the intended product. For example, the catalyltic reaction with hydrogen is conducted in the presence of a catalyst (such as palladium/carbon or Raney nickel) without using any solvent or in water or an organic solvent (such as an alcohol solvent, e. g. methanol, ethanol or isopropyl alcohol; an amide solvent, e. g. N,N-dimethylacetamide, N,N-dimethylformamide or 1-methyl-2-pyrrolidone; a sulfone solvent, e. g. sulfolane; a sulfoxide solvent, e. g. dimethyl sulfoxide; or ureido solvent such as tetramethylurea) at a reaction temperature in the range of 0° to 150° C., preferably 0° to 50° C. under a hydrogen pressure in the range of 1 to 500 atm, preferably 1 to 200 atm for a reaction time in the range of 5 minutes to 72 hours, preferably 1 to 8 hours. The reduction with reduced iron is conducted by, for example, using 4 to 10 equivalents, preferably 4 to 6 equivalents, of reduced iron and 0.0001 to 1 equivalent, preferably 0.001 to 0.1 equivalent, of an acid (such as an inorganic acid, e. g. hydrochloric acid or sulfuric acid, or an organic acid, e. g. acetic acid or methanesulfonic acid) or an acid salt (such as ammonium chloride, sodium chloride or sodium sulfate) singly or in combination of two or more of them without using any solvent or in water or an organic solvent (such as an alcohol solvent, e. g. methanol, ethanol or isopropyl alcohol; an amide solvent, e. g. N,N-dimethylacetamide, N,N-dimethylformamide or 1-methyl-2-pyrrolidone; a sulfone solvent, e. g. sulfolane; a sulfoxide solvent, e. g. dimethyl sulfoxide; or ureide solvent, e. g. tetramethylurea) at a reaction temperature in the range of 0° to 150° C., preferably 50° to 100° C. for a reaction time in the range of 30 minutes to 72 hours, preferably 1 to 8 hours. The reduction with zinc under an acidic condition is conducted by, for example, using 3 to 10 equivalents, preferably 3 to 6 equivalents, of zinc powder in the presence of an acid (such as an organic acid, e. g. acetic acid or methanesulfonic acid, or an inorganic acid, e. g. hydrochloric acid or sulfuric acid) without using any solvent or in water or an organic solvent (such as an alcohol solvent, e. g. methanol, ethanol or isopropyl alcohol; an organic acid, e. g. acetic acid; an amide solvent e. g. N,N-dimethylacetamide, N,N-dimethylformamide or 1-methyl-2-pyrrolidone; a sulfone solvent, e. g. sulfolane; a sulfoxide solvent, e. g. dimethyl sulfoxide; ureide solvent, e. g. tetramethylurea; or an organic acid solvent, e. g. acetic acid, propionic acid or methanesulfonic acid) at a reaction temperature in the range of 0° to 150° C., preferably 0° to 100° C. for a reaction time in the range of 5 minutes to 72 hours, preferably 30 minutes to 3 hours.

The reaction product thus obtained is treated by an ordinary after-treatment method which is usually conducted after organic synthesis reactions, and then purified if necessary. Namely, the product isolated from the reaction system is used without the purification or after the purification by recrystallization, column chromatography or the like, or by a combination of such processes. Alternatively, the reaction product can be poured into water or ice after the completion of the reaction followed by the distillation of the reaction solvent or without the distillation, the product is then neutralized, if necessary, and purified, if necessary, by one or a combination of the recrystallization, column chromatography, etc. before the use. In another embodiment, the reaction solvent is distilled off, if necessary, after the completion of the reaction, the reaction product is poured into water or ice, then neutralized if necessary and extracted with an organic solvent, the obtained extract is purified, if necessary, by crystallization and/or column chromatography before use.

Synthesis Examples of anilines forming a condensed ring with benzene ring are given below.

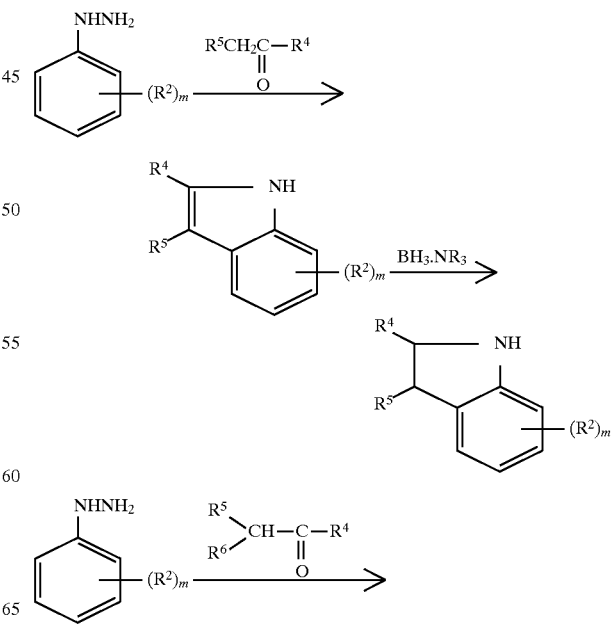

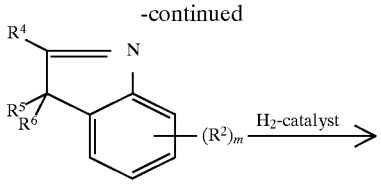

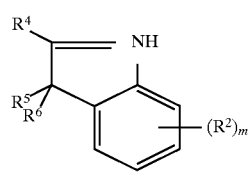

The dihydroindole skeleton can be obtained by Fischer's indole synthesis method from an arylhydrazine as shown above and then reducing the obtained indole compound or indolenine compound.

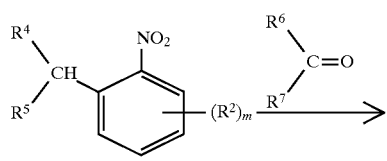

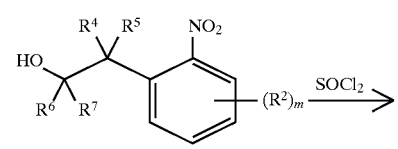

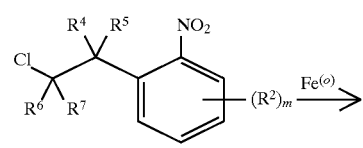

In another method, a hydroxymethyl group is introduced into the benzyl ring, this group is chlorinated and then a condensed ring is formed with the amino group in the 2-position of the benzene ring according to Journal of the Organic Chemistry, Vol. 55, p. 580 (1990).

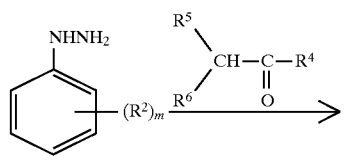

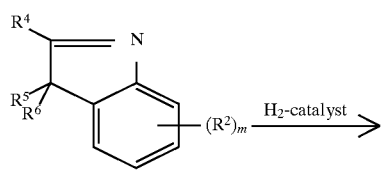

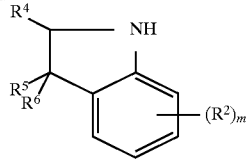

As for the formation of tetrahydroquinoline skeleton, 2,2,4-trimethyltetrahydroquinoline can be obtained by dehydration condensation of aniline with acetone followed by reduction of the product by a method described on page 328 of Organic Synthesis Collective Volume III.

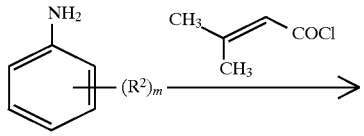

From N-allylaniline and zinc (II) chloride, a corresponding tetrahydroquinoline can be obtained by a method described in Journal of Japanese Chemical Society, p. 1043 (1981).

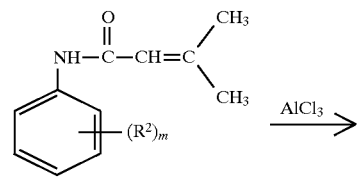

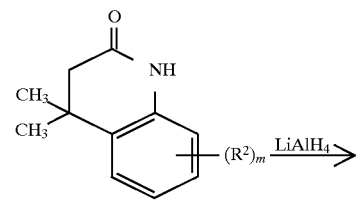

Further, such a compound can be obtained by Friedel-Crafts reaction of an α, β-unsaturated amide and the reduction of the amide by a method described in Journal of the American Chemical Society, Vol. 62, p. 778 (1940).

Thus, various substituents can be introduced into the propylene chain of the tetrahydroquinoline structure by using the intermediate material constituting the basic skeleton. Some examples are given below.
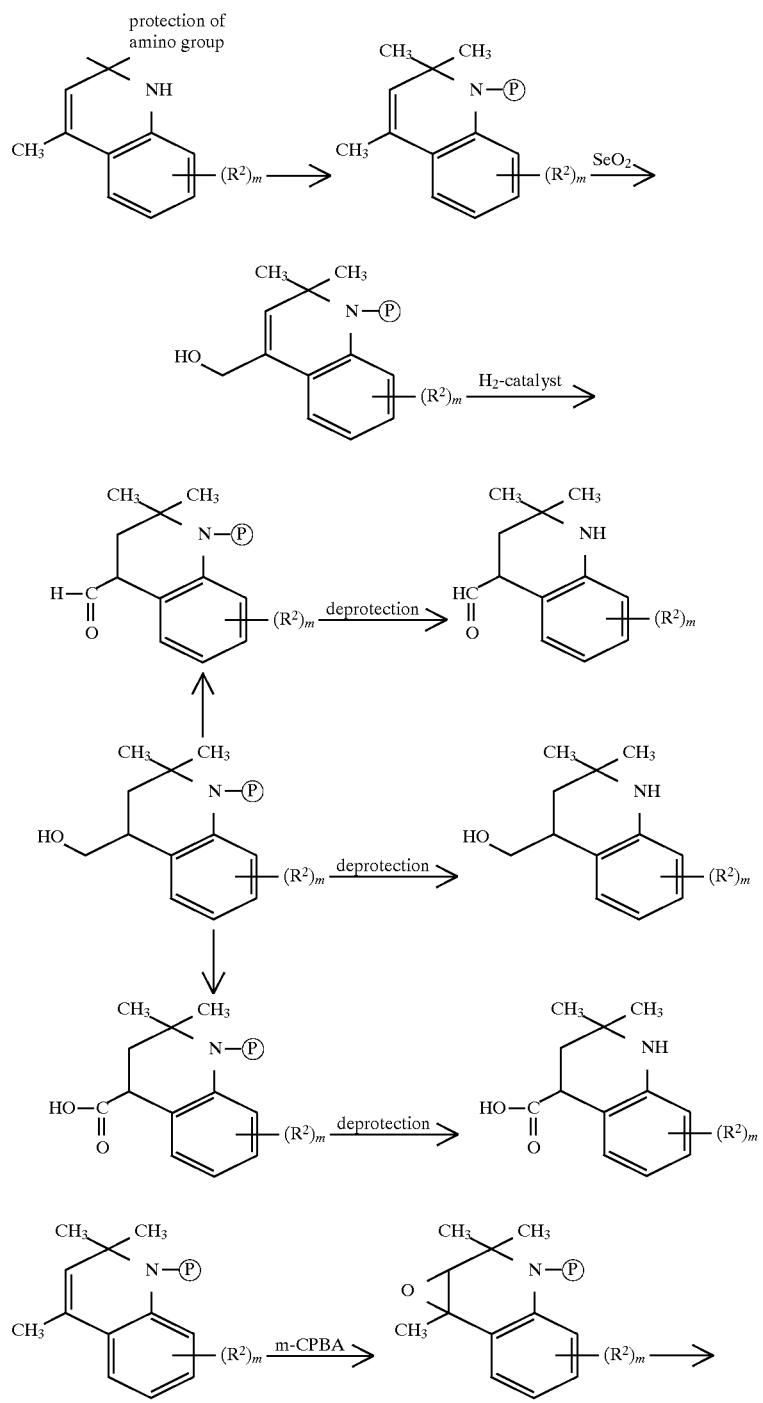

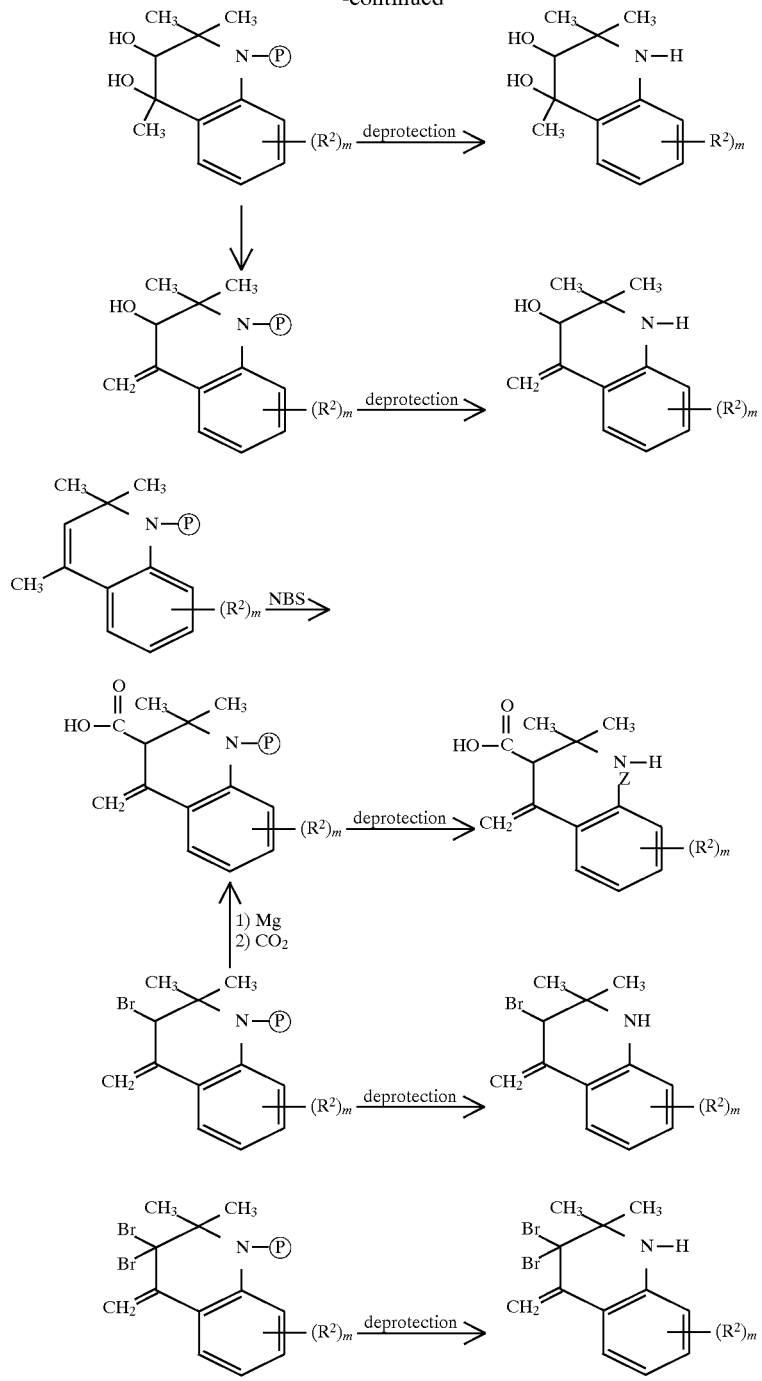

The description will be made on the use of the compounds of the present invention as color developing agent. The compound of the present invention can be used as the color developing agent either singly or in combination with other known p-phenylenediamine derivatives. Typical examples of the compounds usable in combination with the color developing agent include the following compounds, which by no means limit them: N,N-diethyl-p-phenylenediamine (P-1), 4-amino-3-methyl-N,N-diethylaniline (P-2), 4-amino-3-methyl-N-ethyl-N-(3-hydroxypropyl)aniline (P-3), 4-amino-N-ethyl-N-(2-hydroxyethyl)aniline (P-4), 4-amino-3-methyl-N-ethyl-N-(2-hydroxyethyl)aniline (P-5), 4-amino-3-methyl-N-ethyl-N-(2-methanesulfonamidoethyl)aniline (P-6), N-(2-amino-5-N,N-diethylaminophenylethyl)methane sulfonamide (P-7), N,N-dimethyl-p-phenylenediamine (P-8), 4-amino-3-methyl-N-ethyl-N-(2-methoxyethyl)aniline (P-9), 4-amino-3-methyl-N-ethyl-N-(4-hydroxybutyl) aniline (P-10), and 4-amino-3-methyl-N-ethyl-N-(2-butoxyethyl)aniline (P-11). Among the above-described p-phenylenediamine derivatives to be used for the combination, particularly preferred are compounds P-3, P-5, P-6 and P-10. The p-phenylenediamine derivatives are usually used in the form of their salts such as sulfates, hydrochlorides, sulfites, p-toluenesulfonates, nitrates and naphthalene-1,5-disulfonates.

The processing composition may be in liquid form or solid form (such as powdery, granular or tablet form).

These compounds are usable in combination of two or more of them depending on the purpose. The aromatic primary amine developing agent is used in an amount of preferably about 0.001 to 0.2 mol, more preferably 0.005 to 0.1 mol, per liter of the color developer.

In the color development with the compound of the present invention, this compound is incorporated into a processing solution or, alternatively, the compound or a precursor thereof is contained in a photosensitive material so that the compound is formed to exhibit its effect in the development process. In this case, the amount of the compound is 1 to 30 parts, preferably 1 to 10 parts, more preferably 1 to 4 parts, per part of the coupler.

The color developer may contain a compound for directly preserving the above-described aromatic primary amine color developing agent, which is selected from among hydroxylamines described in J.P. KOKAI Nos. Sho 63-5341, Sho 63-106655 and Hei 4-144446, hydroxamic acids described in J.P. KOKAI No. Sho 63-43138, hydrazines and hydrazides described in J.P. KOKAI No. Sho 63-146041, phenols described in J.P. KOKAI Nos. Sho 63-44657 and Sho 63-58443, α-hydroxyketones and α-aminoketones described in J.P. KOKAI No. Sho 63-44656, and saccharides described in J.P. KOKAI No. Sho 63-36244. Such a compound can be used in combination with monoamines described in J.P. KOKAI Nos. Sho 63-4235, 63-24254, 63-21647, 63-146040, 63-27841 and 63-25654, diamines described in J.P. KOKAI Nos. Sho 63-30845, 63-14640 and 63-43139, polyamines described in J.P. KOKAI Nos. Sho 63-21647, 63-26655 and 63-44655, nitroxy radicals described in J.P. KOKAI No. Sho 63-53551, alcohols described in J.P. KOKAI Nos. Sho 63-43140 and 63-53549, oximes described in J.P. KOKAI No. Sho 63-56654 and tertiary amines described in J.P. KOKAI No. Sho 63-239447. The color developer may contain, if necessary, also a preservative such as metals described in J.P. KOKAI Nos. Sho 57-44148 and 57-53749, salicylic acids described in J.P. KOKAI No. Sho 59-180588, alkanolamines described in J.P. KOKAI No. Sho 54-3582, polyethyleneimines described in J.P. KOKAI No. Sho 56-94349 and aromatic polyhydroxy compounds described in U.S. Pat. No. 3,746,544. Particularly when the hydroxylamines are used, they are preferably used in combination with the above-described alkanolamines or aromatic polyhydroxy compounds.

Particularly preferred preservatives are hydroxylamines represented by general formula (I) given in J.P. KOKAI No. Hei 3-144446. Among them, compounds having methyl, ethyl, sulfo or carboxyl group are preferred. The preservative is used in an amount of 20 to 200 mmol, preferably 30 to 150 mmol, per liter of the color developer.

The color developer for the photosensitive material for prints contains preferably $3.0 \times 10^{-2}$ to $1.5 \times 10^{-1}$ mol/l, particularly preferably $3.5 \times 10^{-2}$ to $1.0 \times 10^{-1}$ mol/l, of chlorine ion. When the chlorine ion concentration is higher than $1.5 \times 10^{-1}$ mol/l or particularly higher than $1.0 \times 10^{-1}$ mol/l, the development is retarded, which is against the object of the present invention, i.e. to rapidly attain the high maximum density and, on the contrary, a chlorine ion concentration of below $3.0 \times 10^{-2}$ mol/l is unsuitable for prevention of the fogging.

The color developer used in the present invention contains preferably $0.5 \times 10^{-5}$ to $1.0 \times 10^{-3}$ mol/l, more preferably $3.0 \times 10^{-5}$ to $5 \times 10^{-4}$ mol/l of bromine ion. When the bromine ion concentration is higher than $1 \times 10^{-3}$ mol/l, the development is retarded, and the maximum density and sensitivity are lowered and, on the contrary, when it is below $0.5 \times 10^{-5}$ mol/l, the fogging cannot be sufficiently prevented.

The chlorine ion and bromine ion can be directly added to the color developer or they can be dissolved out of the photosensitive material into the color developer in the course of the development.

When the chlorine ion is directly added to the color developer, the chlorine ion-feeding substances include sodium chloride, potassium chloride, ammonium chloride, lithium chloride, magnesium chloride and calcium chloride. The chlorine ion can be fed from a fluorescent brightener added to the color developer. The bromine ion-feeding substances include sodium bromide, potassium bromide, ammonium bromide, lithium bromide, calcium bromide and magnesium bromide.

When the chlorine ion or bromine ion is dissolved out of the photosensitive material in the course of the development, such an ion can be fed by an emulsion or another substance.

The color developer may further contain additives mentioned in the above-described J.P. KOKAI No. Hei 3-144446. For example, a compound selected from among carbonates, phosphates, borates and hydroxybenzoates mentioned on page 9 of the specification thereof can be used as a buffering agent for maintaining pH. pH of the color developer is kept preferably in the range of 9.0 to 12.5, more preferably in the range of 9.5 to 11.5, with such a buffering agent.

Antifoggants usable herein are halide ions and organic antifoggants mentioned on page 10 of that specification. Particularly when the concentration of the color developing agent in the color developer is as high as 20 mmol/l or above or when the processing temperature is as high as 40° C. or above, a considerably high bromide ion concentration is preferred. Namely, it is preferably 17 to 60 mmol/l. If necessary, the concentration can be controlled in a preferred range by removing the halogen with an ion exchange resin or ion exchange membrane.

The chelating agents preferably used herein are aminopolycarboxylic acids, aminopolyphosphonic acids, alkylphosphonic acids and phosphonocarboxylic acids. They are typified by ethylenediaminetetraacetic acid, nitrilotriacetic acid, diethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid) and salts of them. Preferred chelating agents are biodegradable compounds such as those mentioned in J.P. KOKAI Nos. Sho 63-146998, 63-199295, 63-267750 and 63-267751 and Hei 2-229146 and 3-186841, German Patent No. 3739610 and European Patent No. 468325.

The color developer of the present invention may contain, if necessary, also a development restrainer such as a benzimidazole, benzothiazole or mercapto compound; a development accelerator such as a benzyl alcohol, polyethylene glycol, quaternary ammonium salt or amine; a dye-forming coupler; a competitive coupler; an assistant developing agent such as 1-phenyl-3-pyrazolidone; a tackifier; and a surfactant such as an alkylsulfonic acid, arylsulfonic acid, aliphatic carboxylic acid or aromatic carboxylic acid.

If necessary, a development accelerator can be added to the color developer.

The development accelerators include thioether compounds described in Japanese Patent Publication for Opposition Purpose (hereinafter referred to as "J. P. KOKOKU")

Nos. Sho 37-16088, 37-5987, 38-7826, 44-12380 and 45-9019 and U.S. Pat. No. 3,813,247; p-phenylenediamine compounds described in J. P. KOKAI Nos. Sho 52-49829 and 50-15554; quaternary ammonium salts described in J. P. KOKAI No. Sho 50-137726, J. P. KOKOKU No. Sho 44-30074 and J. P. KOKAI Nos. Sho 56-156826 and 52-43429; amine compounds described in U.S. Pat. Nos. 2,494,903, 3,128,182, 4,230,796 and 3,253,919, J. P. KOKOKU No. Sho 41-11431 and U.S. Pat. Nos. 2,482,546, 2,596,926 and 3,582,346; polyalkylene oxides described in J. P. KOKOKU Nos. Sho 37-16088 and 42-25201, U.S. Pat. No. 3,128,183, J. P. KOKOKU Nos. Sho 41-11431 and 42-23883 and U.S. Pat. No. 3,532,501; as well as 1-phenyl-3-pyrazolidones and imidazoles. These development accelerators are usable, if necessary.

When the color developer is used for processing a photosensitive material for photography, the replenisher is fed in an amount of preferably 550 ml or below, more preferably 450 ml of below, and most preferably 80 to 400 ml, per $m^2$. By reducing bromide ion concentration in the replenisher or by using no bromide ion, the amount thereof can be reduced to 300 ml or below. In processing a photosensitive material for prints, the color developer replenisher is fed in an amount of 20 to 600 ml, preferably 30 to 200 ml and more preferably 40 to 100 ml, per $m^2$ of the material.

In processing the photosensitive material for photography, the processing temperature with the color developer is preferably 35° C. or above, more preferably 40° to 50° C. In processing the photosensitive material for prints, the processing temperature with the color developer is 20° to 50° C., preferably 30° to 45° C., and most preferably 37° to 42° C.

In processing the photosensitive material for photography, the processing time with the color developer is preferably 30 seconds to 3 minutes and 15 seconds, more preferably 30 seconds to 2 minutes and 30 seconds. In processing the photosensitive material for printing, the processing time with the color developer is usually shorter than 3 minutes, preferably 10 seconds to 1 minute and more preferably 10 to 30 seconds. The term "processing time" (such as development time) herein indicates the time necessitated from entering of the photosensitive material into a processing bath to entering of it into the next processing bath.

It is preferred that the developer for the photosensitive material for printing is substantially free from benzyl alcohol. To control the change of the photographic characteristics during the continuous process and also to attain the effect of the present invention, it is also preferred that the developer for the photosensitive material for printing is substantially free from sulfurous acid ion (the term "substantially free" herein indicates that sulfurous acid ion concentration is not higher than $3.0 \times 10^{-3}$ mol/l). Sulfurous acid ion concentration is preferably not higher than $1.0 \times 10^{-3}$ mol/l, and most preferably, the developer is free from sulfurous acid ion. It is to be noted, however, that a very small amount of sulfurous acid ion used, before the preparation of the developer, for inhibiting the oxidation of the processing agent kit containing a concentrated developing agent is not included therein. To control the change of the photographic chracterics depending on the change in concentration of a hydroxylamine, it is more preferred that the developer is substantially free from the hydroxylamine (the term "substantially free" herein indicates that the hydroxylamine concentration is not higher than $5.0 \times 10^{-3}$ mol/l). It is most preferred that the developer is completely free from the hydroxylamine.

It is preferred to inhibit the evaporation of the developer and oxidation thereof by air. The contact area of the processing liquid with air in the processing vessel can be represented by the opening rate defined as follows:

Opening rate=[(contact area of processing solution with air $(cm^2)$)]/ [volume of processing solution $(cm^3)$]

The opening rate $(cm^{-1})$ defined as above is preferably not higher than 0.05, more preferably in the range of 0.0005 to 0.01. The opening rate is reduced by covering the surface of the photographic processing solution in the processing vessel with a floating lid or the like, by providing a movable lid as described in J.P. KOKAI No. Hei 1-82033 or by a slit development process described in J.P. KOKAI No. Sho 63-216050. It is preferred that the processing solution in a color developer-replenishing tank or in a processing tank is sealed with a high-boiling organic solvent or a high-molecular compound to reduce the contact area thereof with air. It is particulrly preferred to use liquid paraffin, an organosiloxane or the like. The opening rate can be reduced not only in the color development and black-and-white development steps but also in all of the subsequent steps such as bleaching, bleach-fixing, fixing, water washing and stabilization steps.

The developer can be reused by regeneration. The term "regeneration of the developer" herein indicates that the used developer is treated with an anion exchange resin or by electrodialysis and that the activity of the developer is increased by adding a processing agent called "regenerating agent". The regeneration rate (rate of the overflow in the replenisher) is preferably at least 70%, particularly at least 90%.

The color-developed photosensitive material is then usually desilvered. The desilverization process herein basically comprises bleaching process and fixing process. Both processes can be conducted at the same time by a bleach-fixing process or these processes are combined with each other.

The bleaching agents include, for example, iron salts; compounds of polyvalent metals such as iron (III), cobalt (III), chromium (IV) and copper (II); peracids; quinones; and nitro compounds. Typical bleaching agents are, for example, ferric chloride, ferricyanides, bichromates; organic complex salts of iron (III) (such as metal complex salts of aminopolycarboxylic acids, e. g. ethylenediaminetetraacetic acid, diethylenetriaminepentaacetic acid, cyclohexanediaminetetraacetic acid, methyliminodiacetic acid, 1,3-diaminopropanetetraacetic acid and glycol ether diaminetetraacetic acid); persulfates; bromates; permanganates; and nitrobenzenes. Among them, preferred are ferric aminopolycarboxylates and salts of them as described on page 11 of the above-mentioned J. P. KOKAI No. Hei 3-144446. Examples of them include ferric salts of ethylenediaminetetraacetic acid, diethylenetriaminepentaacetic acid, cyclohexanediaminetetraacetic acid, methyliminodiacetic acid, 1,3-diaminopropanetetraacetic acid and glycol ether diaminetetraacetic acid. Other bleaching agents include complex salts of citric acid, tartaric acid and malic acid. Among them, particularly preferred are iron (III) complex salt of ethylenediaminetetraacetic acid and iron (III) complex salts of aminopolycarboxylic acids such as iron (III) complex salt of 1,3-diaminopropanetetraacetic acid. Such an iron (III) complex salt of aminopolycarboxylic acid is particularly effective in both bleaching solution and bleach-fixing solution.

The bleaching solution, bleach-fixing solution, pre-bleaching bath and pre-bleach-fixing bath may contain a bleaching accelerator, if necessary. Examples of the bleaching accelerators include compounds having a mercapto group or disulfido bond described in U.S. Pat. No. 3,893,858, West German Patent No. 1,290,812, J.P. KOKAI No. Sho 53-95630 and Research Disclosure No. 17129 (July, 1978); thiazolidine derivatives described in J.P. KOKAI No. Sho 50-140129; thiourea derivatives described in U.S. Pat. No. 3,706,561; iodides described in J.P. KOKAI No. Sho 58-16235; polyoxyethylene compounds described in West German Patent No. 2,748,430; polyamine compounds described in J. P. KOKOKU No. Sho 45-8836; and bromide ions. Among them, compounds having a mercapto group or disulfido group and also having a remarkable accelerating effect are preferred. Particularly preferred are compounds described in U.S. Pat. No. 3,893,858, West German Patent No. 1,290,812 and J. P. KOKAI No. Sho 53-95630. Further, compounds described in U.S. Pat. No. 4,552,834 are also preferred. These bleach-accelerators may be added also to the photosensitive material. When a color photosensitive material for photography is to be bleach-fixed, these bleaching accelerators are particularly effective.

The desilvering bath may contain rehalogenating agents, pH buffering agents and other known additives as described on page 12 of J. P. KOKAI No. Hei 3-144446, in addition to the bleaching agent.

An organic acid is preferably incorporated into the bleaching solution and bleach-fixing solution in order to prevent a bleach stain, in addition to the above-described compounds. Particularly preferred organic acids are those having an acid dissotiation constant (pKa) of 2 to 6 such as acetic acid, propionic acid, hydroxyacetic acid, succinic acid, maleic acid, glutaric acid, fumaric acid, malonic acid and adipic acid. Particularly preferred are succinic, maleic and glutaric acids.

The pH of the bleaching solution and bleach-fixing solution is usually 4.0 to 8.0. For conducting the process more rapidly, pH can be further lowered.

The fixing agents usable for the fixing solution or bleach-fixing solution include, for example, thiosulfates, thiocyanates, thioether compounds, thioureas and a large amount of iodides. Among them, the thiosulfates are commonly used and ammonium thiosulfate is most widely usable. A combination of a thiosulfate with a thiocyanate, thioether compound or thiourea is also preferred.

Examples of preferred preservatives for the fixing solution and bleach-fixing solution include sulfites, hydrogensulfites, carbonylhydrogensulfite adducts and sulfinic acid compounds described in European Patent No. 294769 A. Further, it is preferred to add a chelating agent such as an aminopolycarboxylic acid or organic phosphonic acid to the fixing solution or bleach-fixing solution in order to stabilize it. Examples of preferred chelating agents include 1-hydroxyethylidene-1,1-diphosphonic acid, ethylenediamine-N,N,N,N'-tetrakis(methylenephosphonic acid), nitrilotrimethylenephosphonic acid, ethylenediaminetetraacetic acid, diethylenetriaminepentaacetic acid, cyclohexanediaminetetraacetic acid and 1,2-propylenediaminetetraacetic acid. Among them, 1-hydroxyethylidene-1,1-diphosphonic acid and ethylenediaminetetraacetic acid are particularly preferred.

It is preferred to incorporate 0.1 to 10 mol/l of a compound having a pKa of 6.0 to 9.0 such as imidazole, 1-methylimidazole, 1-ethylimidazole or 2-methylimidazole into the fixing solution or bleach-fixing solution in order to adjust pH thereof.

The fixing solution and bleach-fixing solution can further contain various fluorescent brightening agents, antifoaming agents, surfactants, polyvinylpyrrolidones, methanol, etc.

When a replenishing system is employed in the process, the quantity of the fixing solution or bleach-fixing solution to be replenished is preferably 100 to 3,000 ml, more preferably 300 to 1800 ml, per $m^2$ of the photosensitive material. The bleach-fixing solution can be replenished by using a bleach-fixing replenisher or, as described in J.P. KOKAI No. Sho 61-143755 or Japanese Patent Application No. Hei 2-216389, overflowing bleaching solution and fixing solution can be used.

The total processing time for the photosensitive material for photography in the desilvering step comprising bleaching, bleach-fixing and fixing is preferably 30 seconds to 3 minutes, more preferably 45 seconds to 2 minutes. The processing temperature is 30° to 60° C., preferably 35° to 55° C.

In processing with a processing solution having a bleaching effect, it is particularly preferred to conduct aeration so as to keep the photographic properties very stable. The aeration can be conducted by a method known in the art, such as blowing of air into the solution having the bleaching effect or absorption of air with an ejector.

The processing solution having the bleaching effect is reusable by recovering the overflow used in the process and adding the components to regulate the composition thereof. Such a regeneration is easy in the present invention. The details of the regeneration are described on pages 39 to 40 of Fuji Film Processing Manual, Fuji Color Negative Film, CN-16 Process (revised in August, 1990) published by Fuji Photo Film Co., Ltd.

An automatic developing machine used for developing the photosensitive material of the present invention preferably has a means of transporting the photosensitive material as described in J. P. KOKAI Nos. Sho 60-191257, 60-191258 and 60-191259. As described in J. P. KOKAI No. Sho 60-191257, such a transportation means remarkably reduces the amount of the processing solution brought from the preceding bath into a subsequent bath, so that the deterioration in the function of the processing solution can be remarkably prevented. Such a function is particularly effective in reducing the processing time in each step and also in reducing the amount of the replenisher.

The desilverization step is usually followed by a step of washing with water. This washing step may be replaced with a stabilization step. In the stabilization, any of known methods described in J. P. KOKAI Nos. Sho 57-8543, 58-14834 and 60-220345 can be employed. Water washing step/stabilization step in which a stabilizing bath containing a dye-stabilizing agent and a surfactant is used as the final bath may also be employed.

The water for washing and the stabilizing bath can contain a softening agent for hard water such as an inorganic phosphoric acid, polyaminocarboxylic acid or organic aminophosphonic acid.

The amount of water used in the washing step varies in a wide range depending on the properties of the photosensitive material (which depend on, for example, couplers used), temperature of water used for washing, number of the tanks (number of stages), replenishing method such as counter flow or down-flow system and various other conditions.

The stabilizing solution contains a compound which stabilizes the color image, selected from among, for example, formalin, benzaldehydes such as m-hydroxybenzaldehyde, formaldehyde/bisulfurous acid adduct, hexamethylenetetramine and derivatives thereof, hexahydrotriazine and derivatives thereof, dimethylurea, N-methylol compounds such as N-methylolpyrazole, organic acids and pH buffering agents. The preferred amount of these compounds is 0.001 to 0.02 mol per liter of the stabilizing solution. The free formaldehyde concentration in the stabilizing solution is preferably as low as possible so as to prevent formaldehyde gas from sublimation.

Various surfactants can be incorporated into washing water and stabilizing solution so as to prevent the formation of water spots in the course of drying of the photosensitive material. Among them, preferred is an anionic surfactant, particularly an alkylphenol/ethylene oxide adduct. The alkylphenols are particularly preferably octyl-, nonyl-, dodecyl- and dinonylphenols. The molar number of ethylene oxide to be added is particularly preferably 8 to 14. It is also preferred to use a silicon surfactant having a high antifoaming effect.

The washing water and stabilizing solution preferably contain a chelating agent. Preferred chelating agents include aminopolycarboxylic acids such as ethylenediaminetetraacetic acid and diethylenetriaminepentaacetic acid; organic phosphonic acids such as 1-hydroxyethylidene-1,1-diphosphonic acid, N,N,N'-trimethylenephosphonic acid and diethylenetriamine-N,N,N',N'-tetramethylenephosphonic acid; and hydrolyzates of maleic anhydride polymers described in European Patent No. 345, 172A1.

Water treated with a reverse osmosis membrane is effectively used as the washing and/or stabilizing solution.

Preferably, each processing solution is used at 10° to 50° C. Although the standard temperature ranges from 33° to 38° C., it is also possible to accelerate the process and thereby to reduce the process time at a higher temperature or, on the contrary, to conduct the process at a lower temperature so as to improve the image quality and stability of the processing solution.

Each solution is usable for processing two or more kinds of photosensitive materials. For example, a color negative film and a color paper are processed with the same solution to reduce the cost of the processing machine and to simplify the process. The processing solutions are usable for processing various color photosensitive materials such as color negative films for movies, color reversal films for slides or television, color papers, color positive films and color reversal papers. They are suitable also for film units with a lens described in J. P. KOKOKU No. Hei 2-32615 and Japanese Utility Model Publication for Opposition Purpose (hereinafter referred to as "J. UM. KOKOKU") No. Hei 3-39784.

The photosensitive materials must have at least one photosensitive layer on a support. A typical example of the silver halide photosensitive material comprises at least one color-sensitive layer (comprising two or more silver halide emulsion layers having substantially the same-color sensitivity but different degree of sensitivity) formed on the support. The photosensitive layer is a unit photosensitive layer sensitive to any of blue, green and red lights. In the photographic photosensitive materials for multi-layered silver halide color photographs, the arrangement of the unit photosensitive layers is generally as follows: a red-sensitive layer, a green-sensitive layer and a blue-sensitive layer in this order from the support. However, the order of the arrangement may be reversed or a photosensitive layer having a different color sensitivity may be interposed between layers having the same color sensitivity. A photo-insensitive layer can be provided between the silver halide photosensitive layers or as the top layer or the bottom layer. The photoinsensitive layer may contain a coupler, DIR compound, color-mixing inhibitor, etc. The two or more silver halide emulsion layers constituting the unit photosensitive layer have preferably a structure consisting of two layers, i.e. a high sensitivity emulsion layer and a low sensitivity emulsion layer, as described in D. E. Patent No. 1,121,470 or G. B. Patent No. 923,045. Usually the arrangement of the layers is such that the sensitivity thereof decreases gradually toward the support. An emulsion layer having a low sensitivity may be formed away from the support and an emulsion layer having a high sensitivity may be formed close to the support as described in J. P. KOKAI Nos. Sho 57-112751, 62-200350, 62-206541 and 62-206543.

The arrangement can be as follows: a blue-sensitive layer/GH/RH/GL/RL toward the support as described in J. P. KOKOKU No. Sho 55-34932, or a blue-sensitive layer/GL/RL/GH/RH toward the support as described in J. P. KOKAI Nos. Sho 56-25738 and 62-63936.

Another arrangement is that of three layers having sensitivities gradually lowered toward the support, i.e. a top layer (a silver halide emulsion layer having the highest sensitivity), middle layer (a silver halide emulsion layer having a lower sensitivity) and bottom layer (a silver halide emulsion layer having a sensitivity lower than that of the middle layer) as described in J. P. KOKOKU No. Sho 49-15495. Even in such an arrangement comprising three layers having sensitivities different from each other, layers sensitive to the same color may further comprise an emulsion layer having a medium sensitivity/emulsion layer having a high sensitivity/emulsion layer having a low sensitivity in the order toward the support as described in J. P. KOKAI No. Sho 59-202464. In another example, the arrangement may be as follows: high-sensitivity emulsion layer/low sensitivity emulsion layer/medium sensitivity emulsion layer or low sensitivity emulsion layer/medium sensitivity emulsion layer/high sensitivity emulsion layer. When the photosensitive material has four or more layers, the arrangement of them may be varied as described above.

For improving the color reproducibility, it is preferred to form a donor layer (CL) having an interlayer effect and a spectral sensitivity distribution different from that of the main photosensitive layers such as BL, GL and RL at a position adjacent to or close to the main photosensitive layers as described in U.S. Pat. Nos. 4,663,271, 4,705,744 and 4,707,436 and J. P. KOKAI Nos. Sho 62-160448 and 63-89850.

In an ordinary photosensitive material (color photograhic paper) for prints, the grains in the silver halide emulsions are spectrally sensitized with blue-sensitive, green-sensitive and red-sensitive spectrally sensitized dyes in the above-described order of the color layers, and the support is coated with them in the above-described order. However, the order of the coating of them may be varied. Namely, from the viewpoint of the rapid processing, the top layer is preferably a photosensitive layer containing silver halide grains having the largest average grain size; and from the viewpoint of the storability under the irradiation with light, the bottom layer is preferably a magenta-coloring photosensitive layer.

The structure of the photosensitive layer and color hue may be free from the above-described conditions, and at least one infrared-sensitive silver halide emulsion layer may be used.

The silver halides preferably used for the photograhic photosensitive materials include silver bromoiodide, silver chloroiodide and silver chlorobromoiodide containing at most about 30 molar % of silver iodide. Silver bromoiodide and silver chlorobromoiodide containing about 2 to 10 molar % of silver iodide are particularly preferred.

The silver halide grains in the photographic emulsion may be in a regular crystal form such as a cubic, octahedral or tetradecahedral form; an irregular crystal form such as spherical or plate form; or a complex crystal form thereof. They include also those having a crystal fault such as a twin plate.

The silver halide grain diameter may range from about 0.2 μm or less to as large as that having a projection area diameter of about 10 μm. The emulsion may be either a polydisperse emulsion or monodisperse emulsion. The monodispersion emulsion having a dispersion factor of 15% or below, preferably 10% or below is preferred.

The silver halide photographic emulsion can be prepared by processes described in, for example, Research Disclosure (hereinafter referred to as "RD"), No. 17643 (December, 1978), pp. 22 to 23, "1. Emulsion preparation and types"; RD No. 18716 (November, 1979), p. 648; and RD No. 307105 (November, 1989), pp. 863 to 865.

Tabular grains having an aspect ratio of 3 or higher are also usable. The tabular grains can be easily prepared by processes described in, for example, Gutoff, Photographic Science and Engineering, Vol. 14, pp. 248 to 257 (1970); U.S. Pat. Nos. 4,434,226; and G. B. Patent No. 2,112,157.

The crystal structure of the grains in the above emulsion may be uniform; the grains may comprise an inside portion and an outside portion which are composed of silver halides different from each other; or the structure may be a laminated one. Different silver halide grains can be bonded together by an epitaxial bond or they can be bonded with a compound other than silver halides such as silver rhodanate or lead oxide. A mixture of grains having various crystal forms can also be used.

The emulsion may be of a surface-latent image type for forming a latent image mainly on the surface thereof, of an internal latent image type for forming a latent image in the grains or of such a type that a latent image is formed both on the surface and in the grains. The emulsion must be a negative one. In the internal latent image type emulsions, a core/shell type internal latent image type emulsion described in J.P. KOKAI No. Sho 63-264740 may also be used. Processes for producing the emulsion are described in J.P. KOKAI No. Sho 59-133542. The thickness of the shells in the emulsion which varies depending on the developing process is preferably 3 to 40 nm, particularly preferably 5 to 20 nm.

The silver halide emulsion to be used in the present invention is usually physically and chemically ripened and spectrally sensitized. The additives to be used in these steps are shown in RD Nos. 17643, 18716 and 307105. The portions in which the additives are mentioned in these three Research Disclosures are summarized in a table given below.

The amount of silver to be applied to the photographic photosensitive material is preferably not larger than 6.0 g/m$^2$, most preferably not larger than 4.5 g/m$^2$.

The silver halide grains in the photosensitive material for prints are preferably silver chloride, silver chlorobromide or silver chlorobromoiodide grains comprising at least 95 molar % of silver chloride. Particularly, for the rapid process, substantially silver iodide-free silver chlorobromide or silver chloride can be preferably used. The term "substantially silver iodide-free" herein indicates that silver iodide content is not higher than 1 molar %, preferably not higher than 0.2 molar %. Further, in some cases, high-silver chloride grains containing 0.01 to 3 molar % of silver iodide on the emulsion surface as described in J. P. KOKAI No. Hei 3-84545 are preferably used so as to improve the high-intensity sensitivity, spectral sensitivity or storability of the photosensitive material. Although the halogen composition of the emulsion may be the same or different among the grains, the properties of all the grains can be easily made uniform by using an emulsion of grains having a uniform halogen composition. As for the halogen composition distribution in the silver halide grains in the emulsion, grains can be suitably selected from among those having a so-called homogeneous structure in which the composition in any part of the grain is uniform; those having a so-called laminated structure in which the halogen composition in the core of the silver halide grain is different from that in the shell (one or more layers) surrounding the core; and those having a structure which has a non-layer part having a different halogen composition in the core or on the surface (when such a ion-layer part is on the surface of the grain, the structure is such that the different composition part is conjugated with the edge, corner or surface of the grain).

It is also effective to further increase the silver chloride content of the silver halide emulsion for the purpose of reducing the amount of the developer replenisher. In such a case, an emulsion comprising substantially pure silver chloride, i. e. an emulsion having a silver chloride content of 98 to 100 molar %, is also preferably used.

The average grain size (number-average diameter of a circle having an area equal to that of the projected area of the grain) of the silver halide grains contained in the silver halide emulsion is preferably 0.1 to 2 μm.

As for the grain size distribution, the coefficient of variation (calculated by dividing the standard deviation of the grain size distribution by the average grain size) is not higher than 20%, desirably not higher than 15%, and more desirably not higher than 10%. Namely, the emulsion is so-called monodisperse emulsion. In order to obtain a wide latitude, this monodisperse emulsion is preferably blended in the same layer or it is applied to form an interlayer.

The localized silver halide grain phase or its substrate may contain a different metal ion or complex ion thereof. Preferred are those selected from among ions and complexes of metals of the Groups VIII and IIb in the Periodic table, and lead ion and thallium ion. The localized phase mainly contains an ion or complex ion of a metal selected from among iridium, rhodium and iron, and the substrate mainly contains an ion or complex ion of a metal selected from among osmium, iridium, rhodium, platinum, ruthenium, palladium, cobalt, nickel and iron. The kind and concentration of the metal ion in the locallized phase may be different from those in the substrate. A combination of two or more kinds of these metals can also be used. It is particularly preferred that the iron and iridium compounds are in the silver bromide locallized phase.

The silver halide emulsion is usually chemically and spectrally sensitized.

The chemical sensitization is conducted with a chalcogen sensitizer (in particular, sulfur sensitization typified by the addition of an unstable sulfur compound, selenium sensitization with a selenium compound or tellurium sensitization with a tellurium compound). A noble metal sensitization typified by gold sensitization and reduction sensitization can be conducted either separately or in combination of them. Compounds preferably used for the chemical sensitization are those described from the right lower column on page 18 to the right upper column on p. 22 of J. P. KOKAI No. Sho 62-215272.

The silver halide emulsion can contain various compounds or precursors thereof so as to prevent the fogging during the production, storage or processing of the photosensitive material, or to stabilize the photographic properties. Preferred examples of these compounds are described on pages 39 to 72 of the above-mentioned J. P. KOKAI No. Sho 62-215272. Further, 5-arylamino-1,2,3,4-thiatriazole compounds (the aryl residue has at least one electron-attractive group) described in European Patent No. 0447647 are also preferably used.

The spectral sensitization is conducted for the purpose of imparting a spectral sensitivity in a desired wavelength range to the emulsion for forming each layer of the photosensitive material.

The spectral sensitizing dyes used for the spectral sensitization in blue, green and red zones include, for example, those described in F. M. Harmer, Heterocyclic compounds—Cyanine dyes and related compounds (published by John Wiley & Sons [New York, London] in 1964). Examples of the preferred compounds and the spectral sensitization method are described from the right upper column, page 22 to page 38 of the above-mentioned J. P. KOKAI No. Sho 62-215272. As for the red-sensitive spectral sensitizing dyes for the silver halide grains having a high silver chloride content, spectral sensitizing dyes described in J. P. KOKAI No. Hei 3-123340 are very excellent in the stability, adsorption strength and dependence of the exposure on the temperature.

For the efficient spectral sensitization of the infrared zone, sensitizing dyes described from the left upper column, page 12 to the left lower column, page 21 of J. P. KOKAI No. Hei 3-15049; from the left lower column, page 4 to the left lower column, page 15 of J. P. KOKAI No. Hei 3-20730; from line 21, page 4 to line 54, page 6 of European Patent No. 0,420,011; from line 12, page 4 to line 33, page 10 of European Patent No. 0,420,012; European Patent No. 0,443,466 and U.S. Pat. No. 4,975,362 are preferably used.

A dye (particularly oxonol or cyanine dye) which can be decolored by the process as described on pages 27 to 76 of European Patent No. 0,337,490 A2 can be incorporated into the hydrophilic colloid layer for the purpose of preventing the irradiation or halation or improving the safety of the safelight.

Some of the water-soluble dyes impair the color separation or safety of the safelight when they are used in an increased amount. Preferred dyes usable without impairing the color separation are water-soluble dyes described in Japanese Patent Application Nos. Hei 03- 310143, 03-310189 and 03-310139.

Gelatin is advantageously used as the binder or protective colloid for the photosensitive materials. Other hydrophilic colloids can also be used either singly or in combination with gelatin. Preferred gelatin is a low-calcium gelatin having a calcium content of at most 800 ppm, more preferably at most 200 ppm. An antifungal agent as described in J. P. KOKAI No. Sho 63-271247 is preferably used in order to prevent the propagation of various fungi and bacteria in the hydrophilic colloid layer, since they deteriorate the image.

In the printer exposure of the photosensitive material for printing, a band stop filter described in U.S. Pat. No. 4,880,726 is preferably used for eliminating the photo-color-mixing and also for remarkably improving the color reproducibility.

After the completion of the exposure, the photosensitive material can be subjected to an ordinary color development process. To rapidly conduct the process, it is preferred to conduct bleach-fixing after the color development. Particularly when the above-described high-silver chloride emulsion is used, pH of the bleach-fixing solution is preferably not higher than about 6.5, particularly not higher than about 6, for accelerating the desilverization.

The photographic additives usable herein are also mentioned in RD, and the corresponding portions are shown in the following table:

| Additive | RD 17643 | RD 18716 | RD 307105 |
|---|---|---|---|
| 1. Chemical sensitizer | p. 23 | p. 648, right column | p. 866 |
| 2. Sensitivity improver | | p. 648, right column | |
| 3. Spectral sensitizer and supersensitizer | pp. 23 to 24 | p. 648, right colum to p. 649, right column | pp. 866 to 868 |
| 4. Brightening agent | p. 24 | p. 647, right column | p. 868 |
| 5. Light absorber, filter, dye and UV absorber | pp. 25 to 26 | p. 649, right column to p. 650, left column | p. 873 |
| 6. Binder | p. 26 | p. 651, left column | pp. 873 to 874 |
| 7. Plasticizer and lubricant | p. 27 | p. 650, right column | p. 876 |
| 8. Coating aid and surfactant | pp. 26 and 27 | p. 650, right column | pp. 875 to 876 |
| 9. Antistatic agent | p. 27 | p. 650, right column | pp. 876 to 877 |
| 10. Matting agent | | | pp. 878 to 879 |

The photosensitive material can contain various dye-forming couplers. Among them, the following couplers are particularly preferred:

Yellow couplers: couplers represented by formulae (I) and (II) in EP 502,424A; those of formulae (I) and (II) in E.P. No. 513,496A (particularly Y-28 on page 18); those of general formula (I) in claim 1 of Japanese Patent Application No. Hei 4-134523; those of general formula (I) in lines 45 to 55, column 1 of U.S. Pat. No. 5,066,576; those of general formula (I) in paragraph 0008 of J. P. KOKAI No. Hei 4-274425; those set forth in claim 1 on p. 40 of E. P. No. 498,381A1 [particularly D-35 on p. 18]; those of formula (Y) on p. 4 of E. P. No. 447,969A1 (particularly Y-1 on p. 17 and Y-54 on p. 41); and those of general formulae (II) to (IV) in lines 36 to 58, column 7 of U.S. Pat. No. 4,476,219 (particularly II-17, 19 (column 17) and II-24 (column 19)], Acylacetanilide couplers: particularly pivaloylacetanilide couplers having a halogen atom or alkoxyl group at the o-position of the anilide ring; acylacetanilide couplers wherein the acyl group is a cycloalkanecarbonyl group having a substituent at the 1-position as described in E. P. No. 0,447,969A and J. P. KOKAI Nos. Hei 5-107701 and 5-113642; and malondianilide couplers described in E. P. Nos. 0,482,552A and 0,524,540A, Magenta couplers: those described in J. P. KOKAI No. Hei 3-39737 [L-57 (right lower column, p. 11), L-68 (right lower column, p. 12) and L-77 (right lower column, p. 13); [A-4]-63 (p. 134), [A-4]-73 and 75 (p. 139) of E. P. No. 456,257; M-4 and 6 (p. 26) and M-7 (p. 27) of E. P. No. 486,965; M-45 in paragraph 0024 of Japanese Patent Application No. Hei 4-234120; M-1 in paragraph 0036 of Japanese Patent Application No. Hei 4-36917; and M-22 in paragraph 0237 of J. P. KOKAI No. Hei 4-362631, 5-Pyrazolone magenta couplers: those of arylthio-linked coupling-off type described in W.O. 92/18901, 92/18902 and 92/18903, Pyrazoloazole couplers: those containing a sulfonamido group in the molecule as described in J. P. KOKAI No. Sho 61-65246; those having an alkoxyphenylsulfonamido ballast group as described in J. P. KOKAI No. Sho 61-147254; and those having an alkoxy or aryloxy group at the 6-position as described in EP Nos. 226,849A and 294,785A, Cyan couplers: CX-1, 3, 4, 5, 11, 12, 14 and 15 (pp. 14 to 16) of J. P. KOKAI No. Hei 4-204843; C-7 and 10 (p. 35), 34 and 35 (p. 37),, (I-1) and (I-17) (pp. 42 to 43) of J. P. KOKAI No. Hei 4-43345; and those of general formula (Ia) or (Ib) in claim 1 of Japanese Patent Application No. Hei 4-236333, Polymer couplers: P-1 and P-5 (p. 11) of J. P. KOKAI No. Hei 2-44345, and Phenol couplers and naphthol couplers; diphenylimidazole cyan couplers described in J. P. KOKAI No. Hei 2-33144; 3-hydroxypyridine cyan couplers described in E. P. No. 0,333,185A2; cyclic active methylene cyan couplers described in J. P. KOKAI No. Sho 64-32260; pyrrolopyrazole cyan couplers described in E. P. No. 0,456,226A1; pyrroloimidazole cyan couplers described in E. P. No. 0,484,909; and pyrrolotriazole cyan couplers described in E. P. Nos. 0488,248 and 0,491,197A1.

The couplers capable of forming a colored dye having a suitable diffusibility are preferably those described in U.S. Pat. No. 4,366,237, G.B. Patent No. 2,125,570, E. P. No. 96,873B and DE P. No. 3,234,533.

The couplers used for compensation for unnecessary absorption of the colored dye are preferably as follows: yellow-colored cyan couplers of formulae (CI), (CII), (CIII) and (CIV) on p. 5 of E. P. No. 456,257A1 (particularly YC-86 on p. 84); yellow-colored magenta coupler ExM-7 (p. 202), EX-1 (p. 249) and EX-7 (p. 251) described in E. P. No. 456,257A1; magenta-colored cyan coupler CC-9 (column 8) and CC-13 (column 10) described in U.S. Pat. No. 4,833,069; couplers (2) (column 8) in U.S. Pat. No. 4,837,136; and colorless masking couplers of formula (A) in claim 1 of WO 92/11575 (particularly compounds given on pages 36 to 45).

Compounds (including couplers) capable of reacting with an oxidation product of the developing agent to form a photographically useful compound residue are as follows: development inhibitor-releasing compounds such as compounds of formulae (I), (II), (III) and (IV) on page 11 of E. P. No. 378,236A1 [particularly compounds T-101 (p. 30), T-104 (p. 31), T-113 (p. 36), T-131 (p. 45), T-144 (p. 51) and T-158(p. 58)], compounds of formula (I) on page 7 of E. P. No. 436,938A2 [particularly D-49 (p. 51)], compounds of formula (1) in Japanese Patent Application No. Hei 4-134523 [particularly (23) in paragraph 0027], compounds of formulae (I), (II) and (III) on pages 5 to 6 of E. P. No. 440,195A2 [particularly I-(1) on page 29]; bleaching accelerator-releasing compounds such as compounds of formulae (I) and (II) on page 5 of E. P. No. 310,125A2 [particularly (60) and (61) on p. 61] and compounds of formula (I) in claim 1 of Japanese Patent Application No. Hei 4-325564 [particularly (7) in paragraph 0022]; ligand-releasing compounds such as those of LIG-X in claim 1 of U.S. Pat. No. 4,555,478 (particularly compounds in lines 21 to 41 in column 12); leuco dye-releasing compounds such as compounds 1 to 6 in columns 3 to 8 of U.S. Pat. No. 4,749,641; fluorescent dye-releasing compounds such as compounds represented by COUP-DYE in claim 1 of U.S. Pat. No. 4,774,181 (particularly compounds 1 to 11 in columns 7 to 10); development accelerator- or fogging agent-releasing compounds such as those of formulae (1), (2) and (3) in column 3 of U.S. Pat. No. 4,656,123 [particularly (I-22) in column 25] and ExZK-2 in lines 36 to 38 on page 75 of E. P. No. 450,637A2; compounds which do not release a dye-forming group before coupling-off such as compounds of formula (I) in claim 1 of U.S. Pat. No. 4,857,447 (particularly Y-1 to Y-19 in columns 25 to 36).

As additives other than the couplers, those described below are preferred.

Dispersion medium for oil-soluble organic compounds: P-3, 5, 16, 19, 25, 30; 42, 49, 54, 55, 66, 81, 85, 86 and 93 (pp. 140 to 144) described in J. P. KOKAI No. Sho 62-215272; latices for impregnation of oil-soluble organic compounds: latices described in U.S. Pat. No. 4,199,363; oxidized developing agent scavengers: compounds of formula (I) in lines 54 to 62, column 2 of U.S. Pat. No. 4,978,606 [particularly 1-(1), (2), (6) and (12) in columns 4 and 5] and those of formulae in lines 5 to 10, column 2 of U.S. Pat. No. 4,923,787 [particularly compound 1 (column 3)]; antistaining agents: those of formulae (I) to (III) in lines 30 to 33, p. 4 of E. P. No. 298,321A, particularly I-47, 72, III-i and 27 (pp. 24 to 48); discoloration inhibitors: A-6, 7, 20, 21, 23, 24, 25, 26, 30, 37, 40, 42, 48, 63, 90, 92, 94 and 164 of E. P. No. 298,321A (pp. 69 to 118), II-1 to III-23 in columns 25 to 38 of U.S. Pat. No. 5,122,444, particularly III-10, I-1 to III-4 on pp. 8 to 12 of E. P. No. 471,347A, particularly II-2, and A-1 to 48 in columns 32 to 40 of U.S. Pat. No. 5,139,931, particularly A-39 and 42; materials capable of reducing the amount of color image increasing agent or color mixing-inhibitor used: I-1 to II-15 on pp. 5 to 24 of E. P. No. 411,324A, particularly I-46; formalin scavengers: SCV-1 to 28 on pp. 24 to 29 of E. P. No. 477,932A, particularly SCV-8; hardeners: H-1, 4, 6, 8 and 14 on p. 17 of J. P. KOKAI No. Hei 1-214845, and compounds (H-1 to 54) of formulae (VII) to (XII) in columns 13 to 23 of U.S. Pat. No. 4,618,573, compounds (H-1 to 76) of formula (6) in the right, lower part on p. 8 of J. P. KOKAI No. Hei 2-214852, particularly H-14, and compounds set forth in claim 1 of U.S. Pat. No. 3,325,287; development inhibitor precursors: P-24, 37 and 39 (pp. 6 and 7) of J. P. KOKAI No. Sho 62-168139; and compounds set forth in claim 1 of U.S. Pat. No. 5,019,492, particulrly 28 and 29 in column 7; antiseptics and mildew-proofing agents: I-1 to III-43 in columns 3 to 15 of U.S. Pat. No. 4,923,790, particularly II-1, 9, 10, 18 and III-25; stabilizers and antifoggants: I-1 to (14) in columns 6 to 16 of U.S. Pat. No. 4,923,793, particularly I-1, 60, (2) and (13), and compounds 1 to 65 in columns 25 to 32 of U.S. Pat. No. 4,952,483, particularly 36; chemical sensitizers: triphenylphosphine selenide and compound 50 of J. P. KOKAI No. Hei 5-40324; dyes: a-l to b-20 on pp. 15 to 18 of J. P. KOKAI No. Hei 3-156450, particularly a-1, 12, 18, 27, 35, 36 and b-5, V-1 to 23 on pp. 27 to 29, particularly V-1, F-I-1 to F-II-43 on pp. 33 to 55 of E. P. No. 445,627A, particularly F-I-11 and F-II-8, III-1 to 36, on pp. 17 to 28 of E. P. No. 457,153A, particularly III-1 and 3, fine crystal dispersions of Dye-1 to 124 on pp. 8 to 26 of W088/04794, compounds 1 to 22 on pp. 6 to 11 of E. P. No. 319,999A, particularly compound 1, compounds D-1 to 87 of formulae (1) to (3) (pp. 3 to 28) of E. P. No. 519,306A, compounds 1 to 22 (columns 3 to 10) of formula (I) in U.S. Pat. No. 4,268,622, and compounds (1) to (31) of formula (I) (columns 2 to 9) of U.S. Pat. No. 4,923,788; and UV absorbers: compounds (18b) to (18r) of formula (1) and 101 to 427 (pp. 6 to 9) of J. P. KOKAI No. 46-3335, compounds (3) to (66) (pp. 10 to 44) of formula (I), compounds HBT-1 to 10 (p. 14) of formula (III) of E. P. No. 520,938A, and compounds (1) to (31) of formula (1) (columns 2 to 9) of E. P. No. 521,823A.

The support used for the photosensitive material for printing may be made of any material such as a glass, paper or plastic film so far as the photographic emulsion layer can be applied thereto. The most preferred is a support of reflection type.

The term "support of reflection type" herein indicates a support having a high reflectivity so as to obtain a clear dye image in the silver halide emulsion layer. The supports of this type include those coated with a hydrophobic resin containing a light-reflecting substance such as titanium oxide, zinc oxide, calcium carbonate or calcium sulfate dispersed therein, and those comprising the hydrophobic resin per se containing the light-reflecting substance dispersed therein. The supports include, for example, a polyethylene-coated paper, polyethylene terephthalate-coated paper, synthetic polypropylene paper, transparent support having a reflective layer or containing a reflective substance, such as a glass plate, a polyester film such as polyethylene terephthalate, cellulose triacetate or cellulose nitrate film, polyamide film, polycarbonate film, polystyrene film and vinyl chloride resin film. The preferred supports of reflection type used in the present invention are paper supports the both surfaces of which are each coated with a water-resistant resin layer, wherein at least one of the water-resistant resin layers contains fine white pigment particles.

The water-resistant resins used for forming the reflective support are those having a water absorption of not higher than 0.5% by weight, preferably not higher than 0.1% by weight. They include polyolefins such as polyethylene, polypropylene and other ethylene polymers; vinyl polymers and copolymers thereof such as polystyrene, polyacrylate and copolymers of them; and polyesters such as polyethylene terephthalate and polyethylene isophthalate and copolymers thereof. Particularly preferred are polyethylene and polyesters.

The polyethylenes usable herein are high-density polyethylene, low-density polyethylene, linear low-density polyethylene and blends of these polyethylenes. These polyethylene resins preferably have a melt flow rate (hereinafter referred to as "MFR") in the range of 1.2 to 12 g/10 min as determined under conditions 4 in Table 1 of JIS K 7210 before processing. The term "MFR of polyolefin resin before processing" herein indicates MFR of the resin before blending it with a blueing agent or white pigment.

The supports suitable for the photosensitive material are described, for example, on page 28 of the above-described RD. 17643; from right column, page 647 to left column, page 648 of RD. 18716; and on page 879 of RD 307105.

The photosensitive material for the photography has a total thickness of the hydrophilic colloidal layers on the emulsion layer-side of 23 μm or below, preferably 20 μm or below, and particularly 13 to 17 μm. The film-swelling rate $T_{1/2}$ is preferably 5 to 15 seconds $T_{1/2}$ is defined to be the time necessitated for attaining the thickness of a half (½) of the saturated film thickness when 90% of the maximum swelled film thickness in defined as the saturated film thickness, the maximum swelled film thickness being obtained by processing with a color developing solution at 30° C. for 3 minutes and 15 seconds. The film-swelling rate $T_{1/2}$ can be controlled by adding a hardener to gelatin used as the binder or by varying the time conditions after the coating. The swelling rate is preferably 150 to 350%. The swelling rate can be calculated from the maximum thickness of the swollen film obtained under the above-described conditions by the following formula:

[(Maximum thickness of swollen film)-(film thickness)]/(film thickness).

The photosensitive material can have a hydrophilic colloid layer (in other words, back layer) having a total thickness of 2 to 20 μm on dry basis on the opposite side to the emulsion layer. The back layer preferably contains the above-described light absorber, filter dye, ultraviolet absorber, antistatic agent, hardener, binder, plasticizer, lubricant, coating aid, surfactant, etc. The swelling rate of the back layer is preferably 150 to 500%.

The photosensitive materials preferably used in the present invention are those described below.

The photosensitive materials preferably used herein are those having a magnetic recording layer which comprises magnetic particles (preferably ferromagnetic iron oxide particles coated with Co, and the like) dispersed in a binder. The recording layer is preferably optically transparent and covers the whole surface of the photosensitive material. The magnetic particles may be treated with a coupling agent as described in J. P. KOKAI No. Hei 6-161032. Polymers described in, for example, J. P. KOKAI No. Hei 4-219569 are preferably used as the binder. Although the recording layer may be formed in any part of the support, it is preferably formed on the opposite side (back layer) of the support to the emulsion layer. Preferably, a layer containing a lubricant is formed on the recording layer and a matting agent is contained in the outmost photosensitive emulsion layer on the support.

The photosensitive material preferably contains an antistatic agent so that it still has the antistatic properties even after the development process. Preferred antistatic agents are electroconductive metal oxides and ionic polymers. The antistatic agent is preferably used so as to obtain an electric resistance of not above $10^{12} \Omega \cdot cm$ at a temperature of 25° C. and RH of 10%.

The photosensitive materials having the magnetic recording layer are described in U.S. Pat. Nos. 5,336,589, 5,250, 404, 5,229,259 and 5,215,874 and EP 466,130A.

The support for the photosensitive material is preferably a thin layer of a polyester having no rolling properties. The thickness of the support is 50 to 105 μm, and the main material therefor is preferably a polyethylene aromatic dicarboxylate polyester (particularly a polyester produced mainly from benzenedicarboxylic acid or naphthalenedicarboxylic acid and ethylene glycol). The support has a glass transition temperature of preferably 50° to 200° C. The surface of the support is processed by ultraviolet irradiation, corona discharge, glow discharge or flaming. The support is preferably heat-treated at a temperature in the range of 40° C. to the glass transition temperature of the support for 0.1 to 1,500 hours before or after the formation of the subbing layer and before the formation of the emulsion layer. The support as well as photosensitive material, development process and cartridge are described in Kokai Giho (public disclosure) No. 94-6023 [published by Hatsumei Kyokai (Japan Institute of Invention and Innovation) in 1994].

EXAMPLES

The following Examples will further illustrate the present invention, which by no means limit the invention.

Example 1

Compound (D-2) of the present invention shown above was synthesized according to the following reaction scheme:

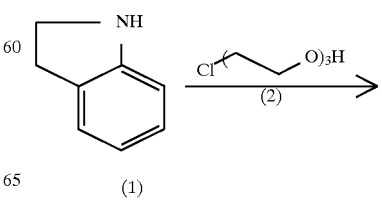

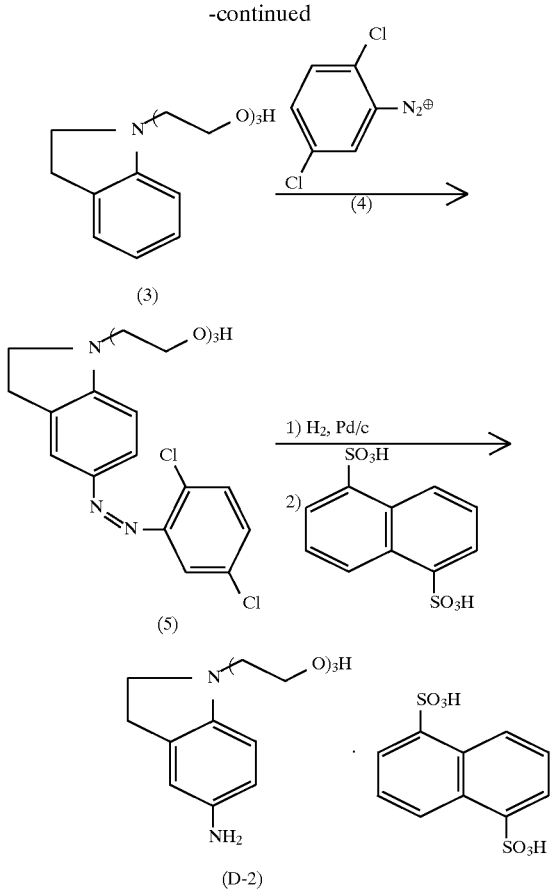

addition of the diazonium salt solution was stopped when the compound (3) had disappeared from the reaction system. After the completion of the addition followed by stirring for 30 minutes, methanol was distilled off under reduced pressure. The reaction mixture was poured into ice and neutralized by adding a sodium hydroxide solution, and then 1.5 l of ethyl acetate and 500 ml of water were added thereto to conduct the extraction. The obtained ethyl acetate layer was washed with a mixture of 700 ml of water and 200 ml of saturated aqueous common salt solution four times and then dried over anhydrous sodium sulfate. The product was concentrated with a rotary evaporator and the obtained residue was purified by silica gel column chromatography to obtain 25.5 g of the intended compound (5) (yield: 51%).

Synthesis of compound (D-2):

25.5 g of the compound (5), 2 g of palladium-carbon (10%) and 73 ml of methanol were fed into an autoclave and stirred at room temperature under a hydrogen pressure of 100 atm for 5 hours. A solution of 21.6 g of naphthalene-1,5-disulfonic acid tetrahydrate in 40 ml of methanol was added to the obtained reaction mixture. The resultant mixture was filtered and the filtrate was concentrated with a rotary evaporator. 200 ml of ethyl acetate and 200 ml of water were added to the concentrate, and the resultant mixture was stirred to obtain a solution, thereby forming layers. The aqueous layer was separated and washed with 200 ml of ethyl acetate three times. The aqueous layer thus obtained was concentrated with a rotary evaporator. Crystals separated from the solution in mixed methanol and ethanol were taken by filtration to obtain 22.2 g (yield: 67%) of the intended compound (D-2).

NMR($D_2O$): δ=8.82 (d, 2H, J=9.7 Hz), 8.20 (d, 2H, J=9.7 Hz), 7.73 (dd, 2H, J=9.7 Hz, 9.7 Hz), 7.28 (m, 1H), 7.2 to 7.4 (m, 2H), 3.80 (t, 2H, J=8.3 Hz), 3.4–3.7 (m, 15H), 3.10 (t, 2H, J=8.3 Hz).

Synthesis of compound (3):

23.8 g of the compound (1), 15.0 g of sodium iodide, 34.0 g of sodium hydrogencarbonate and 70 ml of N,N-dimethylacetamide were fed into a three-necked flask. 37.8 ml of the compound (2) was dropped into the obtained mixture under stirring and heating to an outer temperature of 130° C. for a period of 10 minutes. After the completion of the dropping followed by heating and stirring for 3 hours, the reaction mixture was cooled to room temperature. 400 ml of ethyl acetate and 400 ml of water were added to the mixture and then the obtained mixture was stirred to conduct the extraction. The ethyl acetate layer thus obtained was washed with a mixture of 300 ml of water and 100 ml of saturated aqueous common salt solution 4 times, and then dried over anhydrous sodium sulfate. The product was concentrated with a rotary evaporator. The residue was purified by silica gel column chromatography to obtain 29.4 g (yield: 58.5%) of the intended compound (3).

Synthesis of compound (5):

28.4 g of 2,5-dichloroaniline and 300 ml of water were fed into a three-necked flask, and 59.3 ml of sulfuric acid was added to the resultant mixture under stirring under cooling with ice. A solution of 13.4 g of sodium nitrite in 25 ml of water was dropped into the obtained mixture for a period of 10 minutes while the inner temperature was kept at 8° C. or below. After the completion of the dropping, the stirring was continued for 30 minutes. Separately, 29.4 g of the compound (3), 96 g of sodium acetate, 67 ml of acetic acid and 200 ml of methanol were fed into another three-necked flask, and the diazonium salt solution prepared as described above was added thereto under stirring and cooling with ice while the inner temperature was kept at 16° C. or below. In this step, the reaction procedure was followed by TLC, and the Example 2

Compound (D-40) of the present invention shown above was synthesized according to the following reaction scheme:

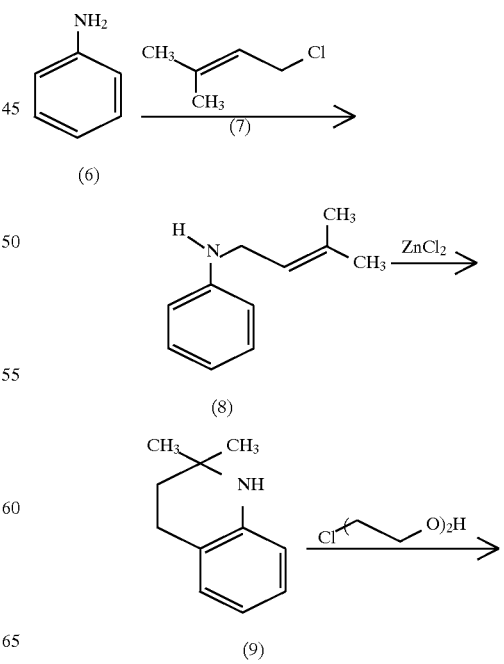

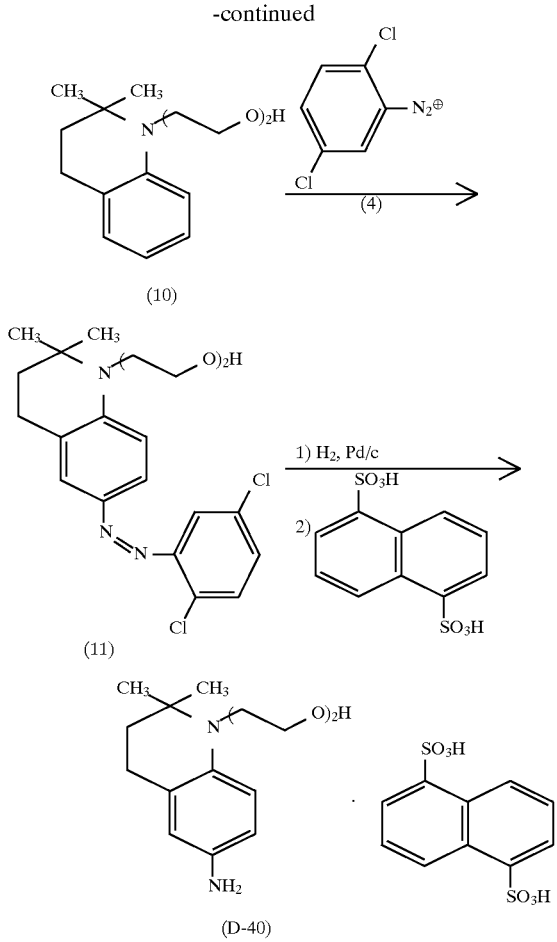

Synthesis of compound (8):

135 g of aniline, 365.4 g of sodium hydrogencarbonate and 500 ml of N,N-dimethylacetamide were fed into a three-necked flask. 140 g of the compound (7) was dropped into the obtained mixture under stirring and heating to an outer temperature of 120° C. for a period of 30 minutes. After the completion of the dropping followed by heating at an outer temperature of 130° C. and stirring for 3 hours, the reaction mixture was cooled to room temperature. 1 l of ethyl acetate and 600 ml of water were added to the mixture and the extraction was conducted. The ethyl acetate layer thus obtained was washed with a mixture of 600 ml of water and 200 ml of saturated aqueous common salt solution 3 times, and then dried over anhydrous sodium sulfate. The product was concentrated with a rotary evaporator. The residue was purified by silica gel column chromatography to obtain 82 g (yield: 35%) of the intended compound (8).

Synthesis of compound (9):

140 g of the compound (8), 420 ml of xylene and 355.7 g of zinc (II) chloride were fed into a three-necked flask, and the obtained mixture was stirred under heating and reflux for 5 hours and then cooled to room temperature. An aqueous solution of 1.5 l of hexane and 626.4 g of sodium hydroxide in 900 ml of water was added to the reaction mixture, and the obtained mixture was stirred and then filtered by suction with Celite. The hexane layer of the obtained filtrate was concentrated with a rotary evaporator. The residue was purified by silica gel column chromatography to obtain 70.1 g (yield: 50%) of the intended compound (9).

Synthesis of compound (10):

10.0 g of the compound (9), 5.5 g of sodium iodide, 15.6 g of sodium hydrogencarbonate and 30 ml of N,N-dimethylacetamide were fed into a three-necked flask, and 9.3 ml of 2-(2-chloroethoxy)ethanol was dropped thereinto under stirring and heating at an outer temperature of 130° C. for a period of 10 minutes. After the completion of the dropping, the heating and stirring were continued for additional 3 hours and then the reaction mixture was cooled to room temperature. 200 ml of ethyl acetate and 200 ml of water were added thereto and the obtained mixture was stirred. After the extraction, the obtained ethyl acetate layer was washed with a mixed solution of 150 ml of water and 50 ml of saturated aqueous common salt solution four times and then dried over anhydrous sodium sulfate. The product thus obtained was concentrated with a rotary evaporator, and the residue was purified by silica gel column chromatography to obtain 10.0 g (yield: 64.5%) of the intended compound (10).

Synthesis of compound (11):

10.0 g of the compound (10), 39.4 g of sodium acetate, 27.4 ml of acetic acid and 30 ml of methanol were fed into a three-necked flask. The same diazonium salt solution as that obtained in the same manner as that in the synthesis of the compound (5) was added thereto under stirring and cooling with ice to keep the inner temperature not higher than 16° C. In this step, the reaction procedure was traced by TLC, and the addition of the diazonium salt solution was stopped when the compound (10) had disappeared in the reaction system. After the completion of the addition followed by stirring for 30 minutes, methanol was distilled off under reduced pressure. The reaction mixture was poured into ice and neutralized by adding a sodium hydroxide solution, and then 300 ml of ethyl acetate and 300 ml of water were added thereto to conduct the extraction. The obtained ethyl acetate layer was washed with a mixture of 200 ml of water and 100 ml of saturated aqueous common salt solution four times and then dried over anhydrous sodium sulfate. The product was concentrated with a rotary evaporator and the obtained residue was purified by silica gel column chromatography to obtain 9.5 g (yield: 56%) of the intended compound (11).

Synthesis of compound (D-40):

10.0 g of the compound (11), 0.5 g of palladium-carbon (10%) and 100 ml of methanol were fed into an autoclave and stirred at room temperature under a hydrogen pressure of 100 atm for 5 hours. A solution of 8.6 g of naphthalene-1,5-disulfonic acid tetrahydrate in 20 ml of methanol was added to the obtained reaction mixture. The resultant mixture was filtered and the filtrate was concentrated with a rotary evaporator. 200 ml of ethyl acetate and 200 ml of water were added to the concentrate, and the resultant mixture was stirred to obtain a solution, thereby forming layers. The aqueous layer was separated and washed with 200 ml of ethyl acetate three times. The aqueous layer thus obtained was concentrated with a rotary evaporator. Crystals separated from the solution in mixed methanol and ethanol were taken by filtration to obtain 10.0 g (yield: 75%) of the intended compound (D-40).

NMR($D_2O$): δ=8.86 (d, 2H, J=9.3 Hz), 8.21 (d, 2H, J=9.3 Hz), 7.72 (dd, 2H, J=9.3 Hz, 9.3 Hz), 7.47 (s, 1H), 7.32 (s, 2H), 2.8–3.9 (m, 10H), 1.9 to 2.1 (m, 1H), 1.7 to 1.9 (m, 1H), 1.42 (s, 3H), 1.28 (d, 3H, J=8.3 Hz), 1.16 (s, 3H).

Example 3

Compound (D-46) of the present invention shown above was synthesized according to the following reaction scheme:

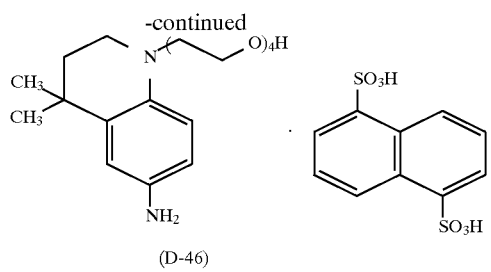

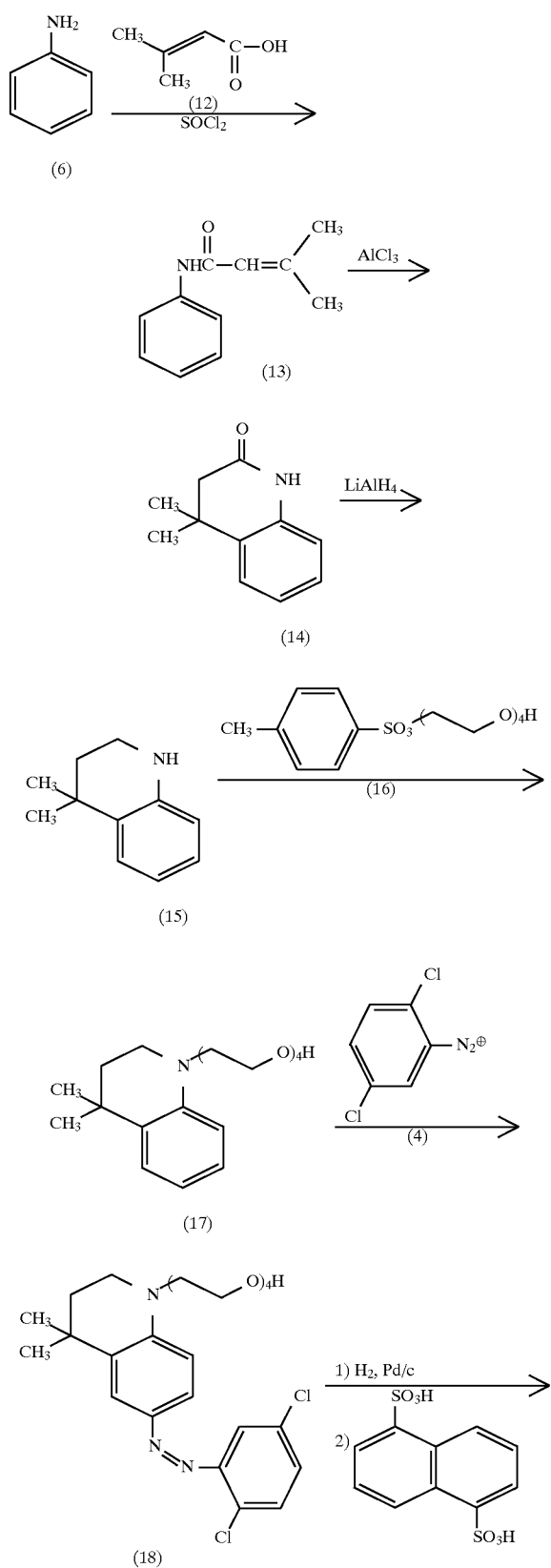

(D-46)

Synthesis of compound (13):

105.1 g of the compound (12), 200 ml of acetonitrile and 80 ml of N,N-dimethylacetamide were fed into a three-necked flask. 80.5 ml of thionyl chloride was dropped into the obtained mixture under stirring and cooling to an inner temperature of 12° C. or below. After the completion of the dropping followed by stirring for 1 hour, 93.1 g of aniline was dropped while the inner temperature was kept at 20° C. or below. After continuing the stirring for additional 10 minutes, 162 ml of pyridine was dropped while the inner temperature was kept at 18° C. or below. After continuing the stirring for additional 30 minutes, 1 l of water was added thereto, and the obtained mixture was stirred. The crystals thus formed were filtered by suction to obtain 161 g (yield: 92%) of the intended compound (13).

Synthesis of compound (14):

160 g of the compound (13) and 450 ml of methylene chloride were fed into a three-necked flask and then 266.6 g of aluminum (III) chloride was added thereto while keeping the inner temperature below 20° C. by cooling with ice. After the completion of the addition, the ice bath was taken out, the reaction mixture was stirred for 3 hours and then poured into ice/water. After extraction with 2 l of ethyl acetate, the obtained ethyl acetate layer was washed with a mixed solution of 800 ml of water and 200 ml of saturated aqueous common salt solution three times and then dried over anhydrous sodium sulfate. After the concentration with a rotary evaporator, 350 ml of acetonitrile was added to the residue, and the crystals thus obtained were filtered by suction to obtain 108 g (yield: 68%) of the intended compound (14).

Synthesis of compound (15):

25 g of lithium aluminum hydride and 400 ml of tetrahydrofuran were fed into a three-necked flask. A solution of 87.6 g of the compound (14) and 200 ml of tetrahydrofuran was dropped thereinto at such a rate that tetrahydrofuran was refluxed at a moderate speed under stirring. After the completion of the dropping, the stirring was continued under heating and reflux for additional one hour. 100 ml of ethyl acetate and then 100 ml of methanol were dropped thereinto. 1 l of ethyl acetate and 500 ml of water were added thereto and then a solution of 120 g of sodium hydroxide in 500 ml of water was added thereto. The reaction mixture was filtered by suction with Celite. Ethyl acetate layer separated from the filtrate was washed with a mixed solution of 400 ml of water and 100 ml of saturated aqueous common salt solution three times. The product was concentrated with a rotary evaporator to obtain the intended compound (15) as the crude product, which was then sent to the next step without purification.

Synthesis of compound (17):

20.0 g of the compound (15), 11.2 g of sodium iodide, 31.2 g of sodium hydrogencarbonate and 65 ml of N,N-dimethylacetamide were fed into a three-necked flask, and 52.3 g of the compound (16) (synthesized from tetraethylene glycol and p-toluenesulfonyl chloride) was dropped thereinto under stirring and heating at an outer temperature of 80° C. for a period of 1 hour. After the completion of the dropping, the heating and stirring were continued for additional 5 hours and then the reaction mixture was cooled to room temperature. 500 ml of ethyl acetate and 500 ml of water were added thereto. After the extraction, the obtained ethyl acetate layer was washed with a mixed solution of 400 ml of water and 100 ml of saturated aqueous common salt solution four times and then dried over anhydrous sodium sulfate. The product thus obtained was concentrated with a rotary evaporator, and the residue was purified by silica gel column chromatography to obtain 39.4 g (yield: 94%) of the intended compound (17).

Synthesis of compound (18):

39.0 g of the compound (17), 114 g of sodium acetate, 79 ml of acetic acid and 140 ml of methanol were fed into a three-necked flask. The same diazonium salt solution as that obtained in the same manner as that in the synthesis of the compound (5) was added thereto under stirring and cooling with ice to keep the inner temperature not higher than 14° C. In this step, the reaction procedure was traced by TLC, and the addition of the diazonium salt solution was stopped when the compound (17) had disappeared from the reaction system. After the completion of the addition followed by stirring for 30 minutes, methanol was distilled off under reduced pressure. The reaction mixture was poured into ice and neutralized by adding a sodium hydroxide solution, and then 800 ml of ethyl acetate and 700 ml of water were added thereto to conduct the extraction. The obtained ethyl acetate layer was washed with a mixture of 400 ml of water and 100 ml of saturated aqueous common salt solution four times and then dried over anhydrous sodium sulfate. The product was concentrated with a rotary evaporator and the obtained residue was purified by silica gel column chromatography to obtain 30.0 g (yield: 51%) of the intended compound (18).

Synthesis of compound (D-46):

30.0 of the compound (18), 1.5 g of palladium-carbon (10%) and 250 ml of methanol were fed into an autoclave and stirred at room temperature under a hydrogen pressure of 100 atm for 5 hours. A solution of 21.2 g of naphthalene-1,5-disulfonic acid tetrahydrate in 50 ml of methanol was added to the obtained reaction mixture. The resultant mixture was filtered and the filtrate was concentrated with a rotary evaporator. 200 ml of ethyl acetate and 200 ml of water were added to the concentrate, and the resultant mixture was stirred to obtain a solution, thereby forming layers. The aqueous layer was separated and washed with 200 ml of ethyl acetate three times. The aqueous layer thus obtained was concentrated with a rotary evaporator to obtain 35.5 g (yield: 94%) of the intended compound (D-46).

NMR($D_2O$): δ=8.83 (d, 2H, J=9.3 Hz), 8.20 (d, 2H, J=9.3 Hz), 7.71 (dd, 2H, J=9.3 Hz, 9.3 Hz), 7.49 (s, 1H), 7.28 (s, 2H), 3.4–3.8 (m, 21H), 1.9 to 2.1 (m, 1H), 1.22 (s, 6H).

Example 4

Compound (D-48) of the present invention shown above was synthesized according to the following reaction scheme:

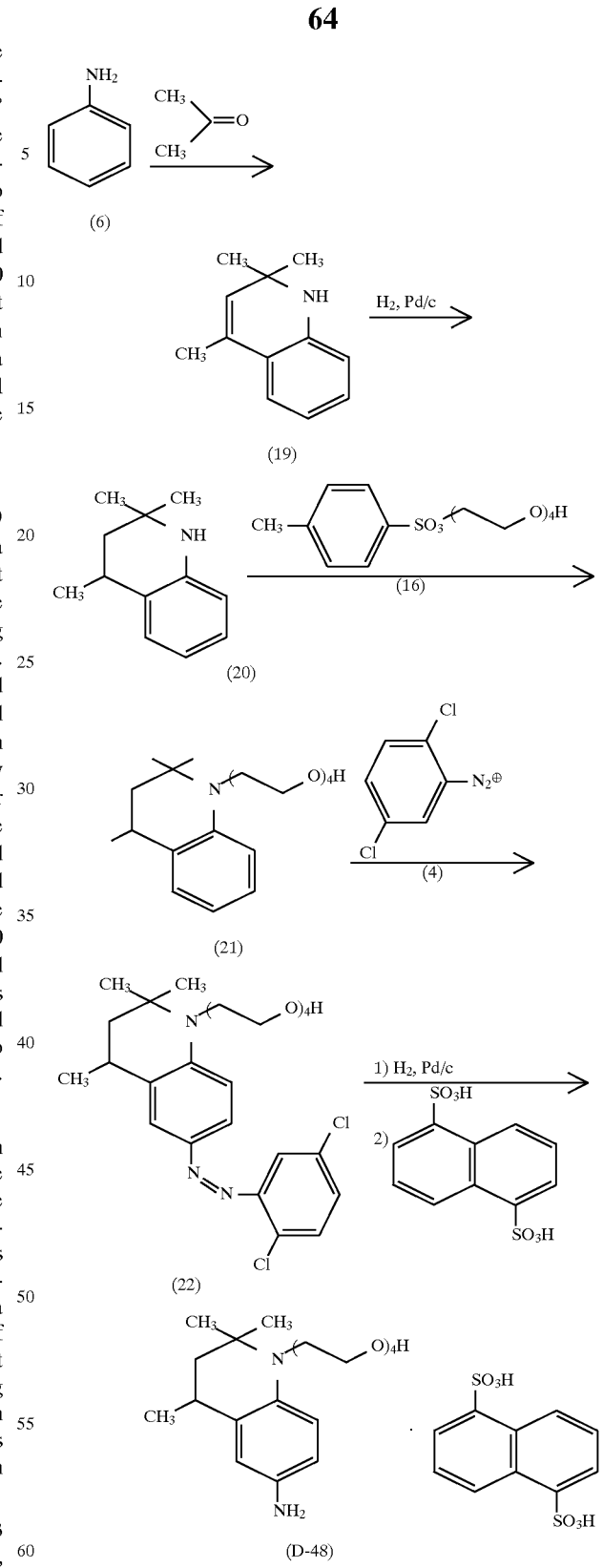

Synthesis of compound (19):

232.8 g of aniline and 7.6 g of iodine were fed into a three-necked flask. 734 ml of acetone was dropped into the resultant mixture under stirring and under heating to an outer temperature of 200° C. for a period of 6 hours. Low-boiling components such as water formed in the reaction system were collected in a cooling device fixed on a branch pipe and distilled off. After the completion of the dropping, the obtained reaction mixture was distilled to obtain 142 g (yield: 33 g) of the intended compound (19).

b.p.: 138° to 142° C./16 mmHg.

Synthesis of compound (20):

142 g of the compound (19), 10 g of palladium-carbon (10%) and 450 ml of ethanol were fed into an autoclave and stirred at room temperature under a hydrogen pressure of 100 atm for 5 hours. After the completion of the stirring followed by the filtration, the filtrate was concentrated with a rotary evaporator to obtain 144 g of the intended compound (20) as the crude product, which was then sent to the next step without purification.

Synthesis of compound (21)

70.1 g of the compound (20), 60.0 g of sodium iodide, 134.4 g of sodium hydrogencarbonate and 250 ml of N,N-dimethylacetamide were fed into a three-necked flask. 278.9 g of the compound (16) (synthesized from tetraethylene glycol and p-toluenesulfonyl chloride) was dropped thereinto for a period of 1 hour. After the completion of the dropping followed by heating and stirring for additional 5 hours, the reaction mixture was cooled to room temperature. 1 l of ethyl acetate and 1 l of water were added to the reaction mixture to conduct the extraction. The obtained ethyl acetate layer was washed with a mixed solution of 800 ml of water and 200 ml of saturated aqueous common salt solution four times, and then dried over anhydrous sodium sulfate. The product was concentrated with a rotary evaporator and the obtained residue was purified by silica gel column chromatography to obtain 64.7 g (yield: 46%) of the intended compound (21).

Synthesis of compound (22):

36.7 g of the compound (21), 85 g of sodium acetate and 59 ml of acetic acid were fed into a three-necked flask. The same diazonium salt solution as that obtained in the same manner as that in the synthesis of the compound (5) was added thereto under stirring and cooling with ice to keep the inner temperature not higher than 15° C. In this step, the reaction procedure was traced by TLC, and the addition of the diazonium salt solution was stopped when the compound (22) had disappeared from the reaction system. After the completion of the addition followed by stirring for 30 minutes, methanol was distilled off under reduced pressure. The reaction mixture was poured into ice and neutralized by adding a sodium hydroxide solution, and then 2 l of ethyl acetate and 1 l of water were added thereto to conduct the extraction. The obtained ethyl acetate layer was washed with a mixture of 800 ml of water and 200 ml of saturated aqueous common salt solution four times and then dried over anhydrous sodium sulfate. The product was concentrated with a rotary evaporator and the obtained residue was purified by silica gel column chromatography to obtain 25.8 g (yield: 47%) of the intended compound (22).

Synthesis of the compound (D-48):

25.8 g of the compound (22), 2 g of palladium-carbon (10%) and 73 ml of methanol were fed into an autoclave and stirred at room temperature under a hydrogen pressure of 100 atm for 3 hours. A solution of 17.7 g of naphthalene-1,5-disulfonic acid tetrahydrate in 40 ml of methanol was added to the obtained reaction mixture. The resultant mixture was filtered and the filtrate was concentrated with a rotary evaporator. 200 ml of ethyl acetate and 200 ml of water were added to the concentrate to obtain a solution which formed layers. The aqueous layer was separated and washed with 200 ml of ethyl acetate three times. The aqueous layer thus obtained was concentrated with a rotary evaporator to obtain 20.9 g (yield: 65%) of the intended compound (D-48).

NMR(D$_2$O): δ=8.86 (d, 2H, J=9.7 Hz), 8.21 (d, 2H, J=9.7 Hz), 7.72 (dd, 2H, J=9.7 Hz, 9.7 Hz), 7.50 (d, 2H, J=13.8 Hz), 7.38 (s, 1H), 2.8–3.8 (m, 20H), 1.7 to 2.1 (m, 2H), 1.30 (s, 3H), 1.22 (d, 3H, J=9.7 Hz), 1.12 (s, 3H).

Example 5

Compound (D-91) of the present invention shown above was synthesized according to the following reaction scheme:

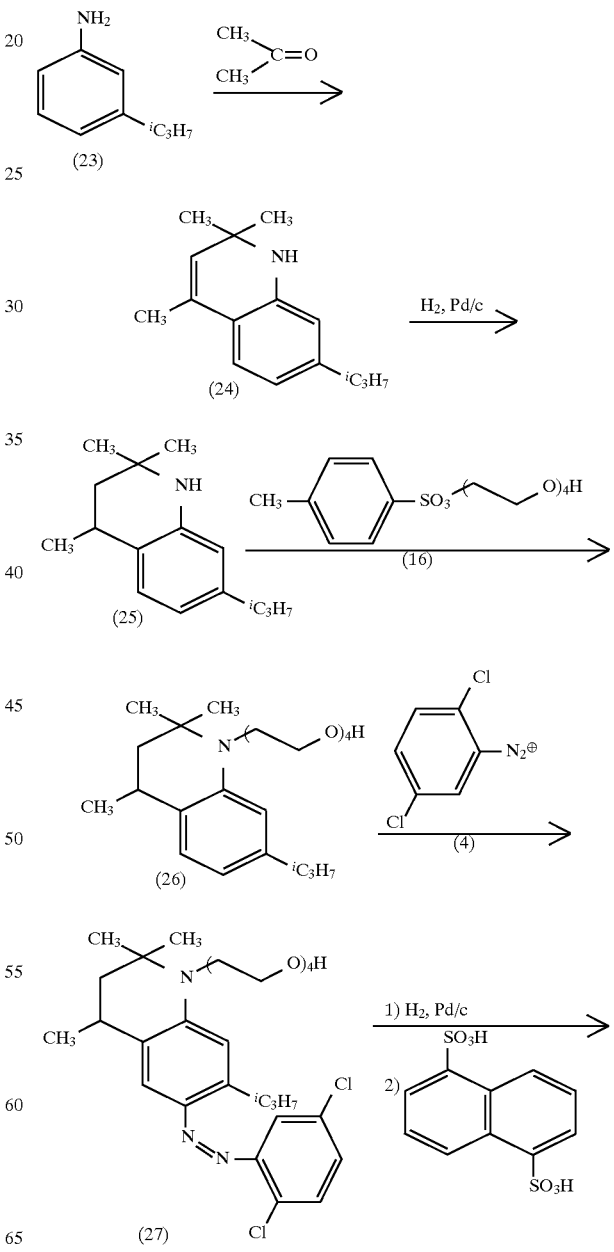

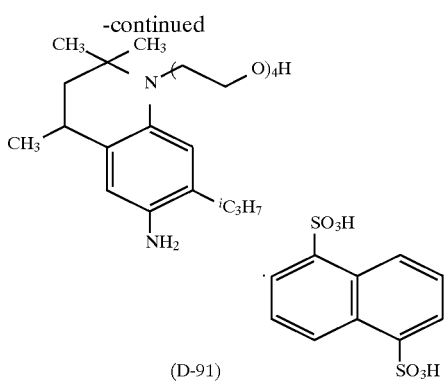

Synthesis of compound (24):

The compound (24) was obtained from 3-isopropylaniine in the same manner as that in the synthesis of the compound (19).

b. p.: 160° to 165° C./12 mmHg.

Synthesis of compound (25):

The compound (25) was obtained from compound (24) in the same manner as that in the synthesis of the compound (20).

Synthesis of compound (26):

26.1 g of the compound (25), 18.0 g of sodium iodide, 30.2 g of sodium hydrogencarbonate and 75 ml of N,N-dimethylacetamide were fed into a three-necked flask, and 62.7 g of the compound (16) was dropped into the resultant mixture under stirring and heating at an outer temperature of 130° C. for a period of 1 hour. after continuing the stirring and heating for additional 5 hours, 31.4 g of the compound (16) was dropped thereinto for a period of 1 hour. After the completion of the dropping followed by stirring under heating for 3 hours, the reaction mixture was cooled to room temperature. 700 ml of ethyl acetate and 500 ml of water were added thereto to conduct the extraction. The obtained ethyl acetate layer was washed with a mixed solution of 400 ml of water and 100 ml of saturated aqueous common salt solution, and then dried over anhydrous sodium sulfate. The product thus obtained was concentrated with a rotary evaporator, and the residue was purified by silica gel column chromatography to obtain 30.4 g (yield: 64%).

Synthesis of compound (27):

30.4 g of the compound (26), 63 g of sodium acetate, 44 ml of acetic acid and 400 ml of methanol were fed into a three-necked flask. The same diazonium salt solution as that obtained in the same manner as that in the synthesis of the compound (5) was added thereto under stirring and cooling with ice to keep the inner temperature not higher than 15° C. After confirming that the compound (26) had disappeared by TLC, the addition of the diazonium salt solution was stopped, and the stirring was continued for additional 30 minutes. Methanol was distilled off under reduced pressure. The reaction mixture was poured into ice and neutralized by adding a sodium hydroxide solution, and then 1.5 l of ethyl acetate and 1 l of water were added thereto to conduct the extraction. The obtained ethyl acetate layer was washed with a mixture of 800 ml of water and 200 ml of saturated aqueous common salt solution four times and then dried over anhydrous sodium sulfate. The product was concentrated with a rotary evaporator and the obtained residue was purified by silica gel column chromatography to obtain 30.0 g (yield: 68%) of the intended compound (27).

Synthesis of compound (D-91):

30.0 g of the compound (27), 3 g of palladium-carbon (10%) and 70 ml of methanol were fed into an autoclave and stirred at room temperature under a hydrogen pressure of 100 atm for 7 hours. A solution of 19.1 g of naphthalene-1,5-disulfonic acid tetrahydrate in 40 ml of methanol was added to the obtained reaction mixture. The resultant mixture was filtered and the filtrate was concentrated with a rotary evaporator. 200 ml of ethyl acetate and 200 ml of water were added to the concentrate to obtain a solution. The aqueous layer thus obtained was separated and then washed with 200 ml of ethyl acetate three times. The aqueous layer thus obtained was concentrated with a rotary evaporator to obtain 35.1 g (yield: 95%) of the intended compound (D-91).

NMR(D$_2$O): δ=8.88 (d, 2H, J=9.7 Hz), 8.21 (D, 2H, J=9.7 Hz), 7.72 (dd, 2H, J=9.7 Hz, 9.7 Hz), 7.34 (s, 1H), 7.28 (s, 1H), 2.7 to 3.8 (m, 21H), 1.7 to 2.1 (m, 2H), 1.45 (s, 3H), 1.1 to 1.3 (m, 12H).

Example 6

Compound (D-86) of the present invention shown above was synthesized according to the following reaction scheme:

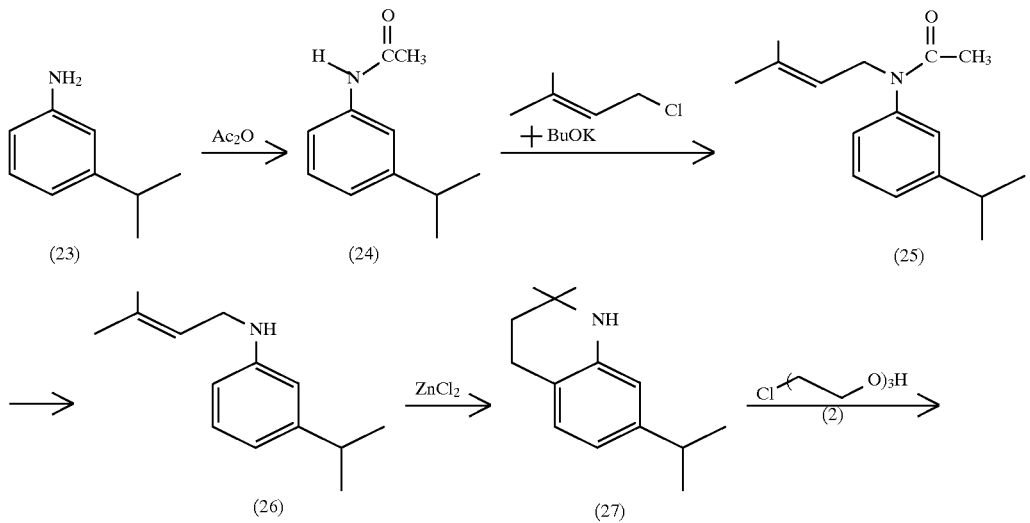

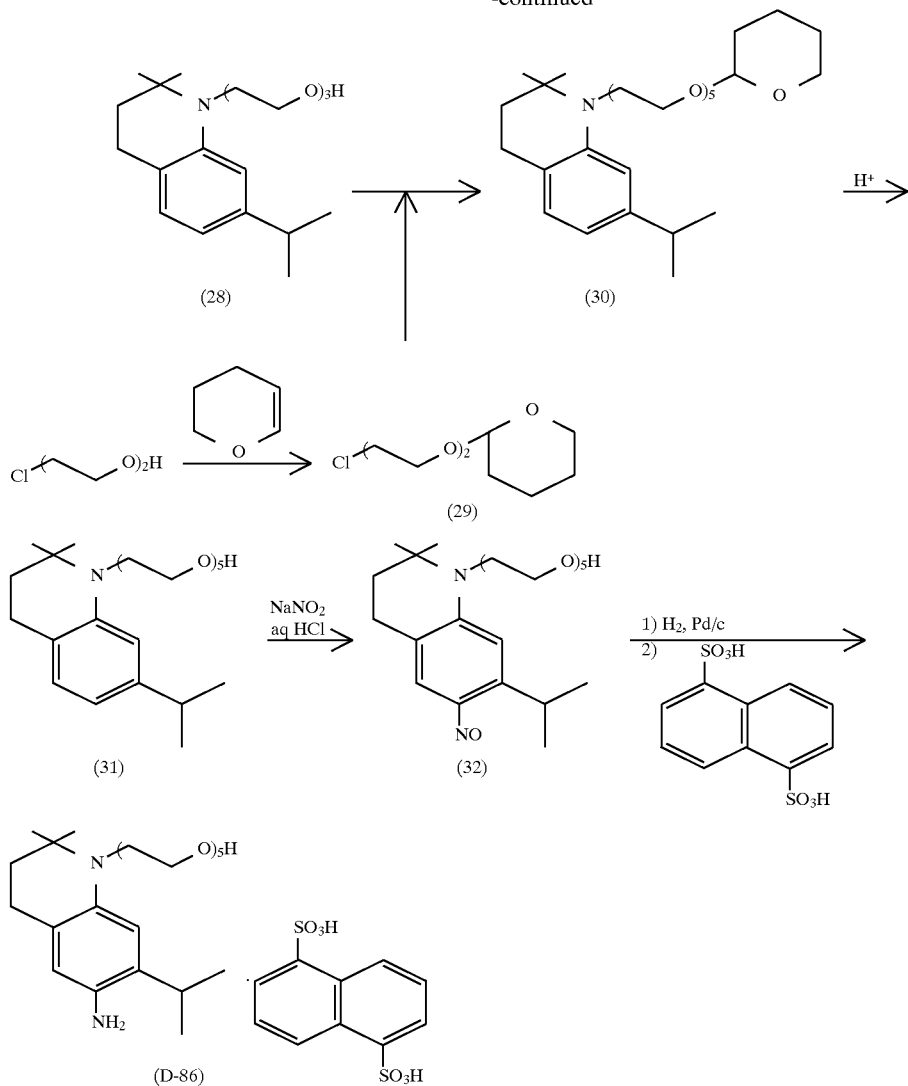

Synthesis of compound (24):

472 ml of acetic anhydride was fed into a three-necked flask. 270.4 g of the compound (23) was dropped thereinto under refluxing and heating with stirring for a period of 30 minutes. After the completion of the dropping followed by stirring under heating and refluxing for 3 hours, 90 ml of water was dropped thereinto for a period of 15 minutes. The reaction mixture was cooled to an inner temperature of 30° C. 1 l of ethyl acetate and 1 l of water were added to the mixture and the extraction was conducted. The ethyl acetate layer thus obtained was washed with a mixture of 800 ml of water and 200 ml of saturated aqueous common salt solution 3 times, and then dried over anhydrous sodium sulfate. The product was concentrated with a rotary evaporator to obtain 390 g of the intended compound (24) as the crude product, which was then sent to the next step without purification.

Synthesis of compound (25):

1 l of N,N-dimethylacetamide was added to the compound (24) to dissolve the compound. 246.9 g of potassium-t-butoxy was added thereto at the room temperature followed by stirring for 1 hour. The mixture was cooled to the inner temperature of −5° C. in ice-methanol bath. 247.9 ml of prenyl chloride was dropped thereinto under stirring for a period of 1 hour. The inner temperature was raised to 7° C. After the completion of the dropping followed by stirring for additional 2 hours, 2 l of ethyl acetate and 1.5 l of water were added to the mixture and the extraction was conducted. The ethyl acetate layer thus obtained was washed with a mixture of 1 l of water and 200 ml of saturated aqueous common salt solution 4 times, and then dried over anhydrous sodium sulfate. The product was concentrated with a rotary evaporator to obtain the intended compound (25) as the crude product, which was then sent to the next step without purification.

Synthesis of compound (26):

1.2 l of ethanol was added to the compound (25) to dissolve the compound. A solution of 320 g of sodium hydroxide in 320 ml of water was dropped thereinto for a period of 20 minutes under heating and refluxing. The reaction mixture was refluxed for additional 3 hours under heating. Another solution of 320 g of sodium hydroxide in 320 ml of water was dropped thereinto for a period of 20 minutes. The mixture was refluxed again under heating for additional 3 hours. A solution of 160 g of sodium hydroxide in 160 ml of water was dropped thereinto for a period of 5 minutes. After the mixture was refluxed under heating and stirring, the solvent was distilled off under the reduced pressure, 1544 ml of the concentrated hydrochloric acid was dropped thereinto cooling with ice for a period of 1 hour. The inner temperature was raised to 30° C. 1.5 l of ethyl acetate was added to the mixture and the extraction was conducted. The ethyl acetate layer thus obtained was washed with a mixture of 1 l of water and 200 ml of saturated aqueous common salt solution 4 times, and then dried over anhydrous sodium sulfate. The product was concentrated with a rotary evaporator and the obtained residue was purified by silica gel column chromatography to obtain 305.7 g (yield: 75%) of the intended compound (26) as oil.

Synthesis of compound (27):

305.7 g of the compound (26) and 500 ml of xylene were fed into a three-necked flask. 613 g of zinc (II) chloride was added thereto with stirring and then the mixture was refluxed under heating and stirring for 3 hours. The reaction mixture was cooled to the temperature of 70° C. 1.5 l of ethyl acetate and 1.5 l of water were added to the mixture and the extraction was conducted. The ethyl acetate layer thus obtained was washed with a solution of 80 g of sodium hydroxide in 1 l of water 3 times, then washed again with a mixture of 200 ml of saturated aqueous common salt solution and 800 ml of water 3 times. The ethyl acetate layer was dried over anhydrous sodium sulfate. The product was concentrated with a rotary evaporator and the obtained residue was purified by silica gel column chromatography to obtain 174.2 g (yield: 57%) of the intended compound (27) as oil.

Synthesis of compound (28):

87.1 g of the compound (27), 288 g of sodium bicarbonate, 64.2 g of sodium iodide and 200 ml of N,N-dimethylacetamide were fed into a three-necked flask. The mixture was stirred at the inner temperature of 120° C. under heating. 145 g of the compound (2) was dropped thereinto for a period of 1 hour. After the completion of the dropping, the heating and stirring were continued for additional 13 hours at 130° C. and then the reaction mixture was cooled to 30° C. 600 ml of ethyl acetate and 500 ml of water were added thereto and the extraction was conducted. The thus-obtained ethyl acetate layer was washed with a mixed solution of 100 ml of saturated aqueous common salt solution and 400 ml of water four times and then dried over anhydrous sodium sulfate. The product thus obtained was concentrated with a rotary evaporator, and the residue was purified by silica gel column chromatography to obtain 84.6 g (yield: 59%) of the intended compound (28) as oil.

Synthesis of compound (29):

249 g of 2-(2-chloroethoxy) ethanol, 3.8 g of p-toluenesulfonic acid monohydrate and 590 ml of dichloromethane were fed into a three-necked flask. 500 ml of dihydropyran was dropped thereinto for a period of 30 minute at room temperature with stirring. The temperature of the reaction system was raised as the dropping, and then the mixture reached reflux state. After the completion of the dropping, the stirring was continued for additional 3 hours and then 10 g of sodium bicarbonate was added thereto followed by stirring for additional 10 minutes. The reaction mixture was poured into a mixture of 100 g of sodium bicarbonate and ice-water. 590 ml of dichloromethane added thereto and the extraction was conducted. The thus-obtained dichloromethane layer was washed with a mixed solution of 100 ml of saturated aqueous common salt solution and 400 ml of water four times and then dried over anhydrous sodium sulfate. 4 g of sodium hydroxide was added thereto and the product thus obtained was concentrated with a rotary evaporator. The residue was distilled to collect the fraction of from 88° C. to 100° C./0.2 mmHg to obtain 350 g (yield: 84%) of the intended compound (29).

Synthesis of compound (30):

84.1 g of the compound (28), 14.06 g of sodium hydroxide and 200 ml of toluene were fed into a three-necked flask. 131 g of the compound (29) was dropped thereinto under refluxing and heating with stirring for a period of 2 hours. After the completion of the dropping followed by stirring under heating and refluxing for additional 30 minutes, toluene was distilled off under the reduced pressure. 500 ml of dichloromethane and 300 ml of water were added thereto to dissolve them. 250 ml of concentrated hydrochloric acid was added thereto with stirring to make the mixture acidic and then the mixture was neutralized by adding sodium bicarbonate thereto. The dichloromethane layer obtained by the extraction of the mixture was washed with a mixed solution of 100 ml of saturated aqueous common salt solution and 400 ml of water 3 times and then dried over anhydrous sodium sulfate. The product thus obtained was concentrated with a rotary evaporator to obtain the intended compound (30) as the crude product, which was then sent to the next step without purification.

Synthesis of compound (31):

500 ml of methanol was added to the compound (30) to dissolve the compound. 21.5 ml of the concentrated hydrochloric acid was dropped thereinto and then stirred for 1 hour. The solvent was distilled off under the reduced pressure, 500 ml of ethyl acetate and 300 ml of water were added thereto and then the mixture was neutralized by adding sodium bicarbonate thereto. The ethyl acetate layer obtained by the extraction of the mixture was washed with a mixed solution of 50 ml of saturated aqueous common salt solution and 300 ml of water 4 times and then dried over anhydrous sodium sulfate. The product thus obtained was concentrated with a rotary evaporator. The residue was purified by silica gel column chromatography to obtain 84.7 g (yield: 80%) of the intended compound (31) as oil.

Synthesis of compound (32):

84.7 g of the compound (31), 56.6 ml of the concentrated hydrochloric acid and 400 ml of methanol were fed into a three-necked flask. A aqueous solution of 19.3 g of sodium nitrite in 20 ml of water was dropped thereinto under stirring for a period of 15 minutes cooling with ice. After the stirring for additional 5 hours without the ice bath, the reaction mixture was mixed with 100 g of sodium bicarbonate. 500 ml of ethyl acetate and 300 ml of water were added to the mixture and the extraction was conducted. The ethyl acetate layer thus obtained was washed with a mixed solution of 50 ml of saturated aqueous common salt solution and 150 ml of water 3 times and then dried over anhydrous sodium sulfate. The product thus obtained was concentrated with a rotary evaporator. The residue was purified by silica gel column chromatography to obtain 44.6 g (yield: 49%) of the intended compound (32) as oil.

Synthesis of compound (D-86):

44.6 g of the compound (32), 5 g of the palladium-carbon (10%) and 100 ml of methanol were fed into an autoclave and stirred at room temperature under a hydrogen pressure of 100 atm for 3 hours. A solution of 35.5 g of naphthalene-1,5-disulfonic acid tetrahydrate in 90 ml of methanol was added to the obtained reaction mixture. The resultant mixture was filtered and the filtrate was stirred to precipitate a crystal. 58.5 g of the intended compound (D-86) was obtained (yield: 82%).

NMR($D_2O$) δ=8.86 (d, 2H, J=9.7 Hz), 8.21 (d, 2H, J=9.7 Hz), 7.72 (dd, 2H, J=9.7 Hz 9.7 Hz), 7.22 (s, 1H), 3.0–3.9 (m, 23H), 2.80 (t, 2H, J=8.0 Hz), 1.95 (t, 2H, J=8.0 Hz), 1.30 (s, 6H), 1.21 (d, 6H, J=8.4 Hz).

Example 7

Compound (D-70) of the present invention shown above was synthesized according to the following reaction scheme:

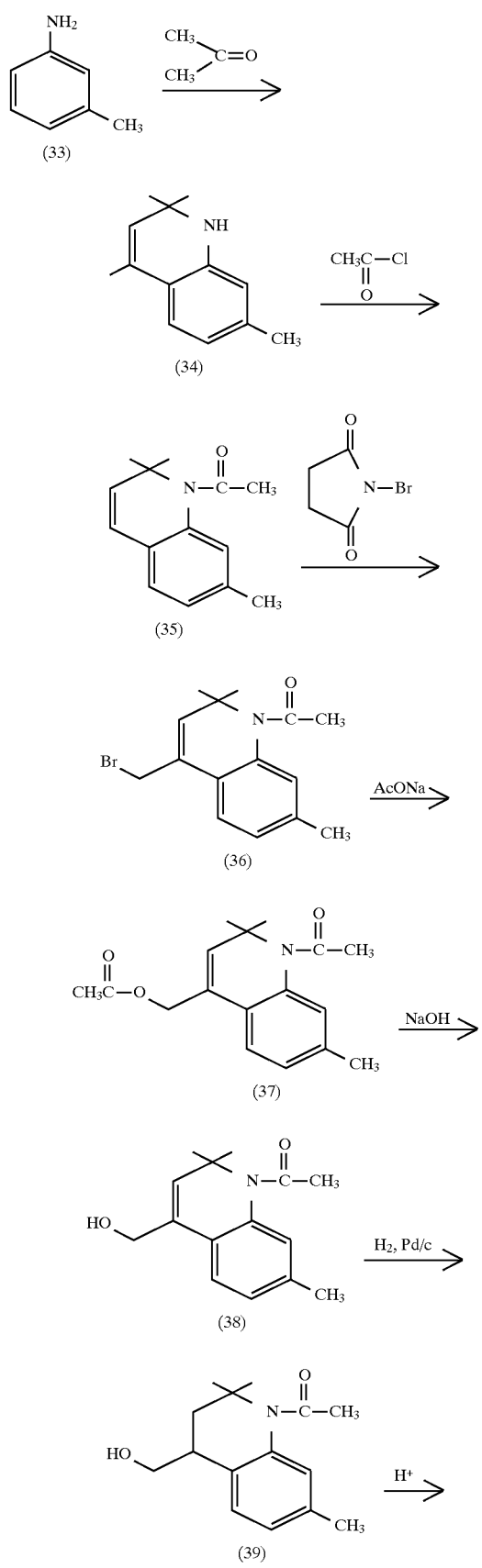

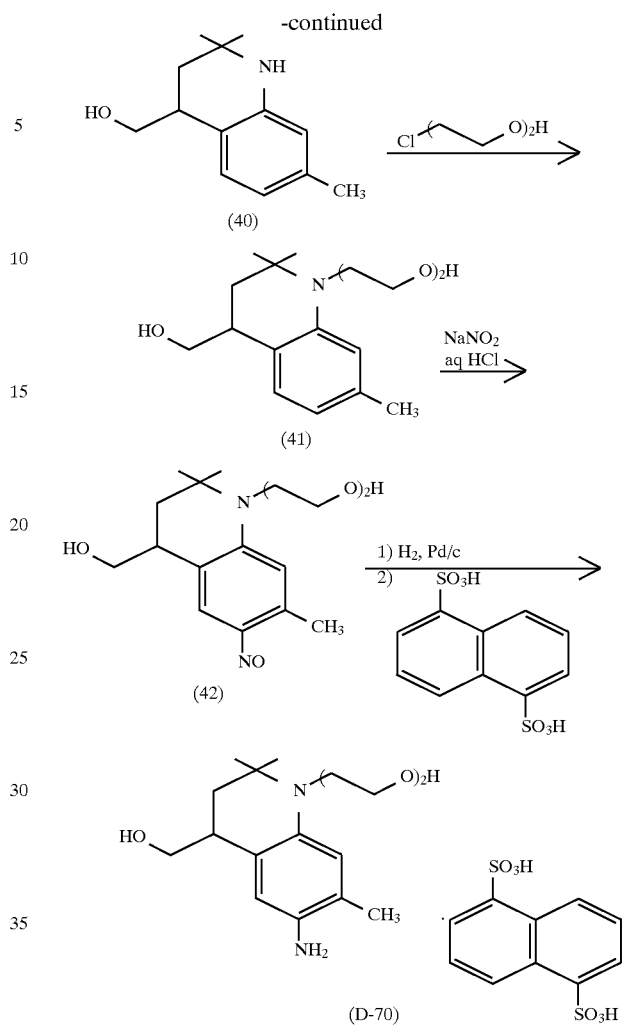

Synthesis of compound (34):

The intended compound (34) was obtained by the same manner as that in the synthesis of the compound (19) as a starting material of m-toluidine: m.p., 152°–156° C./15 mmHg.

Synthesis of compound (35):

416.9 g of the compound (34), 1.2 l of N,N-dimethylacetamide were fed into a three-necked flask. 190 ml of acetyl chloride was dropped into the thus-obtained mixture under stirring and cooling with ice for a period of 30 minutes. After 216 ml of pyridine was dropped substantially for a period of 1 hour, the reaction mixture was stirred for additional 3 hours without a ice bath. 2 l of ethyl acetate and 2 l of water were added to the mixture and the extraction was conducted. The ethyl acetate layer thus obtained was washed with a mixed solution of 500 ml of saturated aqueous common salt solution and 1.5 l of water 4 times and then dried over anhydrous sodium sulfate. The product thus obtained was concentrated with a rotary evaporator. The residue was purified by silica gel column chromatography to obtain 462 g (yield: 90%) of the intended compound (34) as oil.

Synthesis of compound (36):

462 g of the compound (34) and 1.5 l dichloromethane were fed into a three-necked flask. 393.5 g of N-bromosuccinimide was dropped into the thus-obtained mixture under stirring cooling with ice for a period of 1 hour maintaining the inner temperature of 15° C. or below. After the completion of the dropping followed by stirring for additional 1 hour, 1 l of water was added to the mixture and the extraction was conducted. The dichloromethane layer thus obtained was washed with a mixed solution of 500 ml of saturated aqueous common salt solution and 1 l of water 4 times and then dried over anhydrous sodium sulfate. The product thus obtained was concentrated with a rotary evaporator. 1 l of acetonitrile was added to the resulting residue followed by stirring, and subjecting the precipitated crystals to filtration under reduced pressure to obtain 347.5 g (yield: 56%) of the intended compound (36).

Synthesis of compound (37):

308.25 g of the compound (36), 600 ml of N,N-dimethylacetamide and 246 g of sodium acetate were fed into a three-necked flask, and the thus-obtained mixture was stirred under heating and refluxing for 2 hours and then cooled to 30° C. 1.25 l of water was dropped into the reaction mixture, and the thus-obtained crystals were taken by filtration under reduced pressure. After 400 ml of acetonitrile was added to the crystals followed by dissolution under stirring, then cooling with water, the crystals precipitated were taken by filtration under reduced pressure to obtain 244.3 g (yield: 85%) of the intended compound (37).

Synthesis of compound (38):

244.3 g of the compound (37) and 250 ml of tetrahydrofuran were fed into a three-necked flask to dissolve the compound, and 1 l of ethanol was added thereto. A solution of 136 g of sodium hydoxide in 150 ml of water was then added to the mixture under stirring. After substantial stirring for 1 hour, the solvent was distilled off under the reduced pressure. The reaction mixture was made to acidic by adding 292 ml of the concentrated hydrochloric acid, and then 800 ml of ethyl acetate and 400 ml of water was added thereto and stirred. The mixture was neutralized by adding sodium bicarbonate thereto. The ethyl acetate layer obtained by the extraction of the mixture was washed with a mixed solution of 100 ml of saturated aqueous common salt solution and 400 ml of water 4 times and then dried over anhydrous sodium sulfate. The product thus obtained was concentrated with a rotary evaporator to obtain the intended compound (38) as the crude product, which was then sent to the next step without purification.

Synthesis of compound (39):

The compound (38), 20 g of the palladium-carbon (10%) and 400 ml of ethanol were fed into an autoclave and stirred at the inner temperature of 50°–60° C. under a hydrogen pressure of 100 atm for 5 hours. The reaction mixture was filtered and the filtrate was concentrated with a rotary evaporator to obtain the intended compound (39) as the crude product, which was then sent to the next step without purification.

Synthesis of compound (40):

The compound (39) and 500 ml of ethanol were fed into a three-necked flask. 146 ml of the concentrated hydrochloric acid was added thereto under stirring and then the mixture was refluxed under heating and stirring. 96 ml of sulfuric acid was dropped thereinto for a period of 10 minutes followed by refluxing under the heating and stirring for additional 1 hour. The reaction mixture was cooled to 30° C. and then mixed with 1 kg of sodium bicarbonate to neutralise it. 1 l of ethyl acetate and 1 l of water was added thereto and the extraction was conducted. The thus-obtained ethyl acetate layer was washed with a mixed solution of 200 ml of saturated aqueous common salt solution and 800 ml of water four times and then dried over anhydrous sodium sulfate. The product thus obtained was concentrated with a rotary evaporator. Ethyl acetate and n-hexane were added to the residue and the thus-obtained crystals were subjected to filtration under reduced pressure to obtain 125.7 g (yield: 72%) of the intended compound (40).

Synthesis of compound (41):

58.0 g of the compound (40), 70.6 g of sodium bicarbonate, 25.5 g of sodium iodide and 100 ml of N,N-dimethylacetamide were fed into a three-necked flask. The mixture was stirred at the outer temperature of 130° C. under heating. 42.4 g of 2-(2-chloroethoxy) ethanol was dropped thereinto for a period of 20 minutes. After the completion of the dropping, the mixture was refluxed under heating and stirring for additional 5 hours. The reaction mixture was cooled to 30° C. with water. 500 ml of ethyl acetate and 400 ml of water were added thereto and the extraction was conducted. The thus-obtained ethyl acetate layer was washed with a mixed solution of 100 ml of saturated aqueous common salt solution and 300 ml of water four times and then dried over anhydrous sodium sulfate. The product thus obtained was concentrated with a rotary evaporator, and the residue was purified by silica gel column chromatography to obtain 41.6 g (yield: 51%) of the intended compound (41).

Synthesis of compound (42):

41.0 g of the compound (41), 40.4 ml of the concentrated hydrochloric acid and 80 ml of methanol were fed into a three-necked flask. A solution of 13.8 g of sodium nitrite in 28 ml of water was dropped thereinto for a period of 15 minutes under stirring and cooling with ice. The mixture was stirred for additional 5 hours without cooling, and then mixed with 50 g of sodium bicarbonate. 500 ml of ethyl acetate and 300 ml of water were added thereto and the extraction was conducted. The thus-obtained ethyl acetate layer was washed with a mixed solution of 50 ml of saturated aqueous common salt solution and 150 ml of water 3 times and then dried over anhydrous sodium sulfate. The product thus obtained was concentrated with a rotary evaporator, and the residue was purified by silica gel column chromatography to obtain 38.0 g (yield: 84%) of the intended compound (42) as oil.

Synthesis of compound (D-70):

19.0 g of the compound (42), 0.5 g of the palladium-carbon (10%) and 100 ml of methanol were fed into an autoclave and stirred at room temperature under a hydrogen pressure of 100 atm for 3 hours. A solution of 21.6 g of naphthalene-1,5-disulfonic acid tetrahydrate in 45 ml of methanol was added to the thus-obtained reaction mixture. The resultant mixture was filtered and the filtrate was stirred to precipitate a crystal. 31.5 g of the intended compound (D-70) was obtained (yield: 90%).

NMR($D_2O$): δ=8.86 (d, 2H, J=9.7 Hz), 8.21 (d, 2H, J=9.7 Hz), 7.72 (dd, 2H, J=9.7 Hz, 9.7 Hz), 7.45 (s, 1H), 7.24 (s, 1H), 3.2–4.0 (m, 14H), 2.8–3.1 (m, 1H), 2.36 (s, 3H), 1.8–2.3 (m, 2H), 1.50 (s, 3H), 1.10 (s, 3H).

Example 8

Preparation of multi-layer color photosensitive material:

A multilayer color photosensitive material, which will be referred to as "sample 101", was prepared by forming layers of the following compositions:

(Compositions of photosensitive layers)

Main materials to be used for forming the layers are classified as follows:

ExC: cyan coupler
ExM: magenta coupler
ExY: yellow coupler
ExS: sensitizing dye
UV: ultraviolet absorber
HBS: high-boiling organic solvent H: gelatin hardener The numerals for the respective components indicate the amount of coating given by g/m². Those for silver halides are given in terms of silver. Those for sensitizing dyes are given in terms of molar unit per mol of the silver halide contained in the same layer.

(Sample 101)

The first layer (antihalation layer):

| | |
|---|---|
| Black colloidal silver | silver 0.18 |
| Glatin | 1.60 |
| ExM-1 | 0.11 |
| ExF-1 | $3.4 \times 10^{-3}$ |
| ExF-2 (solid dispersed dye) | 0.03 |
| ExF-3 (solid dispersed dye) | 0.04 |
| HBS-1 | 0.16 |

The second layer (intermediate layer):

| | |
|---|---|
| ExC-2 | 0.055 |
| UV-1 | 0.011 |
| UV-2 | 0.030 |
| UV-3 | 0.053 |
| HBS-1 | 0.05 |
| HBS-2 | 0.02 |
| Polyethyl acrylate latex | $8.1 \times 10^{-2}$ |
| Gelatin | 1.75 |

The third layer (low-speed red-sensitive emulsion layer)

| | |
|---|---|
| Silver bromoiodide emulsion A | silver 0.46 |
| ExS-1 | $5.0 \times 10^{-4}$ |
| ExS-2 | $1.8 \times 10^{-5}$ |
| ExS-3 | $5.0 \times 10^{-4}$ |
| ExC-1 | 0.16 |
| ExC-3 | 0.045 |
| ExC-5 | 0.0050 |
| ExC-7 | 0.001 |
| ExC-8 | 0.010 |
| Cpd-2 | 0.005 |
| HBS-1 | 0.090 |
| Gelatin | 0.87 |

The fourth layer (medium-speed red-sensitive emulsion layer)

| | |
|---|---|
| Silver bromoiodide emulsion D | silver 0.70 |
| ExS-1 | $3.0 \times 10^{-4}$ |
| ExS-2 | $1.2 \times 10^{-5}$ |
| ExS-3 | $4.0 \times 10^{-4}$ |
| ExC-1 | 0.22 |
| ExC-2 | 0.055 |
| ExC-5 | 0.007 |
| ExC-8 | 0.009 |
| Cpd-2 | 0.036 |
| HBS-1 | 0.11 |
| Gelatin | 0.70 |

The fifth layer (high-speed red-sensitive emulsion layer)

| | |
|---|---|
| Silver bromoiodide emulsion E | silver 1.62 |
| ExS-1 | $2.0 \times 10^{-4}$ |
| ExS-2 | $1.0 \times 10^{-5}$ |
| ExS-3 | $3.0 \times 10^{-4}$ |
| ExC-1 | 0.133 |
| ExC-3 | 0.040 |
| ExC-6 | 0.040 |
| ExC-8 | 0.014 |
| Cpd-2 | 0.050 |
| HBS-1 | 0.22 |
| HBS-2 | 0.10 |
| Gelatin | 0.85 |

The sixth layer (intermediate layer)

| | |
|---|---|
| Cpd-1 | 0.07 |
| HBS-1 | 0.04 |
| Polyethyl acrylate latex | 0.19 |
| Gelatin | 2.30 |

The seventh layer (low-speed green-sensitive emulsion layer)

| | |
|---|---|
| Silver bromoiodide emulsion A | silver 0.24 |
| Silver bromoiodide emulsion B | silver 0.10 |
| Silver bromoiodide emulsion C | silver 0.14 |
| ExS-4 | $4.0 \times 10^{-5}$ |
| ExS-5 | $1.8 \times 10^{-4}$ |
| ExS-6 | $6.5 \times 10^{-4}$ |
| ExM-1 | 0.005 |
| ExM-2 | 0.30 |
| ExM-3 | 0.09 |
| ExY-1 | 0.015 |
| HBS-1 | 0.26 |
| HBS-3 | 0.006 |
| Gelatin | 0.80 |

The eighth layer (medium-speed green-sensitive emulsion layer)

| | |
|---|---|
| Silver bromoiodide emulsion D | silver 0.94 |
| ExS-4 | $2.0 \times 10^{-5}$ |
| ExS-5 | $1.4 \times 10^{-4}$ |
| ExS-6 | $5.4 \times 10^{-4}$ |
| ExM-2 | 0.16 |
| ExM-3 | 0.045 |
| ExY-1 | 0.008 |
| ExY-5 | 0.030 |
| HBS-1 | 0.14 |
| HBS-3 | $8.0 \times 10^{-3}$ |
| Gelatin | 0.90 |

The ninth layer (high-speed green-sensitive emulsion layer)

| | |
|---|---|
| Silver bromoiodide emulsion E | silver 1.29 |
| ExS-4 | $3.7 \times 10^{-5}$ |
| ExS-5 | $8.1 \times 10^{-5}$ |
| ExS-6 | $3.2 \times 10^{-4}$ |
| ExC-4 | 0.011 |
| ExM-1 | 0.016 |
| ExM-4 | 0.046 |
| ExM-5 | 0.023 |
| Cpd-3 | 0.050 |
| HBS-1 | 0.20 |
| HBS-2 | 0.08 |
| Polyethyl acrylate latex | 0.26 |
| Gelatin | 0.82 |

The tenth layer (yellow filter layer)

| | |
|---|---|
| Yellow colloidal silver | silver 0.010 |
| Cpd-1 | 0.10 |
| ExF-5 (solid dispersed dye) | 0.06 |
| ExF-6 (solid dispersed dye) | 0.06 |
| ExF-7 (oil-soluble dye) | 0.005 |

-continued

| | |
|---|---|
| HBS-1 | 0.055 |
| Gelatin | 0.70 |

The eleventh layer (low-speed blue-sensitive emulsion layer)

| | |
|---|---|
| Silver bromoiodide emulsion A | silver 0.25 |
| Silver bromoiodide emulsion C | silver 0.25 |
| Silver bromoiodide emulsion D | silver 0.10 |
| ExS-7 | $8.0 \times 10^{-4}$ |
| ExY-1 | 0.010 |
| ExY-2 | 0.70 |
| ExY-3 | 0.055 |
| ExY-4 | 0.006 |
| ExY-6 | 0.075 |
| ExC-7 | 0.040 |
| HBS-1 | 0.25 |
| Gelatin | 1.60 |

The twelfth layer (high-speed blue-sensitive emulsion layer)

| | |
|---|---|
| Silver bromoiodide emulsion F | silver 1.30 |
| ExS-7 | $3.0 \times 10^{-4}$ |
| ExY-2 | 0.15 |
| ExY-3 | 0.06 |
| HBS-1 | 0.070 |
| Gelatin | 1.13 |

The thirteenth layer (the first protective layer)

| | |
|---|---|
| UV-2 | 0.08 |
| UV-3 | 0.11 |
| UV-4 | 0.26 |
| HBS-1 | 0.09 |
| Gelatin | 1.20 |

The fourteenth layer (the second protective layer)

| | |
|---|---|
| Silver bromoiodide emulsion G | silver 0.10 |
| H-1 | 0.30 |
| B-1 (diameter: 1.7 μm) | $5.0 \times 10^{-2}$ |
| B-2 (diameter: 1.7 μm) | 0.10 |
| B-3 | 0.10 |
| S-1 | 0.20 |
| Gelatin | 1.75 |

Further, the respective layers suitably contain W-1 to W-3, B-4 to B-6, F-1 to F-17, iron salts, lead salts, gold salts, platinum salts, iridium salts, palladium salts and rhodium salts in order to improve the storability, processability, pressure resistance, mildew-proofing and bacteria-proofing properties, antistatic properties and coating easiness.

TABLE 1

| Emulsion | Average AgI content (%) | Average grain diameter (μm) | Coefficient of variation of grain diameter (%) | Rate of grains having diameter/thickness ratio of at least 2 (%) | Grain structure/shape |
|---|---|---|---|---|---|
| A | 2.1 | 0.55 | 25 | 81 | homogeneous structure, tabular |
| B | 9.1 | 0.63 | 26 | 84 | triple structure, tabular |
| C | 3.1 | 0.60 | 24 | 98 | triple structure, tabular |
| D | 4.2 | 0.80 | 19 | 92 | triple structure, tabular |
| E | 3.2 | 1.10 | 17 | 96 | triple structure, tabular |
| F | 10.8 | 1.75 | 27 | 60 | double structure, tabular |
| G | 1 | 0.07 | 15 | 0 | homogeneous structure, cubic |

In Table 1:

(1) The emulsions A to F were reduction-sensitized with thiourea dioxide and thiosulfonic acid in the step of preparation of the grains as described in an Example of J.P. KOKAI No. Hei 2-191938.

(2) The emulsions A to F were sensitized by gold sensitization, sulfur sensitization and selenium sensitization methods in the presence of a spectral sensitizing dye mentioned above for each photosensitive layer and sodium thiocyanate as described in an Example of J.P. KOKAI No. Hei 3-237450.

(3) In the preparation of tabular grains, a low-molecular weight gelatin was used as described in an Example of J.P. KOKAI No. Hei 1-158426.

(4) Dislocation lines as described in J.P. KOKAI No. Hei 3-237450 were observed on the tabular grains with a high-voltage electron microscope.

Preparation of dispersion of organic solid disperse dye:

ExF-2 which will be described below was dispersed as follows: 21.7 ml of water, 3 ml of 5% aqueous solution of sodium p-octylphenoxyethoxyethanesulfonate and 0.5 g of 5% aqueous solution of p-octylphenoxy polyoxyethylene ether (degree of polymerization: 10) were fed into a 700 ml pot mill. 5.0 g of dye ExF-2 and 500 ml of zirconium oxide beads (diameter: 1 mm) were added thereto, and the mixture was milled with a BO type vibration ball mill (a product of Chuo Koki) for 2 hours to obtain a dispersion. Then the dispersion was taken out and added to 8 g of 12.5% aqueous gelatin solution. The beads were removed by filtration to obtain a dispersion of the dye in gelatin. The average grain diameter of the fine dye grains was 0.44 μm.

A solid dispersion of each of ExF-3, ExF-4 and ExF-6 was obtained in the same manner as that described above. The average grain diameters of the fine dye grains were 0.24 μm, 0.45 μm and 0.52 μm, respectively. ExF-5 was dispersed by a microprecipitation dispersion method described in Example 1 in E. P. No. 0,549,489 A. The average grain diameter was 0.06 μm.

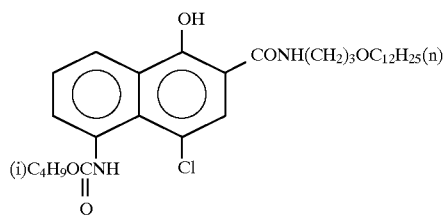
ExC-1
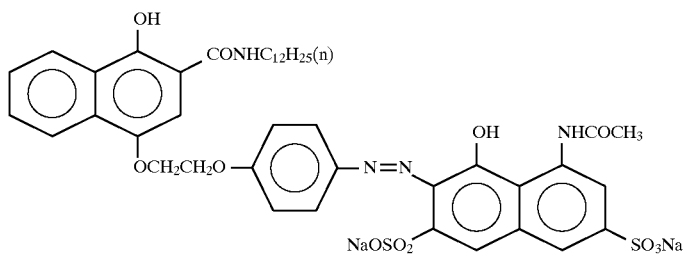
ExC-2
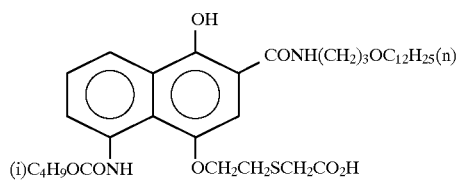
ExC-3
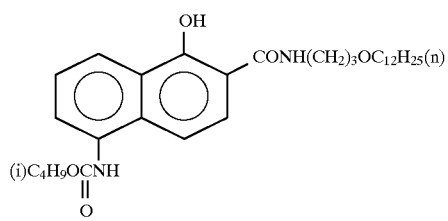
ExC-4
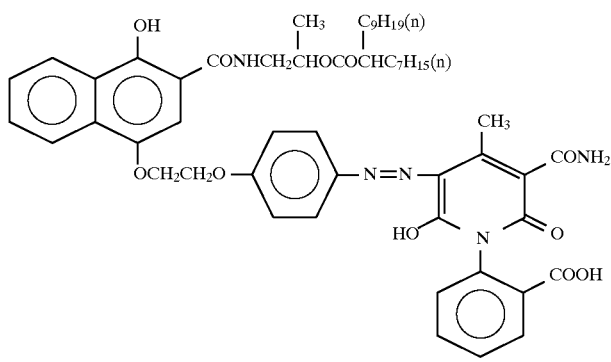
ExC-5

-continued
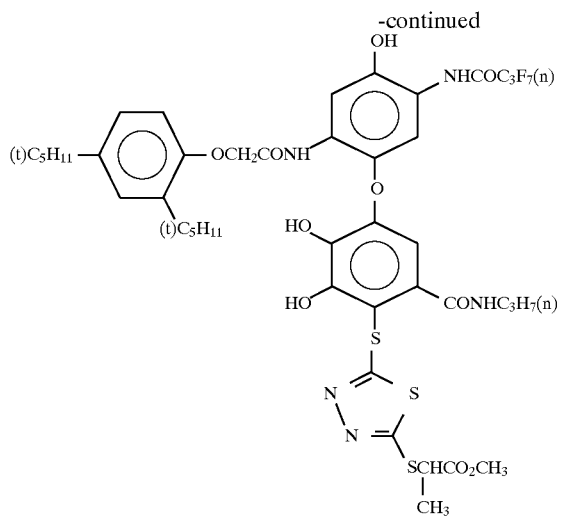
ExC-7
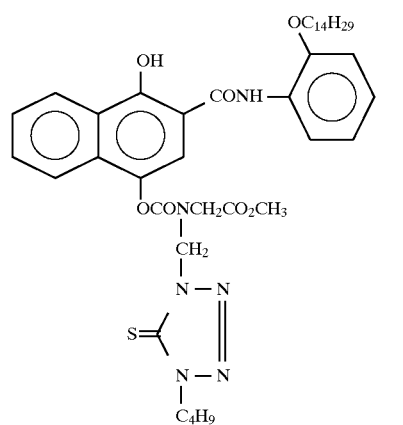
ExC-8
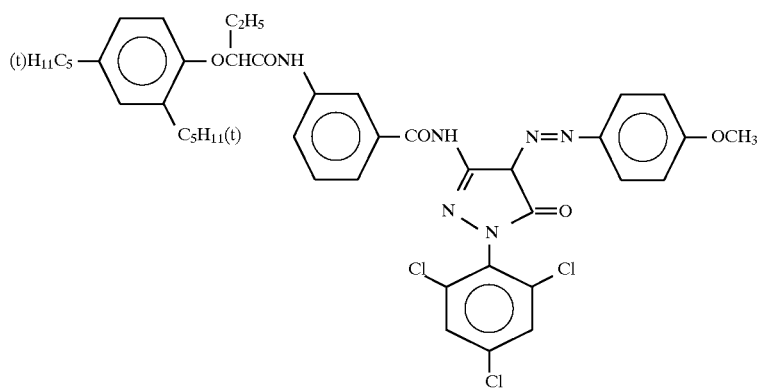
ExM-1
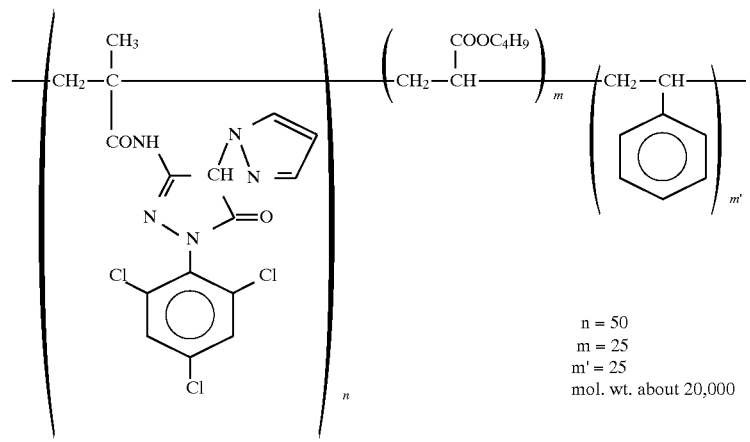
ExM-2
n = 50
m = 25
m' = 25
mol. wt. about 20,000

-continued
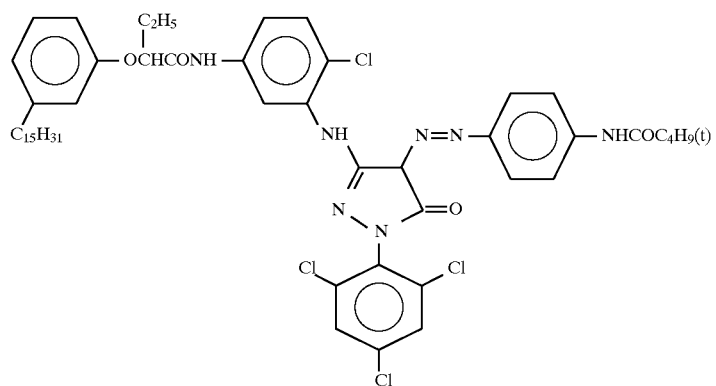
ExM-3
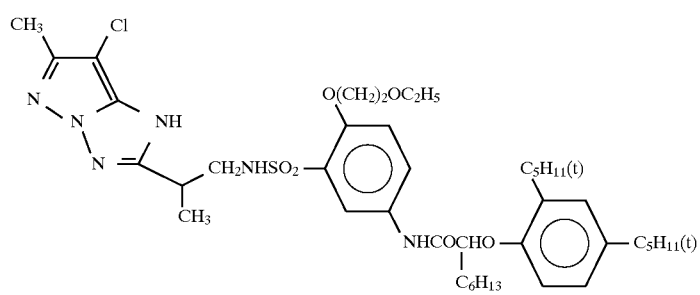
ExM-4
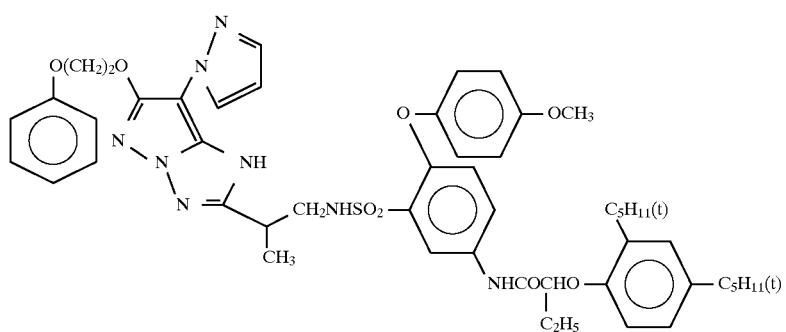
ExM-5
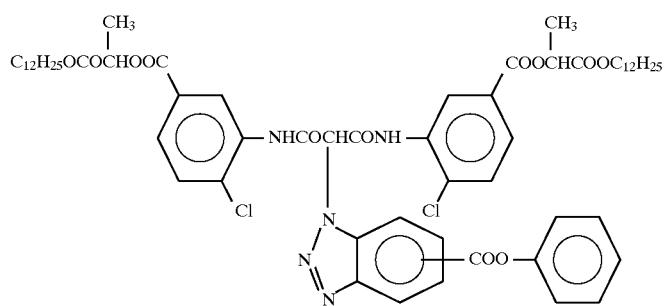
ExY-1
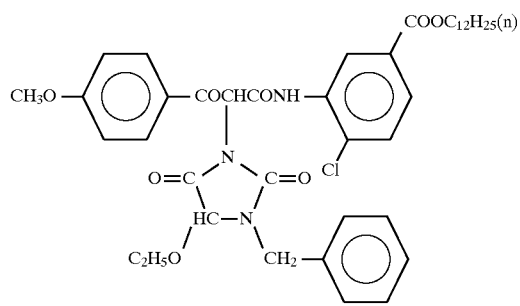
ExY-2

-continued
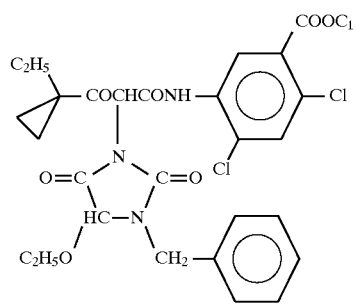
ExY-3
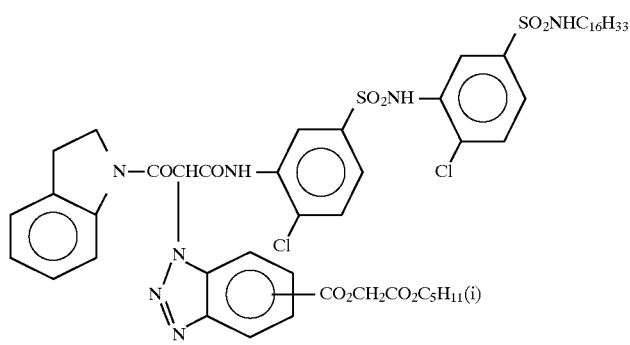
ExY-4
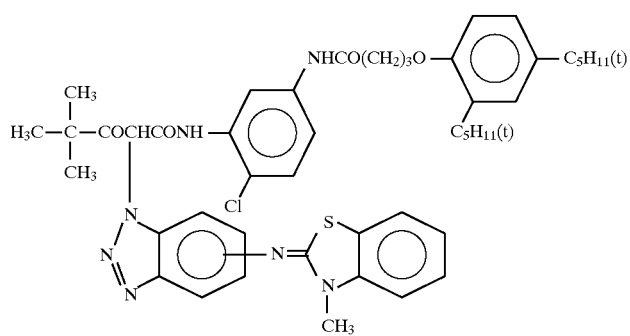
ExY-5
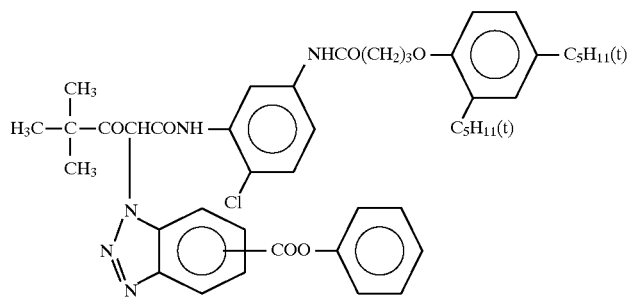
ExY-6
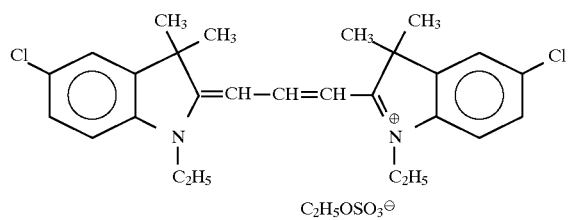
ExF-1

-continued
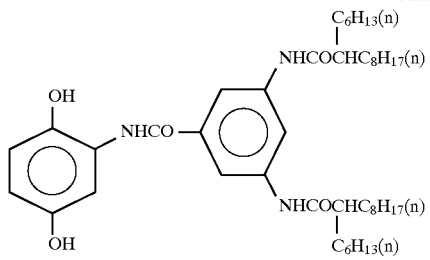  Cpd-1
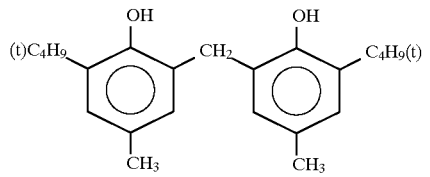  Cpd-2
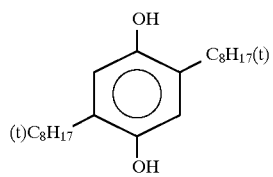  Cpd-3
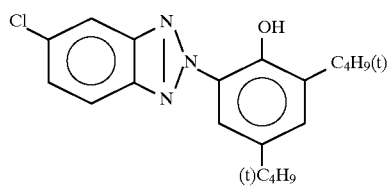  UV-1
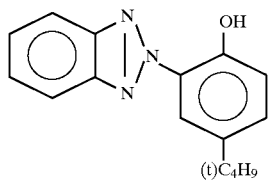  UV-2
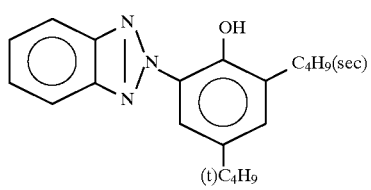  UV-3
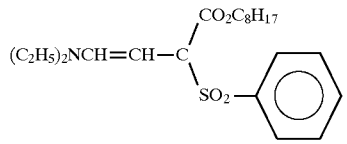  UV-4
Tricresylphosphate   HBS-1
Di-n-butylphthalate   HBS-2
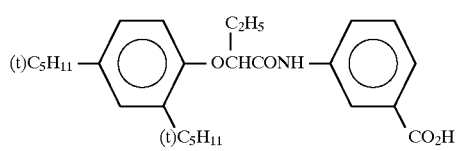  HBS-3

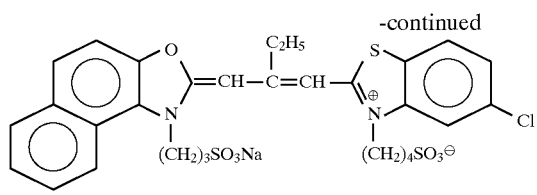
ExS-1
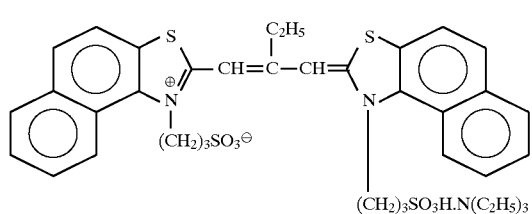
ExS-2
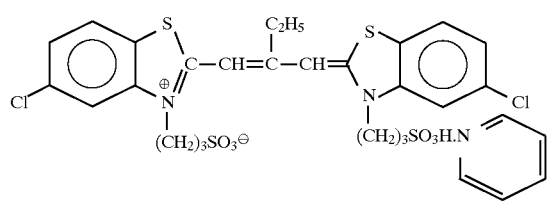
ExS-3
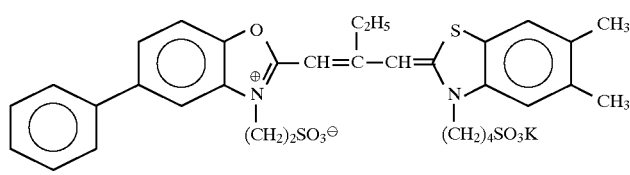
ExS-4
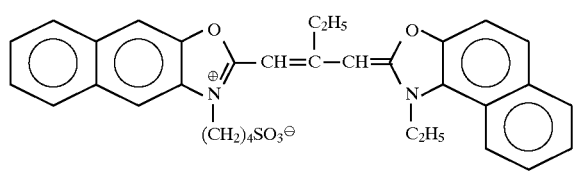
ExS-5
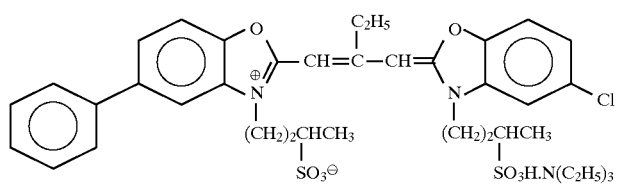
ExS-6
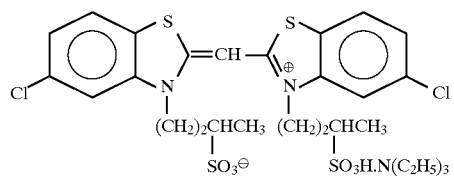
ExS-7
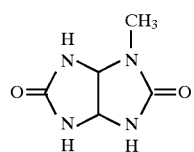
S-1
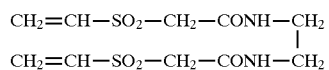
H-1
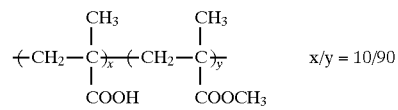   x/y = 10/90
B-1

-continued
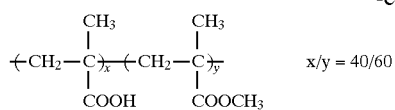
B-2
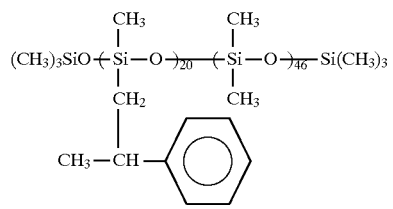
B-3
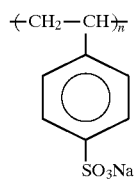
B-4
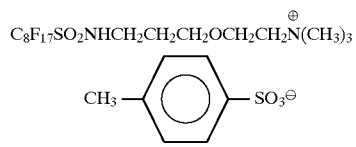
W-1
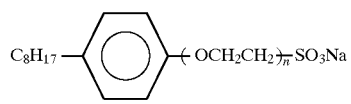
W-2
n = 2~4
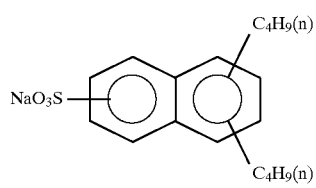
W-3
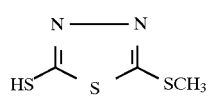
F-1
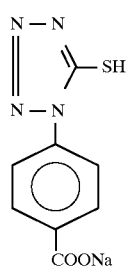
F-2
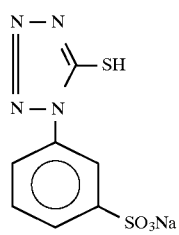
F-3

-continued
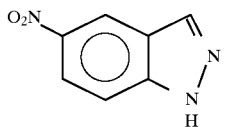
F-4
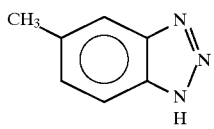
F-5
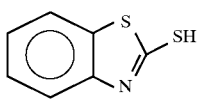
F-6
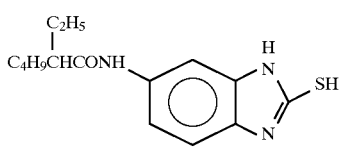
F-7
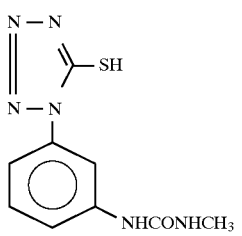
F-8
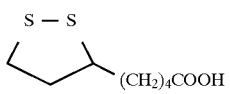
F-9
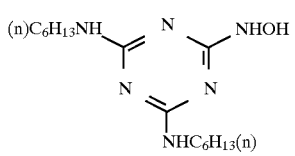
F-10
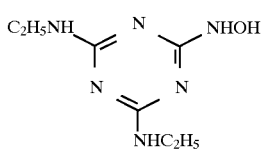
F-11
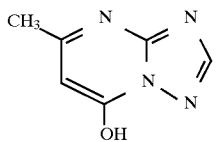
F-12
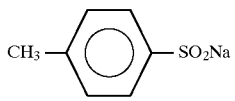
F-13
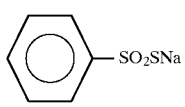
F-14
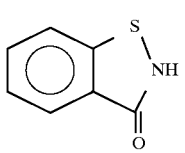
F-15

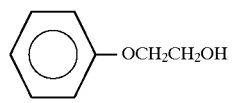
F-16
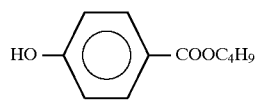
F-17
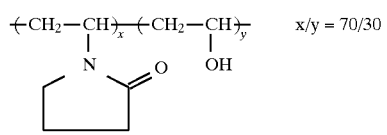 x/y = 70/30
B-5
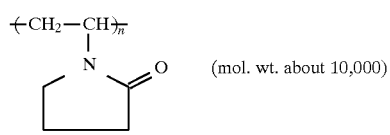 (mol. wt. about 10,000)
B-6
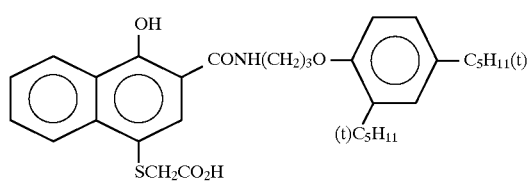
ExC-6
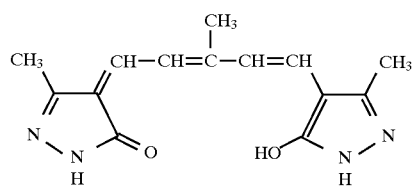
ExF-3
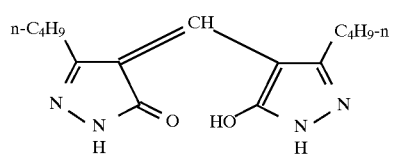
ExF-6
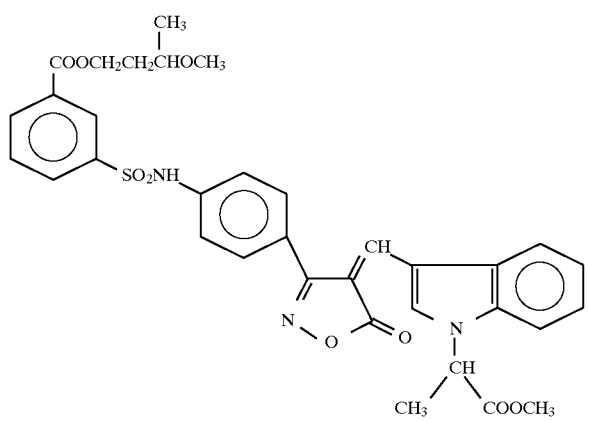
ExF-7

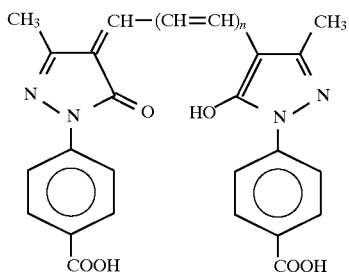

(n = 2)
(n = 1)
(n = 0)

ExF-2
ExF-4
ExF-5

(Processing step)

| Step | Process time | Process temp. | Amount of replenisher* | Capacity of tank, l |
|---|---|---|---|---|
| Color development | 3 min | 40.0° C. | 200 ml | 2.0 |
| Bleaching | 30 sec | 45.0° C. | 130 ml | 0.7 |
| Fixing (1) | 30 sec | 45.0° C. | 100 ml | 0.7 |
| Fixing (2) | 30 sec | 45.0° C. | 70 ml | 0.7 |
| Washing with water (1) | 15 sec | 45.0° C. | — | 0.4 |
| Washing with water (2) | 15 sec | 45.0° C. | 400 ml | 0.4 |
| Stabilization | 15 sec | 45.0° C. | 400 ml | 0.4 |
| Drying | 20 sec | 80° C. | | |

*The amount of the replenisher is given per m² of the photosensitive material. (The steps ranging from the washing with water (2) to the fixing (2) were conducted with three tanks by counter-current multi-stage cascade method.) (The steps ranging from the fixing (2) to fixing (1) were conducted with two tanks by counter-current multi-stage cascade method.)

The description will be made on the composition of each solution:

| (Color developer) | Mother liquid | Replenisher |
|---|---|---|
| Diethylenediaminetetraacetic acid | 4.0 g | 4.0 g |
| Sodium 4,5-dihydroxybenzene-1,3-disulfonate | 0.5 g | 0.5 g |
| Sodium sulfite | 3.9 g | 6.5 g |
| Potassium carbonate | 37.5 g | 39.0 g |
| Potassium bromide | 2.7 g | — |
| Potassium iodide | 1.3 mg | — |
| N-Methylhydroxylamine hydrochloride | 4.5 g | 5.5 g |
| 2-Methyl-4-[N-ethyl-N-(β-hydroxyethyl)amino]-aniline sulfate (P-5) | 5.0 g | 9.0 g |
| Water ad | 1000 ml | 1000 ml |
| pH (adjusted with potassium hydroxide and sulfuric acid) | 10.05 | 10.25 |

| (Bleaching solution) | Mother liquid | Replenisher |
|---|---|---|
| Ferric ammonium 1,3-diaminopropanetetraacetate monohydrate | 0.33 mol | 0.50 mol |
| Ferric nitrate nonahydrate | 0.30 mol | 4.5 mol |
| Ammonium bromide | 0.80 mol | 1.20 mol |
| Ammonium nitrate | 0.20 mol | 0.30 mol |
| Acetic acid | 0.67 mol | 1.0 mol |
| Water ad | 1000 ml | 1000 ml |
| pH (adjusted with ammonia water) | 4.5 | 4.0 |

| (Fixing solution) (common to the mother liquid and replenisher) (g) | |
|---|---|
| Ammonium sulfite | 28 |
| Aqueous ammonium thiosulfate solution (700 g/l) | 280 ml |
| Imidazole | 15 |
| Ethylenediaminetetraacetic acid | 15 |
| Water | 1.0 l |
| pH (adjusted with ammonia water and acetic acid) | 5.8 |

(Washing water) (common to the mother liquid and replenisher)

Tap water was passed through a mixed bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water. pH of the water was in the range of 6.5 to 7.5.

| (Stabilizer) (common to the mother liquid and replenisher) | |
|---|---|
| 1,2-Benzoylisothiazoline-3-on | 0.1 |
| Polyoxyethylene-p-mononylphenyl ether (average degree of polymerization: 10) | 0.2 |
| Water ad | 1.0 l |
| pH (adjusted with ammonia water and hydrochloric acid) | 8.50. |

After image-exposure of the sample 101, the continuous process was conducted until the amount of the replenished bleach fixing solution had become three times as much as the amount of the mother liquid.

The running processing solution thus obtained will be referred to as processing solution 201. Then the color developer was prepared in the same manner as above except that the color developing agent P-5 sulfate in the color developer was replaced with an equal molar amount of a comparative color developing agent or the color developing agent of the present invention as shown in Table 2, and the same continuous process as that described above was conducted to obtain running processing solutions (processing solutions 202 to 216).

The rapidness of the process was determined as follows. After the wedge exposure of the sample 101, it was processed [running process step (a)] with a running processing solution (processing solutions 202 to 216) while the color development period was changed from 1 minute to 3 minutes at intervals of 10 seconds. The optical densities of the yellow, magenta and cyan images of each of the resultant samples were determined. Then, after the wedge-exposure of the sample 101 conducted in the same manner as that described above, it was processed in comparative developing steps (b) described below, and the optical densities of the yellow, magenta and cyan images were determined in the same manner as that described above. The density curve of the magenta image obtained in the comparative developing steps (b) was compared with that of each sample (obtained at intervals of 10 seconds as described above), and the processing time for the color development in which the equal or higher magenta density was obtained was measured to obtain the results shown in Table 2.

Then the degree of lowering of the density of each of the yellow and cyan images was determined by using a sample which necessitated an equal processing time for obtaining the same magenta density. The yellow and cyan densities of each sample were determined with such an exposure that magenta density of 2.0 would be obtained. The densities [minus (−) means lowering of the density and plus (+) means increase thereof] are given in Table 2 as compared with the yellow and cyan densities obtained in the comparative developing steps (b). Further, the yellow fog density of the sample was determined, and the difference thereof from that obtained in the comparative development steps (b) is shown in Table 2.

Comparative color developing agent:

Comparative compound-1

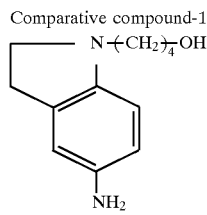

The compound described in
JP Kokai No. Hei 4-45440

Comparative compound-2

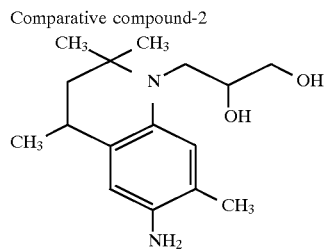

The compound described in
EP No. 670,312A1

Comparative compound-3

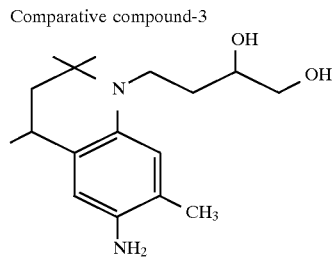

The compound described in
EP No. 670,312A1

Comparative compound-4

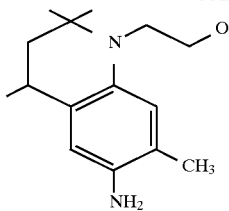

Comparative compound-5

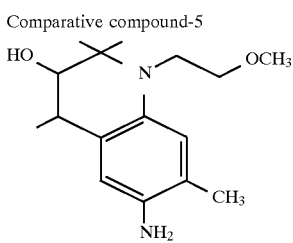

Comparative development steps (b) (Processing method)

| Step | Time | Temp. |
| --- | --- | --- |
| Color development | 3 min 15 sec | 38° C. |
| Bleaching | 1 min 00 sec | 38° C. |
| Bleach-fixing | 3 min 15 sec | 38° C. |
| Washing with water (1) | 40 sec | 35° C. |
| Washing with water (2) | 1 min 00 sec | 35° C. |
| Stabilization | 40 sec | 38° C. |
| Drying | 1 min 15 sec | 55° C. |

The composition of each of the processing solutions was as follows:

| | (Unit: g) |
| --- | --- |
| (Color developer) | |
| Diethylenetriaminepentaacetic acid | 1.0 |
| 1-Hydroxyethylidene-1,1-diphosphonic acid | 2.0 |
| Sodium sulfite | 4.0 |
| Potassium carbonate | 30.0 |
| Potassium bromide | 1.4 |
| Potassium iodide | 1.5 mg |
| Hydroxylamine sulfate | 2.4 |
| 4-[N-ethyl-N-(β-hydroxyethyl)amino]-2-methyl-aniline sulfate [P-5] | 4.5 |
| Water ad | 1.0 l |
| pH (with potassium hydroxide and sulfuric acid) | 10.05 |
| (Bleaching bath) | |
| Ferric ammonium ethylenediaminetetraacetate dihydrate | 120.0 |
| Disodium ethylenediaminetetraacetate | 10.0 |
| Ammonium bromide | 100.0 |
| Ammonium nitrate | 10.0 |
| Bleaching accelerator $(CH_3)_2N-CH_2-CH_2-S-S-CH_2-CH_2-N(CH_3)_2 \cdot 2HCl$ | 0.005 mol |
| Ammonia water (27%) | 15.0 ml |
| Water ad | 1.0 l |
| pH (adjusted with ammonia water and nitric acid) | 6.3 |
| (Bleach-fixing bath) | |
| Ferric ammonium ethylenediaminetetraacetate dihydrate | 50.0 |
| Disodium ethylenediaminetetraacetate | 5.0 |
| Sodium sulfite | 12.0 |
| Aqueous ammonium thiosulfate solution (700 g/l) | 240.0 ml |
| Ammonia water (27%) | 6.0 ml |
| Water ad | 1.0 l |
| pH (adjusted with ammonia water and acetic acid) | 7.2 |

(Washing water)

Tap water was passed through a mixed bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water.. pH of the water was in the range of 6.5 to 7.5.

| (Stabilizing bath) | (unit: g) |
|---|---|
| Sodium p-toluenesulfinate | 0.03 |
| Polyoxyethylene p-monononylphenyl ether (average degree of polymerization: 10) | 0.2 |
| Disodium ethylenediaminetetraacetate | 0.05 |
| 1,2,4-Triazole | 1.3 |
| 1,4-Bis(1,2,4-triazol-1-ylmethyl)piperazine | 0.75 |
| Water ad | 1.0 l |
| pH | 8.5 |

TABLE 2

| Process No. | Color developing agent | Color development time for obtaining given magenta density |
|---|---|---|
| 201 | P-5 | 2 min 50 sec |
| 202 | Comp. compound-1 | 2 min 20 sec |
| 203 | Comp. compound-2 | 2 min 10 sec |
| 204 | Comp. compound-3 | 2 min 10 sec |
| 205 | Comp. compound-4 | 2 min 10 sec |
| 206 | Comp. compound-5 | 2 min 20 sec |
| 207 | D-2 | 2 min 10 sec |
| 208 | D-7 | 2 min 10 sec |
| 209 | D-59 | 2 min 00 sec |
| 210 | D-60 | 2 min 00 sec |
| 211 | D-61 | 2 min 00 sec |
| 212 | D-70 | 2 min 00 sec |
| 213 | D-86 | 2 min 00 sec |
| 214 | D-126 | 2 min 10 sec |
| 215 | D-156 | 2 min 00 sec |
| 216 | D-160 | 2 min 10 sec |

| Process No. | Difference in yellow density | Difference in cyan density | Difference in yellow fog density | Remarks |
|---|---|---|---|---|
| 201 | +0.04 | −0.02 | +0.02 | Comp. Ex. |
| 202 | −0.60 | −0.32 | +0.27 | Comp. Ex. |
| 203 | −0.77 | −0.49 | +0.30 | Comp. Ex. |
| 204 | −0.85 | −0.46 | +0.22 | Comp. Ex. |
| 205 | −0.40 | −0.53 | +0.32 | Comp. Ex. |
| 206 | −0.60 | −0.72 | +0.48 | Comp. Ex. |
| 207 | −0.10 | −0.02 | +0.11 | Invention |
| 208 | 0 | +0.07 | +0.10 | Invention |
| 209 | +0.25 | +0.02 | +0.12 | Invention |
| 210 | +0.10 | +0.04 | +0.14 | Invention |
| 211 | +0.14 | +0.08 | +0.10 | Invention |
| 212 | 0 | −0.01 | +0.02 | Invention |
| 213 | +0.09 | +0.06 | +0.13 | Invention |
| 214 | −0.12 | −0.05 | +0.11 | Invention |
| 215 | +0.20 | +0.06 | +0.13 | Invention |
| 216 | +0.18 | +0.10 | +0.12 | Invention |

It is apparent from Table 2 that with the color developing agent of the present invention or each of the comparative compounds 1 to 5, the magenta image density can be obtained in a development process time far shorter than that necessitated when P-5 (processing solution No. 201) is used.

It will be understood that although a high rapidness can be attained with the comparative compounds 1 to 5, it is not easy to obtain a satisfactory yellow density or cyan density and yellow fog density is high when they are used.

With the color developing agent of the present invention, the yellow density and cyan density could be remarkably improved while the yellow fog density could be kept low.

Namely, by using the developing agent of the present invention, the rapidness of the process could be increased, yellow density and cyan density could be secured while yellow fog density could be kept low.

Example 9

The same sample 101 as that used in Example 8 was exposed. After the development by using the compound (D-62) of the present invention as the color developing agent in the color developer by a method which will be described below, a desired gradation could be obtained in a color development time of as short as only 60 seconds. Another advantage was that the fog density was low. The similar results could be obtained when the compound (D-62) was replaced with compound (D-2), (D-7), (D-59) or (D-60). Development steps and compositions of processing liquids:

| Step | Temp. | Time |
|---|---|---|
| Color development | 45° C. | 60 sec |
| Bleach-fixing | 45° C. | 60 sec |
| Washing with water (1) | 40° C. | 15 sec |
| Washing with water (2) | 40° C. | 15 sec |
| Washing with water (3) | 40° C. | 15 sec |
| Stabilization | 40° C. | 15 sec |
| Drying | 80° C. | 30 sec |

The washing with water was conducted with three tanks by counter-current method from (3) to (1).

Liquid composition:

| (Color developer) | Mother liquid (g) |
|---|---|
| Diethylenetriaminepentaacetic acid | 4.0 |
| 1-Hydroxyethylidene-1,1-diphosphonic acid | 3.0 |
| Sodium sulfite | 4.0 |
| Potassium carbonate | 50.0 |
| Potassium bromide | 4.0 |
| Potassium iodide | 1.3 mg |
| Hydroxylamine sulfate | 4.0 |
| Color developing agent (D-62.naphthalene-1,5-disulfonate) | 22.8 |
| Water ad | 1.0 l |
| pH (adjusted with potassium hydroxide and sulfuric acid) | 10.05 |

| (Bleach-fixing bath) | (unit: mol) |
|---|---|
| Chelating agent represented by formula A | 0.17 |
| Ferric nitrate nonahydrate | 0.15 |
| Ammonium thiosulfate | 1.25 |
| Ammonium sulfite | 0.10 |
| M-carboxybenzenesulfinic acid | 0.05 |
| Water ad | 1.0 l |
| pH (adjusted with acetic acid and ammonia) | 5.8 |

(Washing water)

Tap water was passed through a mixed bed column packed with an H-type strongly acidic cation exchange resin (Amberlite IR-120B; a product of Rohm & Haas Co.) and an OH-type anion exchange resin (Amberlite IR-400; a product of Rohm & Haas Co.) to reduce calcium and magnesium ion concentration to 3 mg/l or below, and then 20 mg/l of sodium isocyanurate dichloride and 0.15 g/l of sodium sulfate were added to the water. pH of the water was in the range of 6.5 to 7.5.

| (Stabilizing bath) | Mother liquid (g) |
|---|---|
| 1,2-Benzoisothiazoline-3-on | 0.1 |
| Polyoxyethylene p-monononylphenyl ether (average degree of polymerization: 10) | 0.2 |
| Water ad | 1.0 l |
| pH (adjusted with ammonia water and hydrochloric acid) | 8.50 |

Formula A

H₃CO—⟨benzene ring⟩—COOH, with —NCH₂CH₂N(CH₂COOH)₂ and HOOCH₂C— substituents

Example 10

The same sample 101 as that used in Example 8 was exposed and then processed with the color developing agent D-33 or D-144 in the color developer by process Nos. 211–213. The image fastness of the samples of a magenta density of 2.0 were examined to find that an excellent image fastness was obtained with the compounds of the present invention.

Example 11

A sample 301 in Example 3 of J. P. KOKAI No. Hei 5-188550 was exposed and then developed by the same method as that described in that specification except that the color developing agent in the color developer was replaced with an equimolar amount of the color developing agent (D-2), (D-59), (D-60), (D-62), (D-70), (D-86) or (D-150) of the present invention. The development time could be reduced, the fog density was low, and the difference among the magenta density, yellow density and cyan density was only slight favorably.

When the compound of the present invention is used as the color developing agent, the process can be rapidly conducted, an image having sufficient yellow, magenta and cyan image densities and a low fog density can be obtained.

What is claimed is:

1. A color image-forming method which comprises the setup of developing an image-exposed silver halide color photographic photosensitive material in the presence of an aniline compound represented by the following general formula (I):

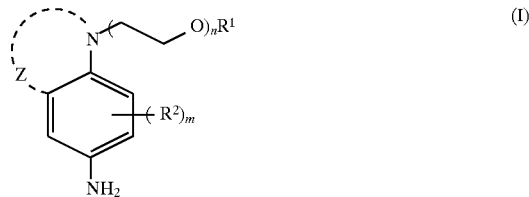

wherein $R^1$ represents a hydrogen atom or substituent, $R^2$ represents a substituent, Z represents a substituted or unsubstituted ethylene group or substituted or unsubstituted trimethylene group, n represents an integer of 2 to 8, and m represents 0 or an integer of 1 to 3, and when m is 2 or larger, $R^2$'s may be the same or different from each other.

2. The method of claim 1 wherein n represents 2 to 5.

3. The method of claim 1 wherein $R^1$ represents a hydrogen atom or substituent having 1 to 20 carbon atoms, $R^2$ represents a substituent having 0 to 20 carbon atoms, and Z represents a substituted or unsubstituted ethylene group or substituted or unsubstituted trimethylene group, each group of which has 2 to 20 carbon atoms.

4. The method of claim 1 wherein $R^1$ represents a hydrogen atom or substituent having 1 to 20 carbon atoms selected from the group consisting of alkyl groups, aryl groups and heterocyclic groups, $R^2$ represents a substituent having 1 to 20 carbon atoms selected from the group consisting of alkyl, alkoxy, carbamoyl, sulfamoyl and ureido groups, and Z represents a substituted or unsubstituted ethylene group or substituted or unsubstituted trimethylene group, each group of which has 2 to 20 carbon atoms wherein a substituent in the substituted ethylene group or substituted trimethylene group is selected from the group consisting of hydroxyl, alkyl, carboxyl, acylamino, ureido, alkoxycarbonylamino, sulfonylamino, carbamoyl, acyloxy and carbamoyloxy groups.

5. The method of claim 1 wherein $R^1$ represents a hydrogen atom or substituent having 1 to 8 carbon atoms, $R^2$ represents a substituent having 1 to 3 carbon atoms, Z represents a substituted or unsubstituted ethylene group or substituted or unsubstituted trimethylene group, each group of which has 2 to 6 carbon atoms, and m represents 0 or 1.

6. The method of claim 1 wherein $R^1$ represents a hydrogen atom or substituent having 1 to 8 carbon atoms selected from the group consisting of alkyl groups, aryl groups and heterocyclic groups, $R^2$ represents a substituent having 1 to 3 carbon atoms selected from the group consisting of alkyl, alkoxy, carbamoyl, sulfamoyl and ureido groups, Z represents a substituted or unsubstituted ethylene group or substituted or unsubstituted trimethylene group, each group of which has 2 to 6 carbon atoms wherein a substituent in the substituted ethylene group or substituted trimethylene group is selected from the group consisting of hydroxyl, alkyl and carboxyl groups, and m represents 0 or 1.

7. The method of claim 1 wherein $R^1$ represents a hydrogen atom or alkyl group having 1 to 8 carbon atoms, $R^2$ represents a substituent having 1 to 3 carbon atoms selected from the group consisting of alkyl and alkoxy groups, Z represents a substituted or unsubstituted ethylene group or substituted or unsubstituted trimethylene group, each group of which has 2 to 6 carbon atoms wherein a substituent in the substituted ethylene group or substituted trimethylene group is selected from the group consisting of hydroxyl, alkyl and carboxyl groups, and m represents 0 or 1.

8. The method of claim 1 wherein $R^1$ represents a hydrogen atom or alkyl group having 1 to 3 carbon atoms, $R^2$ represents a substituent having 1 to 3 carbon atoms selected from the group consisting of alkyl and alkoxy groups, Z represents a substituted or unsubstituted ethylene group or substituted or unsubstituted trimethylene group, each group of which has 2 to 6 carbon atoms wherein a substituent in the substituted ethylene group or substituted trimethylene group is selected from the group consisting of hydroxyl, alkyl and carboxyl groups, and m represents 0 or 1.

9. A color image-forming method which comprises the setup of developing an image-exposed silver halide color photographic photosensitive material in the presence of an aniline compound represented by the following general formula (I-a):

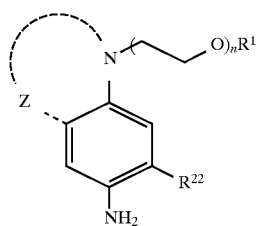
(I-a)

wherein R¹ represents a hydrogen atom or alkyl group having 1 to 3 carbon atoms, $R^{22}$ represents a hydrogen atom, alkyl or alkoxy group having 1 to 3 carbon atoms, Z represents a substituted or unsubstituted ethylene group or substituted or unsubstituted trimethylene group, each group of which has 2 to 6 carbon atoms wherein a substituent in the substituted ethylene group or substituted trimethylene group is selected from the group consisting of hydroxyl, alkyl and carboxyl groups, and n represents an integer of 2 to 5.

* * * * *